United States Patent
Simmons et al.

(10) Patent No.: US 7,670,628 B2
(45) Date of Patent: Mar. 2, 2010

(54) MESENCHYMAL PRECURSOR CELL

(75) Inventors: Paul Simmons, Kew (AU); Andrew Zannettino, Highbury (AU); Stan Gronthos, Colonial Light Gardens (AU)

(73) Assignee: Angioblast Systems, Inc., New York, NY (US)

( * ) Notice: Subject to any disclaimer, the term of this patent is extended or adjusted under 35 U.S.C. 154(b) by 1236 days.

(21) Appl. No.: 10/813,747

(22) Filed: Mar. 29, 2004

(65) Prior Publication Data

US 2005/0019911 A1    Jan. 27, 2005

Related U.S. Application Data

(63) Continuation-in-part of application No. 10/030,411, filed as application No. PCT/AU00/00822 on Jul. 7, 2000, now Pat. No. 7,122,178.

(30) Foreign Application Priority Data

Jul. 7, 1999 (AU) .................... PQ1477
Mar. 28, 2003 (AU) ................ 2003901668

(51) Int. Cl.
*A61K 35/26* (2006.01)
(52) U.S. Cl. .................................. 424/577
(58) Field of Classification Search .................. None
See application file for complete search history.

(56) References Cited

U.S. PATENT DOCUMENTS

| | | | |
|---|---|---|---|
| 5,197,985 A | 3/1993 | Caplan et al. |
| 5,226,914 A | 7/1993 | Caplan et al. |
| 5,405,772 A | 4/1995 | Ponting et al. |
| 5,486,359 A | 1/1996 | Caplan et al. |
| 5,591,625 A | 1/1997 | Gerson et al. |
| 5,811,094 A | 9/1998 | Caplan |
| 5,827,740 A | 10/1998 | Pittenger |
| 5,837,539 A | 11/1998 | Caplan et al. |
| 5,922,597 A | 7/1999 | Verfaillie et al. |
| 5,980,887 A | 11/1999 | Isner et al. |
| 6,022,540 A | 2/2000 | Bruder et al. |
| 6,087,113 A | 7/2000 | Caplan et al. |
| 6,261,549 B1 | 7/2001 | Fernandez et al. |
| 6,322,784 B1 | 11/2001 | Pittenger et al. |
| 6,335,195 B1 | 1/2002 | Rodgers et al. |
| 6,387,367 B1 | 5/2002 | Davis-Sproul et al. |
| 6,387,369 B1 | 5/2002 | Pittenger et al. |
| 6,645,727 B2 | 11/2003 | Thomas et al. |
| 6,709,864 B1 | 3/2004 | Pittenger et al. |
| 6,875,430 B2 | 4/2005 | McIntosh et al. |
| 7,122,178 B1 | 10/2006 | Simmons et al. |
| 2004/0107453 A1 | 6/2004 | Furcht |
| 2005/0158289 A1 | 7/2005 | Simmons |
| 2005/0281790 A1 | 12/2005 | Simmons |
| 2006/0008452 A1 | 1/2006 | Simmons |
| 2006/0193840 A1 | 8/2006 | Gronthos et al. |
| 2006/0286077 A1 | 12/2006 | Gronthos et al. |
| 2007/0065938 A1 | 3/2007 | Gronthos et al. |
| 2007/0274958 A1 | 11/2007 | Shi et al. |

FOREIGN PATENT DOCUMENTS

| | | |
|---|---|---|
| WO | WO 00/06701 | 2/2000 |
| WO | WO 01/04268 A1 | 1/2001 |
| WO | WO 01/11011 | 2/2001 |
| WO | WO 02/07679 | 1/2002 |

OTHER PUBLICATIONS

Hansson et al., Stem Cells, 2007, V.25, pp. 1507-1510.*
Cochlovius et al (Modern Drug Discovery, 2003, pp. 33-34, 37-38.*
Poulsom et al, 2003, J Am. Soc. Nephrol, V.14 pp. s48-s54.*
Holden et al. Science, 2002, V.296, pp. 2126-2129.*
Shi, S. et al (2001) "Comparison of Human Dental Pulp and Bone Marrow Stromal Stem Cells by cDNA Microarray Analysis" *Bone*, 29(6):532-539.
Jones, E.A. et al (2002 "Isolation and Characterization of Bone Marrow Multipotential Mesenchymal Progenitor Cells" *Arthritis & Rheumatism*, 46(12):3349-60.
Gronthos, S. et al (2002) "Stem Cell Properties of Human Dental Pulp Stem Cells" *J. Dent. Res.*, 81(8):531-535.
Doherty, M.J. et al. (1998) "Vascular Pericytes Express Osteogenic Potential In Vitro and In Vitro" *Journal of Bone and Mineral Research*, 13:828-838.
Axelrad et al., New Technologies for the Enhancement of Skeletal Repair, Injury, Int. J. Care Injured (2007) 38S1:S49-S62.
Bruder et al., Mesenchymal Stem Cells in Bone Development, Bone Repair, and Skeletal Regeneration Therapy, J. Cell Biochem; (1994) 56:283-294.
Dennis et al., Osteogenesis in Marrow-Derived Mesenchymal Cell Porous Ceramic Composites Transplanted Subcutaneously: Effect of Fibronectin and Laminin on Cell Retention and Rate of Osteogenic Expression, Cell Transplant (1992) 1:23-32, Abstract.
Simmons and Gronthos (1991) Int'l J. Cell Cloning 9, p. 408 (abstract).
Office Action issued Jan. 12, 2005 in connection with U.S. Appl. No. 10/030,411.
Office Action issued Jun. 28, 2005 in connection with U.S. Appl. No. 10/030,411.
Final Office Action issued Jan. 9, 2006 in connection with U.S. Appl. No. 10/030,411.
Examiner Int'erview Summary issued Jun. 27, 2006 in connection with U.S. Appl. No. 10/030,411.
Office Action issued Apr. 20, 2007 in connection with U.S. Appl. No. 10/955,709.

(Continued)

*Primary Examiner*—Michail A Belyavskyi
(74) *Attorney, Agent, or Firm*—John P. White; Cooper & Dunham LLP

(57) ABSTRACT

A method of enriching mesenchymal precursor cells including the step of enriching for cells based on at least two markers. The markers may be either i) the presence of markers specific for mesenchymal precursor cells, ii) the absence of markers specific for differentiated mesenchymal cells, or iii) expression levels of markers specific for mesenchymal precursor cells. The method may include a first solid phase sorting step utilizing MACS recognizing expression of the antigen to the STRO-1 Mab, followed by a second sorting step utilizing two colour FACS to screen for the presence of high level STRO-1 antigen expression as well as the expression of VCAM-1.

4 Claims, 28 Drawing Sheets

OTHER PUBLICATIONS

Figure 1:
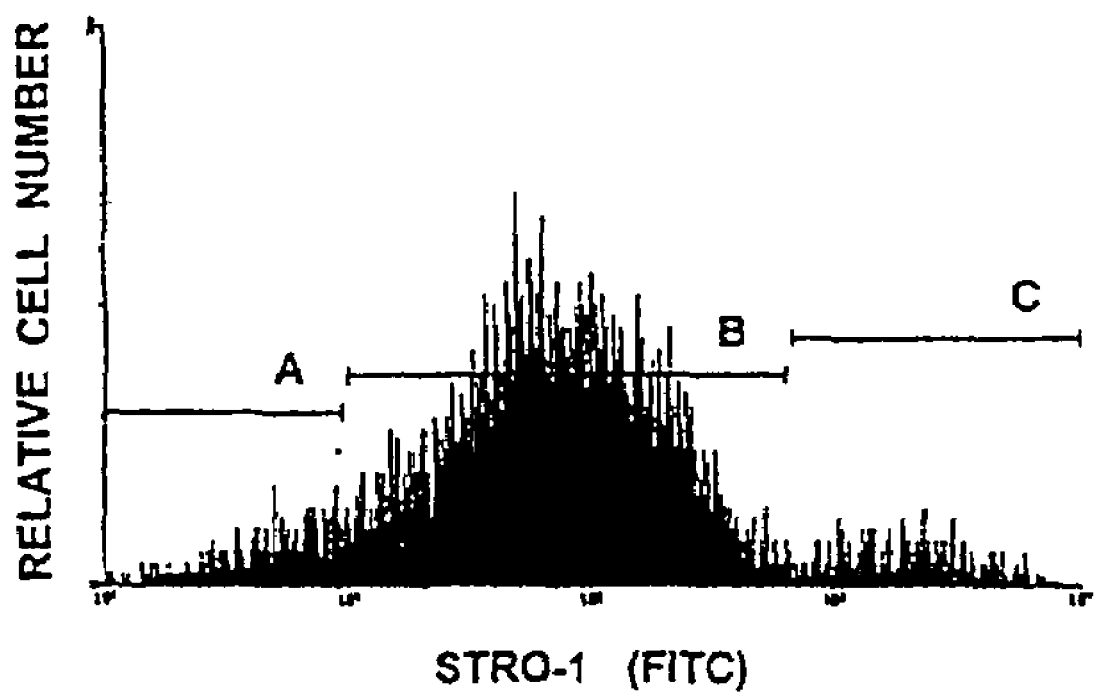

Alberico et al. (1987) Blood 69, p. 1120.
Allen, T.D., "Microenvironments in Haemopoietic and Lymphoid Differentiation" CIBA Found. Symposium 84, pp. 38-67.
Allen et al. (1990) Immunol. Ser. 49, p. 1.
Allen et al. (1990) "Marrow Biology and Stem Cells" Immunol. Ser. 49, pp. 1-38.
Anklesaria et al. (1989) Blood 74, p. 1144.
Anklesaria et al. (1987) Proc. Nat'l Acad. Sci. USA 84, p. 7681.
Bennett et al. (1991) J. Cell Sci. 99, p. 131.
Bentley (1982) Br. J. Haematol 50, p. 1.
Castro-Malaspina et al. (1980) "Characterization of Human Bone Marrow Fibroblast Colony-Forming Cells and Their Progeny" Blood 56, p. 289-301.
Castro-Malaspina et al. (1981) "Human Megakaryocyte Stimulation of Proliferation of Bone Marrow Fibroblasts" Blood 57, p. 781-787.
Clarke, Emer, "Mesenchymal Cells" www.stemcell.com (mini-review).
Dexter et al. (1977) "Conditions Controlling the Proliferation of Haemopoietic Stem Cells in Vitro" J. Cell Physiol. 91, p. 335-344.
Dexter et al. (1984) Kroc Found. Ser. 18, pp. 57-96.
Fong et al. (1987) "Nonradioactive, Agarose Minigel Procedure for Telomeric Repeat Amplification Protocol" BioTechniques 23, p. 1029-1032.
Friedenstein (1976) Int'l R. Cytology 47, p. 327.
Friedenstein (1980) "Stromal Mechanisms of Bone Marrow: Cloning in Vitro and Retransplantation in Vivo" Immunology of Bone Marrow Transplantation, pp. 19-29.
Friedenstein et al. (1970) Cell Tissue Kinetics 3, p. 393.
Friedenstein et al. (1992) Bone and Mineral 18, p. 199.
Gronthos, S., et al. (2003) J. Cell Sci. 116, pp. 1827-1835.
Gronthos, S., et al. (1994) The STRO-1+ Fraction of Adult Human Bone Marrow Contains the Osteogenic Precursors, Blood 84, pp. 4164-4173.
Gronthos, S., et al. (1995) Blood 85, p. 929.
Hellstrom et al. (1999) Development 126, p. 2047.
Huang and Terstappen (1992) Nature 360, p. 745.
Keating et al. (1982) Nature 298, p. 280.
Kim et al. (1994) Science 266, p. 2011.
Knopse et al. (1966) Blood 28, p. 398.
Knopse et al. (1972) Blood 39, p. 331.
Lichtman (1981) Experimental Hematology 9, p. 391.
Long (1992) Experimental Hematology 20, p. 288.
MacManus and Weiss (1984) Blood 64, p. 1036.
McIntyre and Bjornson (1986) Exp. Hematol. 14, p. 833.
Miltenyi et al. (1990) Cytometry 11, p. 231.
Owen (1985) Bone and Mineral Research 3, p. 1.
Owen and Friedenstein (1988) CIBA Found. Symposium 136, p. 42.
Perkins and Fleischman (1990) Blood 75, p. 620.
Piersma et al. (1983) Br. J. Haematol. 54, p. 285.
Rothstein et al. (1985) Blood 65, p. 744.
Simmons, P.J., et al. (1994) "Isolation, Characterization and Functional Activity of Human Marrow Stromal Progenitors in Hemopoiesis" Advances in Bone Marrow Purging and Processing: Fourth Int'l Symposium 389, pp. 271-280.
Simmons et al. (1987) Nature 328, p. 429.
Simmons and Torok-Storb (1991) Blood 78, p. 55.
Simmons and Torok-Storb (1991) Blood 78, p. 2848.
Tavassoli and Friedenstein (1983) Ann. J. Hematol. 15, p. 195.
Tavassoli and Crosby (1968) Science 161, p. 54.
Testa et al. (1988) "Long-Term Bone Marrow Damage After Cytotoxic Treatment: Stem Cells and Microenvironment in Hematopoiesis: Long-Term Effects of Chemotherapy and Radiation" Hematol. 8, pp. 75-92.
Van Vlasselaer et al. (1994) Blood 84, p. 753.
Waller et al. (1995) Blood 85, p. 2422.
Weiss (1976) Anatomical Record 186, p. 161.
Zoltowska et al. (2001) Arch. Immunol. Ther. Exp. (Warsz) 49, pp. 59-61.
International Search Report issued by the International Searching Authority (ISA/AU) on Aug. 22, 2005 in connection with International Application No. PCT/AU2005/000953.
International Search Report issued by the International Searching Authority (ISA/AU) on Nov. 25, 2005 in connection with International Application No. PCT/AU2005/001445.
U.S. Appl. No. 11/663,570, filed Mar. 23, 2007.
U.S. Appl. No. 11/663,563, filed Mar. 23, 2007.
PCT International Publication No. WO 1999/003973 A, Osiris Therapeutics Inc., published Jan. 28, 1999.
PCT International Publication No. WO 04/84921 A1, published Oct. 7, 2004 (Medvet Science Pty Ltd and Angioblast Systems Incorporated).
PCT International Publication No. WO 04/85630 A1 published Oct. 7, 2004 (Medvet Science Pty Ltd and Angioblast Systems Incorporated).
Office Action issued Jan. 8, 2008 in connection with U.S. Appl. No. 11/326,736.
Office Action issued Jan. 8, 2008 in connection with U.S. Appl. No. 10/551,162.
Office Action issued Aug. 25, 2006 in connection with U.S. Appl. No. 10/955,709.
Office Action issued Aug. 24, 2007 in connection with U.S. Appl. No. 11/178,920.
Office Action issued Dec. 15, 2006 in connection with U.S. Appl. No. 11/178,920.
Office Action issued Jul. 10, 2006 in connection with U.S. Appl. No. 11/178,920.
Office Action issued Jan. 22, 2007 in connection with U.S. Appl. No. 11/169,875.
Shi S et al: "Perivascular niche of postnatal mesenchymal stem cells in human bone marrow and dental pulp." Journal of Bone and Mineral Research, vol. 17, No. Suppl 1, Sep. 2002. p. S446, XP009083412 & Twenty-Fourth Annual meeting of the American Society for Bone and Mineral Research; San Antonio, Texas, USA; Sep. 20-24, 2002.
Gronthos S et al: "Postnatal human dental pulp stem cells (DPSCs) in vitro and in vivo." Proceedings of the National Academy of Sciences of USA, National Academy of Science, Washington, DC, US, vol. 97, No. 25, Dec. 5, 2000, pp. 13625-13630.
Shi S et al: "Perivascular niche of postnatal mesenchymal stem cells in human bone marrow and dental pulp." Journal of Bone and Mineral Research, New York, NY, US, vol. 18, No. 4, Apr. 2003, p. 696-704.
Tse H F et al: "Angiogenesis in ischaemic myocardium by intramyocardial autologous bone marrow mononuclear cell implantation." Lancet The, Lancet Limited, London, GB, vol. 361, No. 9351, Jan. 4, 2003, pp. 47-49.
Zvaifler, et al.; (2000) "Mesenchymal precursor cells in the blood of normal individuals," Arthritis Research and Therapy, 2: 477-488.
Ji, et al., (2004) "Interactions of Chemokines and Chemokine Receptors Mediate the Migration of Mesenchymal Stem Cells to the Impaired Site in the Brain After Hypoglossal Nerve Injury," Stem Cells, 22: 415-427.
Sordi, et al., (2005) "Bone marrow mesenchymal stem cells express a restricted set of functionally active chemokine receptors capable of promoting migration to pancreatic islets," Blood, 106(2): 419-427.
Wynn, et al., (2004) "A small proportion of mesenchymal stem cells strongly expresses functionally active CXCR4 receptor capable of promoting migration to bone marrow," Blood, 104(9): 2643-2645.
Kortesidis, et al., (2005) "Stromal-derived factor-1 promotes the growth, survival, and development of human bone marrow stromal stem cells," Blood, 105(10): 3793-3801.
Gronthos, S., et al., (1999) "Differential Cell Surface Expression of The STRO-1 And Alkaline Phosphatase Antigens On Discrete Developmental Stages In Primary Culture Of Human Bone Cells," Journal of Bone and Mineral Research, 14 (1) : 47-56.
Stewart, K., et al., (1999) "Further Characterization Of Cells Expressing STRO-1 In Cultures Of Adult Human Bone Marrow Stromal Cells," Journal of Bone and Mineral Research, 14 (8) : 1345-1356.
Supplementary European Search Report from European Patent Office, Application No. EP 04 72 3935, May 10, 2007.
Supplementary European Search Report from European Patent Office, Application No. EP 04 72 3937, May 25, 2007.
Internatioinal Search Report issued by the International Searching Authority (ISA/AU) on May 17, 2004 in conneciton with International Application No. PCT/AU2004/000416.

International Preliminary Report on Patentability issued May 17, 2004 in connection with International Application No. PCT/AU2004/000416.

International Publication No. WO 2001/004268 A1, Medvet Science Pty Ltd, published Jan. 18, 2001.

International Search Report issued by the International Searching Authority (ISA/AU) on May 17, 2004 in connection with International Application No. PCT/AU2004/000417.

International Preliminary Report on Patentability issued by the International Bureau of WIPO on Oct. 1, 2005 in connection with International Application No. PCT/AU2004/000417.

Barry, M. (2003) "Biology and Clinical Applications . . . Stem Cells." Birth Defect Research (Part C) 69:250-256.

Cassiede, P. et al. (1996) "Osteochondrogenic Potential of Marrow Mesenchymal Progenitor Cells Exposed to . . ." Journal of Bone and Mineral Research vol. 11(9):1264-1273.

Chopp, M. and Li, Y. (2002) "Treatment of Neural Injury with Marrow Stromal Cells." The Lancet Neurology 1:92-100.

Dennis Je, et al. (2002), "The STRO-1+ Marrow Cell Population is Multipotential," Cells Tissues Organs, 170:73-82.

Finney, M.R. et al. (2006), "Direct Comparison of Umbilical Cord Blood versus Bone Marrow-Derived Endothelial Precursor . . . ," Biol. Blood and Marrow Transplant. 12:585-593.

Fujii, S. et al. (2008), "Investigating a Clonal Human Periodontal Ligament Progenitor/Stem Cell Line in Vitro and in Vivo," J. Cell. Physiol. 215:743-749.

Greenberger, J. and Keating, A. (1996) "The Hematopoietic Microenvironment." Keystone Symposium, Taos, New Mexico 14:366-367.

Gronthos et al. (1996) "The Biology and and Application of Human Bone Marrow Stromal Cell Precursors." Journal of Hematotherapy 5(1): 15-23 (Abstract).

Hoerstrup SP et al. (2002), "Tissue Engineering of Functional Trileaflet Heart Valves from Human Marrow Stromal Cells." Circulation 106(Suppl):1-143-150.

Kang Yong Jung et al. (2004) "Involvement of PI-3-kinase, JNK, PKC, and PKA in the PDGF-induced . . . mesenchymal stem cells." vol. 18(8) C253.

Kassem, M. (2004) "Mesenchymal Stem Cells: Biological Characteristics and Potential Clinical Applications." Cloning Stem Cells 6:369-374.

Le Blanc, K. and Ringden, 0. (2005) "Immunobiology of Human Mesenchymal Stem Cells and Future Use in Hematopoietic . . ." Biology of Blood and Marrow Transplantation 11:321-33.

Murray et al. (1996) "Fetal Bone Marrow CD34+CD41+ Cells are Enriched for Multipotent Hematopoietic Progenitors . . ." Exp. Hematol. 24:236-245.

Pan, Beiqing et al. (2004) "The nitrogen-containing bisphosphonate, zaledronic acid, increases mineralisation of human bone-derived cells in vitro." Bone 34:112-123.

Summer, R. and Fine, A. (2008) "Mesenchymal Progenitor Cell Research: Limitations and Recommendations," Proc. Am. Thorac. Soc. 5:707-710.

Yang XV, et al. (2006), "Evaluation of Human Bone Marrow Stromal Cell Growth on Biodegradable . . . ," Biochemical and Biophysical Research Communications 342:1098-1107.

International Preliminary Report on Patentability . . . International Bureau of WIPO on Oct. 1, 2005 in connection with International Application No. PCT/AU2004/000416.

Extended European Search Report issued Dec. 27, 2007 in connection with European Application No. 05787106.3.

Supplementary European Search Report issued Jan. 2, 2008 in connection with European Application No. 05754008.0.

Nov. 13, 2007 Office Action issued in connection with U.S. Appl. No. 11/169,875.

Jan. 8, 2008 Office Action issued in connection with U.S. Appl. No. 11/326,736.

Jan. 8, 2008 Office Action issued in connection with U.S. Appl. No. 10/551,162.

Jan. 10, 2008 Final Office Action issued in connection with U.S. Appl. No. 10/955,709.

Apr. 4, 2008 Restriction Requirement issued in connection with U.S. Appl. No. 10/551,326.

Sep. 12, 2008 Office Action issued in connection with U.S. Appl. No. 10/551,162.

Oct. 16, 2008 Office Action issued in connection with U.S. Appl. No. 10/955,709.

Nov. 13, 2008 Office Action issued in connection with U.S. Appl. No. 10/551,326.

Nov. 17, 2008 Office Action issued in connection with U.S. Appl. No. 11/326,736.

Nov. 26, 2008 Office Action issued in connection with U.S. Appl. No. 11/169,875.

Jun. 22, 2009 Final Office Action issued in connection with U.S. Appl. No. 10/551,162.

Jun. 23, 2009 Final Office Action issued in connection with U.S. Appl. No. 11/169,875.

Jul. 16, 2009 Final Office Action issued in connection with U.S. Appl. No. 10/955,709.

* cited by examiner

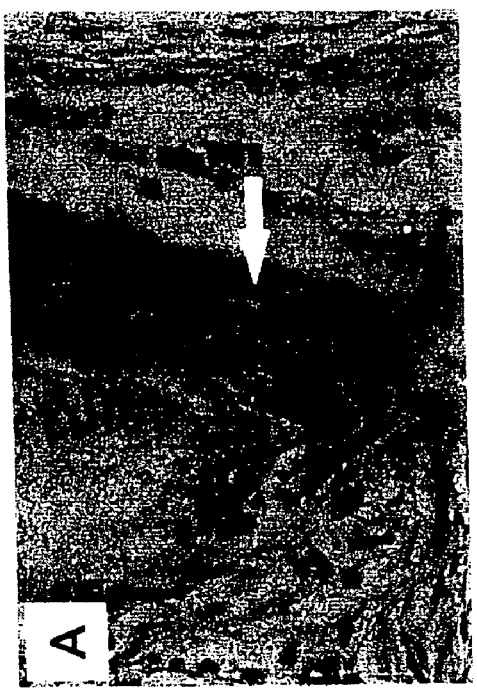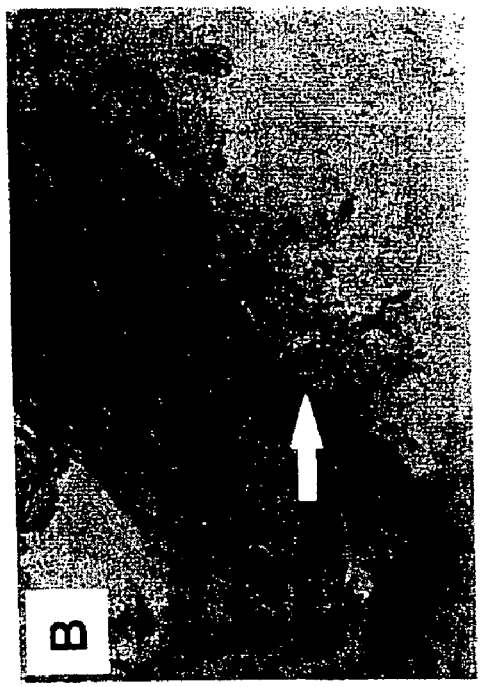
FIGURE 8

Spleen
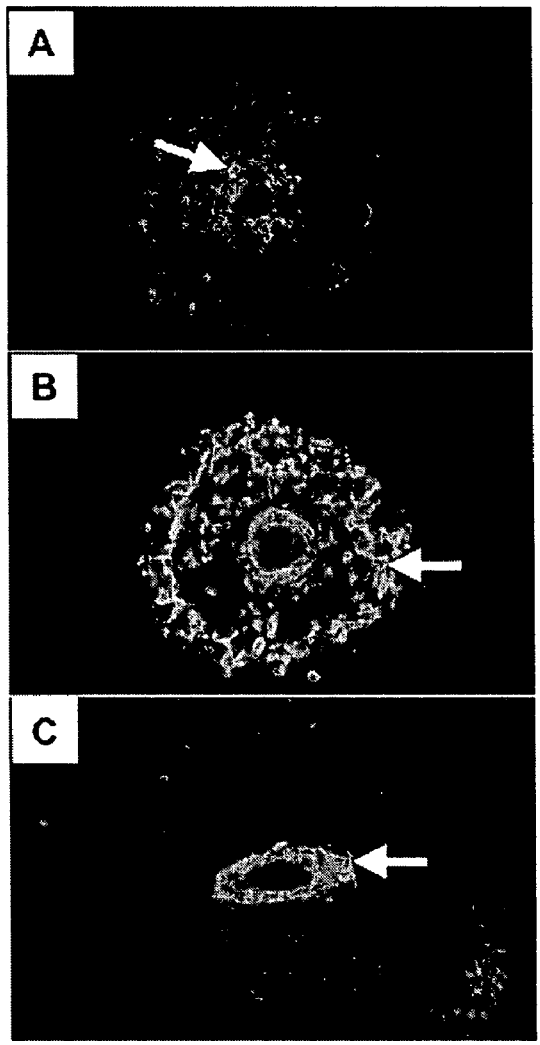
Pancreas
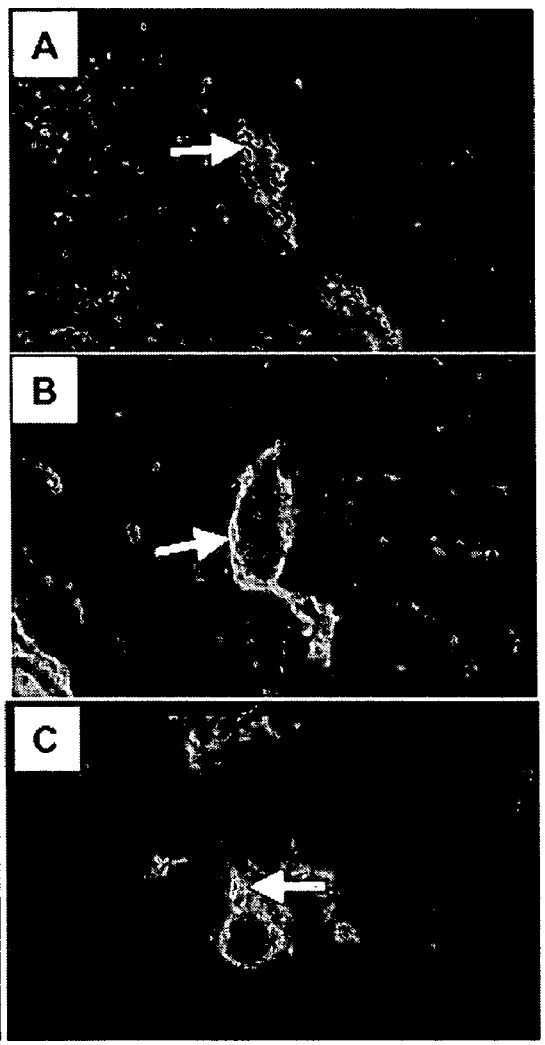
FIGURE 17 PANEL 1

Brain
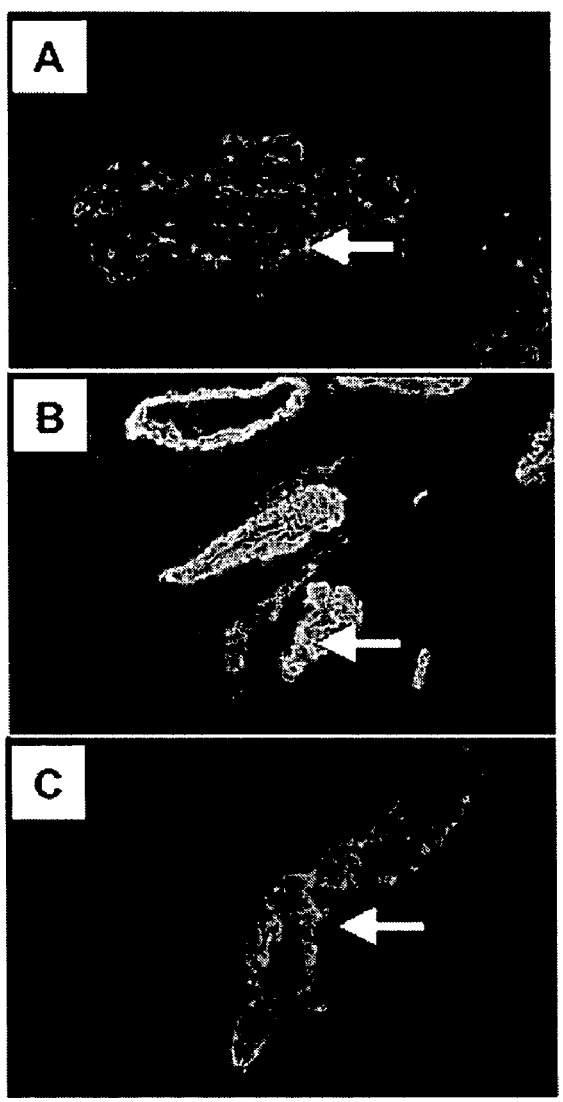
Kidney
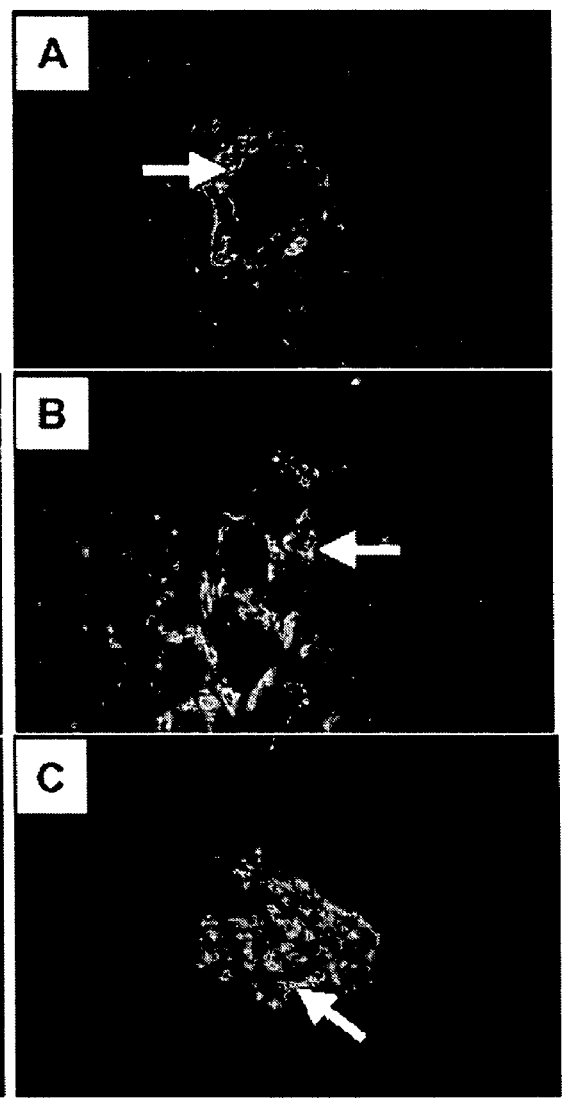
FIGURE 17 PANEL 2

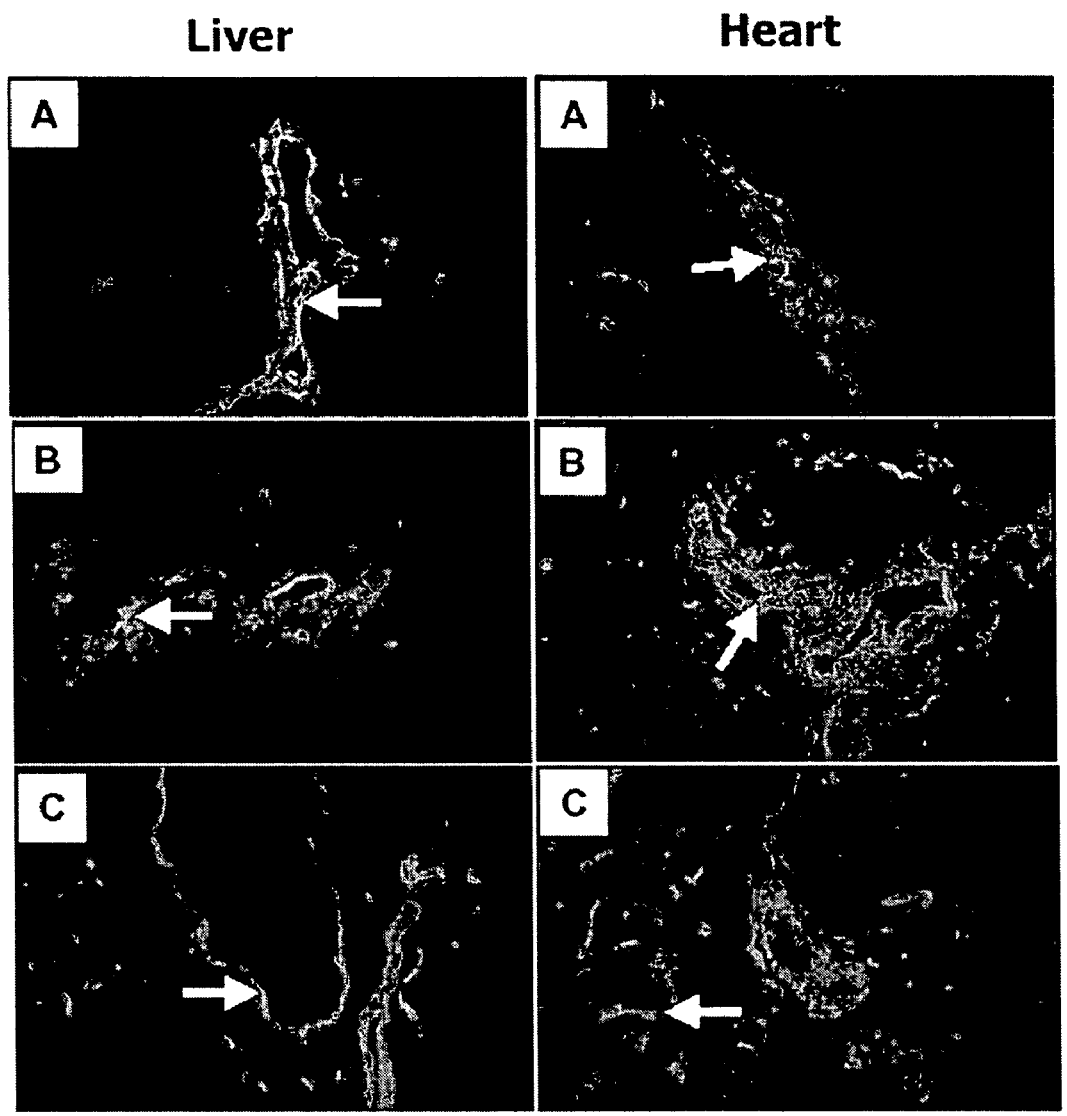
FIGURE 17 PANEL 3

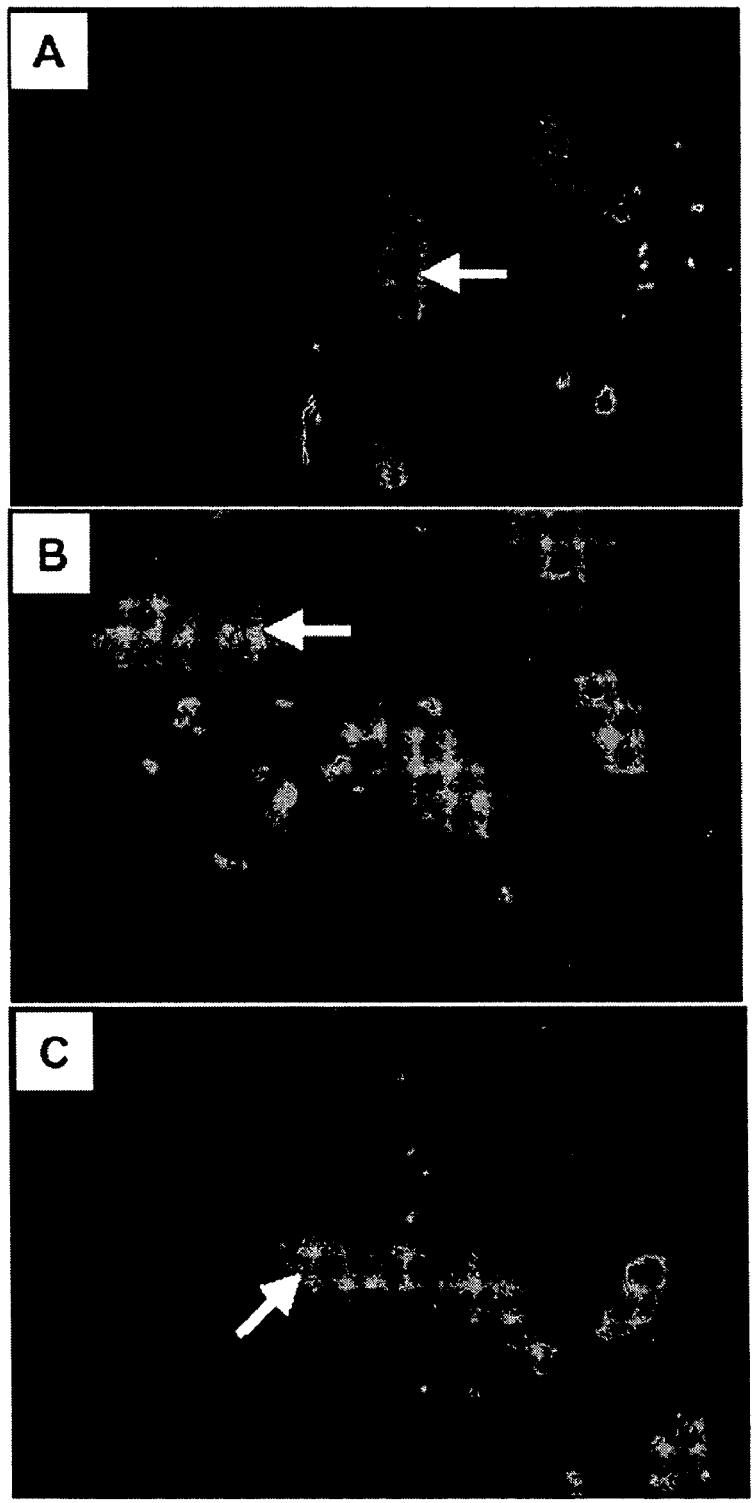
FIGURE 17 PANEL 4

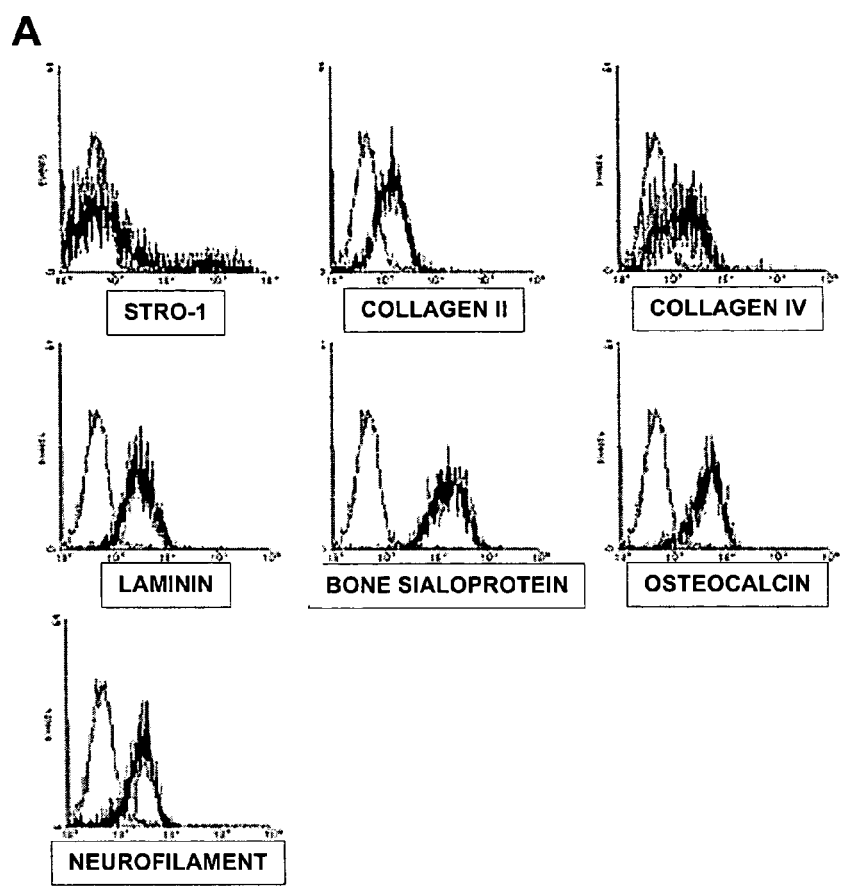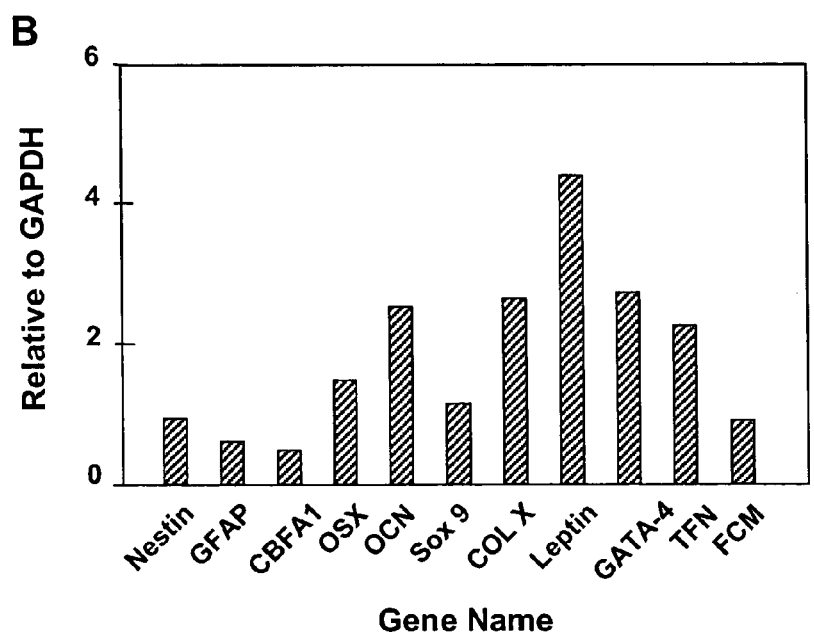
Figure 24

MESENCHYMAL PRECURSOR CELL

CROSS REFERENCE TO RELATED APPLICATION

This application is a continuation-in-part of U.S. Ser. No. 10/030,411, filed Apr. 11, 2002, now U.S. Pat. No. 7,122,178, issued Oct. 17, 2006, which is a Section 371 national stage of PCT International Application No. PCT/AU00/00822 filed Jul. 7, 2000, which claims priority of Australian Patent Application No. PQ 1477, filed Jul. 7, 1999.

This invention relates to the enrichment of mesenchymal precursor cells using a combination of cell surface markers, and to a cell population of mesenchymal precursor cells.

Mesenchymal cells are derived from a number of tissues and act as the supportive structure for other cell types. Bone marrow for instance is made of both haematopoietic and mesenchymal derived cells. The mesenchymal cells include endothelial cells that form the sinuses and advetitial reticular cells that have characteristics consistent with adipocytes, fibroblasts and muscle cells.

It is believed that certain mesenchymal precursor cells (MPCs) are responsible for the formation of mesenchymal cells. In the bone MPCs are the formative pluripotent blast cells that are believed to be capable of differentiating into any of the specific types of connective tissues (ie. the tissue of the body that support the specialised elements, particularly adipose, areolar, osseous, cartilaginous, elastic and fibrous connective tissues) depending upon the various environmental influences.

Purification or at least enrichment of MPCs is desirable for a variety of therapeutic reasons. The reasons include regeneration of missing or damaged skeletal tissue, enhancing the implantation of various plastic or metal prosthetic devices through the attachment of the isolated and culturally expanded marrow derived mesenchymal cells onto the porous surfaces of the prosthetic devices, which upon activation and subsequent differentiation of marrow-derived mesenchymal cells produce natural osseous bridges.

Composite grafts of cultured mesenchymal cells might be used to augment the rate of haematopoietic cell reserve during bone marrow transplantation.

A class of defects that may be repaired by cultured marrow-derived mesenchymal cells expanded from the MPCs of the present invention is the class of large skeletal defects in bone caused by injury or produced by the removal of large sections of bone infected with tumour. Under normal circumstances this type of defect does not heal and creates nonunion of the bone. This type of defect may be treated by implanting cultured mesenchymal cells contained in calcium phosphate ceramic vehicles into the defect site.

A second class of defect that may be repaired by cultured marrow-derived mesenchymal cells expanded from the MPCs of the present invention, is the damaged articular cartilage generated by trauma or by diseases such as osteoarthritis and rheumatoid arthritis. Under normal circumstances, damage to articular cartilage does not heal except in very young individuals where the underlying bone is also damaged so that a bloody wound is created. It is projected by the present invention that this type of defect can be treated by implanting cultured marrow derived mesenchymal cells into the defect. The cells will be formatted in carriers which will hold the cells in the defect and present them in a manner (round cell morphology) that they differentiate into chondrocytes.

It is not clearly understood why composite grafts of cultured mesenchymal cells and ceramic induce recruitment of haematopoietic stem cells and other marrow elements, however, the fact that this does occur allows for the use of these grafts in a way to sequester haematopoietic stem cells and generate a haematopoietic stem cell reservoir. The reservoir of haematopoietic stem cells can then be used in clinical applications such as marrow transplantation as an alternative method for harvesting haematopoietic stem cells.

Another potential use for purified cells is as a means of gene therapy, by the introduction of exogenous nucleic acids for the expression of therapeutic substances in the bone marrow—see U.S. Pat. No. 5,591,625 by Gerson et al.

A purified source of MPCs is desirable for a number of reasons. One major reason is that if there is a mixed population, MPCs will respond to signals elicited by other cells to behave in a manner that might not be desired. Thus, for example, a contaminating cell might express a cytokine that evokes differentiation into adipose tissue, whereas one may require the cells for bone formation, in which case the usefulness of the MPCs is somewhat limited. Additionally for a reason similar to that given above, purified progenitor cells tend to be easier to handle and manage than less purified cells.

There have been many attempts at purifying or significantly enriching MPCs, however significant enrichment has until the present invention not been achieved. In contrast to the haemopoietic system, in which stem cells can be physically separated based upon differences in their expression of cell surface markers, the cell surface antigenic phenotype of MPCs remains relatively poorly defined. A further problem of purification of MPCs is a result of the physical association between mesenchymal cells and other cell types.

The bone and bone marrow (BM) tissues contain a phenotypically diverse population of stromal cell lineages that are currently thought to arise from a rare and primitive population of multi-potential mesenchymal precursor cells (MPC) [Owen, 1985; Owen and Friedenstein, 1988]. Bone marrow MPC can be readily measured by their ability to form adherent clonogenic clusters composed of fibroblastic-like cells (CFU-F: colony-forming-unit-fibroblast) in short-term liquid culture [Friedenstein et al, 1970; Castro-Malaspina et al, 1980]. In vitro studies have documented variations in the morphology and proliferative capacity of different BM MPC clones [Friedenstein et al, 1970; 1976; Castro-Malaspina et al, 1980; Owen et al, 1987; Bennett et al, 1991; Simmons and Gronthos, 1991]. The heterogeneous nature of the BM MPC population was further demonstrated in studies where culture expanded MPC clones displayed different developmental potentials in the presence of glucocorticoids or when transferred into ectopic sites in vivo [Friedenstein et al, 1980; Owen et al, 1987; Bennett et al, 1991]. Collectively, these studies support the concept of a stromal cell hierarchy of cellular differentiation by analogy with the haemopoietic system.

Given the extensive literature regarding the characterisation of haematopoietic stem cells and their progeny there has been little progress towards the identification of the various elements which constitute the bone marrow stromal precursor compartment. This is due in part to the low incidence of MPC in aspirates of marrow (0.05% to 0.001%) [Castro-Malaspina et al 1980; Simmons and Torok-Storb, 1991a; 1991b; Falla et al, 1993; Waller et al, 1995a], and because of the paucity of antibody reagents that allow for the precise identification and isolation of the MPC population. Stromal precursor cells have been partially enriched from bone marrow aspirates through their binding to different lectins such as soya bean agglutinin and wheat germ agglutinin or by using a negative immunoselection process based on their lack of expression of various cell surface antigens restricted to the myeloid, erythroid and lymphoid cell lineages [Simmons and Torok-Storb 1991a; 1991b; Simmons et al, 1994; Rickard et al, 1996]. However, the inefficiency of these selection strategies has resulted in the presence of contaminating populations of accessory cells and haemopoietic progenitor cells. Moreover, a major difficulty in using techniques such as fluorescense activated cell sorting (FACS) to positively select for pure populations of MPC is that they share many common antigens with HSC including early developmental markers such as the human CD34 antigen and the murine stem cell antigen-1.

Recent advances in the study of human stromal stem cell biology have been attributed to the development of novel monoclonal antibodies (Mabs) which recognise antigens on BM MPC that are correspondingly not reactive with haemopoietic progenitors. We have previously described a monoclonal antibody, STRO-1 which identifies an as yet unidentified 60 kDa cell surface antigen expressed on all assayable MPC in aspirates of adult human BM [Simmons and Torok-Storb, 1991a]. The majority of the STRO-1$^+$ bone marrow mononuclear cells (BMMNC) (approximately 90%) have been identified as late stage glycophorin A$^+$ erythroblasts. The MPC population are restricted to the minor population of STRO-1$^+$ cells which lack glycophorin A [Simmons and Torok-Storb, 1991a]. Importantly, STRO-1 demonstrates no detectable binding to haemopoietic progenitors (CFU-GM, BFU-E, BFU-Meg, CFU-GEMM) nor to their precursors (pre-CFU) [Simmons and Torok- Storb, 1991a; Gronthos and Simmons, unpublished observations].

A systematic examination of the immunophenotype of MPC derived from adult human BM has previously been performed using two-color FACS analysis [Simmons et al, 1994]. A number of antigens were shown to be coexpressed with STRO-1 by essentially all BM MPC. These included the endopeptidases CD10 and CD13 and the adhesion molecules Thy-1 (CDw90), VCAM-1 (CD106) and various members of the β1 (CD29) integrin family [Simmons et al, 1994]. This is in accord with the data of Terstappen and colleagues regarding the antigenic phenotype of human foetal BM MPC [Waller et al, 1995].

SUMMARY OF THE INVENTION

This invention arises from the finding that enrichment of mesenchymal precursor cells is greatly enhanced by the use of two markers specific for mesenchymal cells, that can be used to recognise early cells. To this end it will be appreciated that MPCs are early cells that are substantially at a pre-expansion stage of development and hence are precursors to mesenchymal stem cells in which a significant number of the population have expanded and are therefore incapable of further expansion. Thus, MPCs are cells that have yet to differentiate to fully committed mesenchymal cells. These cells need not however be stem cells in a strict sense, in that they are necessarily able to differentiate into all types of mesenchymal cells. There is a benefit in having an enriched pool of MPCs that are able to differentiate into bone forming cells only, in that these precursor cells have a greater proliferation potential. In particular in accordance with the present invention because the proportions of MPCs in the harvested population is large, the extent to which the population can be expanded is greatly enhanced. Additionally according to aspects of this invention it has been discovered that MPCs are present in the perivascular compartment and are able to be purified from a range of tissues.

Aspects of the present invention provides an enrichment several orders of magnitude better than the best method known to the inventors before the present invention. The inventors have shown that an enriched population in which up to 50% of the MPCs can form colonies of ten or more cells can be achieved using the present invention. In contrast, the citations indicate that the best method known up until now has only achieved an enrichment of up to 0.01% cells capable of forming colonies. It is to be noted that as discussed herein the presence of MPCs is based upon their colonigenic capacity, as determined by the presence of colonies of ten or more cells in liquid culture seeded with single cells after having been grown for 14 days.

In a broad form of a first aspect the invention could be said to reside in a method of enriching mesenchymal precursor cells (MPCs) the method including the steps of enriching for cells based on at least two markers, said markers being either the presence of, or expression levels of markers specific for mesenchymal precursor cells on the one hand, or absence of marker or levels of expression specific for differentiated mesenchymal cells on the other hand.

The preferred source of material for enrichment is bone marrow, and thus in a one form the method is limited to the enrichment of bone marrow derived mesenchymal stem cells. It is also likely that the method of this first aspect of the invention might be used to enrich stromal stem cells from other sources such as blood, epidermis and hair follicles. It is proposed that mesenchymal precursor cells isolated from, for example, skin should have the same potential as those cells isolated from bone marrow. An advantage in isolating cells from skin is that the harvesting is far less invasive than the harvesting of a sample of bone marrow.

It is anticipated that a proportion of the population purified will be stem cells, however, it is not yet known how to separate these stem cells from the MPC population. It has been observed however that a subpopulation has a much greater capacity to divide than others, and perhaps this subpopulation represents the stem cells. It is estimated that approximately 10 to 20% of the MPCs isolated by the illustrated method of this invention are stem cells.

It is preferred that a significant proportion of the MPCs are capable of differentiation into at least two committed cell types selected from the group including but not limited to adipose, areolar, osseous, cartilaginous, elastic and fibrous connective.

It has been found that it is possible to purify MPCs by the above method to a degree where these cells are present in a purified population of which 50% of the MPCs can form colonies of ten or more cells. Therefore the method may result in a cell population in which at least 1% of the cells are MPCs that are colony forming, preferably at least 5% of the cells are MPCs that are colony forming, more preferably at least 10% of the cells are MPCs that are colony forming, and most preferably at least 40% of the cells are MPCs that are colony forming.

The nearest known purification is that by Pittenger et al. (Science 284; 143-147) where cells had been enriched using a Percoll gradient. These workers were only able to get colony forming units from 0.001-0.01% of cells. The present technique therefore results in a very significant enrichment when compared to these attempts.

The present invention is also to be contrasted to the enriched populations described by Caplan et al. in U.S. Pat. No. 5,837,539 who describes a method for the isolation, purification and culture expansion of mesenchymal stem cells which is said to give compositions having greater than 95% human mesenchymal stem cells. It is to be noted that the figure of 95% relates to populations of expanded mesenchymal stem cells, and is likely to reflect a lower number of colony forming units because the cells are at least partially expanded. Thus, Caplan starts with a population of BM cells comprising about 1 in 1000 MPCs and expands the population and then purifies the at least partially expanded population. In contrast the present invention can result in a population of about 1 in 2 cells that are able to form colonies of at least 10 MSCs.

Preferably the method includes enriching by selecting for the positive expression of at least one marker and more preferably both markers are selected for positive expression. These markers are most conveniently cell surface markers. The markers might be selected from a group of surface markers specific for MPC including but not limited to LFA-3, THY-1, VCAM-1, ICAM-1, PECAM-1, P-selectin, L-selectin, CD49b/CD29, CD49c/CD29, CD49d/CD29, CD29, CD18, CD61, 6-19, thrombomodulin, CD10, CD13, SCF, and the antigen recognised by STRO-1.

Reagents suitable for use in labelling these markers can be found in Table 4.

The marker might be absence of various surface markers indicative of commitment, such as CBFA-1, collagen type II, PPARγ2, glycophorin A.

In one preferred form at least one of the markers is the antigen recognised by STRO-1, and in particular the high level of expression of that antigen.

In another preferred form at least one of the markers is VCAM-1.

In one very specific form the two markers are the antigen recognised by STRO-1 and VCAM-1.

The specificity of the markers used in this process is not absolute. Thus even the most preferred markers occur on cell types other than mesenchymal cells, however their expression on the cell surfaces of other cell types is limited.

It will be understood that recognition of cells carrying the cell surface markers that form the basis of the separation can be effected by a number of different methods, however, all of these methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies may be attached to a solid support to allow for a crude separation. The separation techniques should maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

The method might include the step of making a first partially enriched pool of cells by enriching for the expression of a first of the markers, and then the step of enriching for expression of the second of the markers from the partially enriched pool of cells.

It is preferred that the method comprises a first step being a solid phase sorting step, based on recognition of one or more of the markers. The solid phase sorting step of the illustrated embodiment utilises MACS recognising high level expression of STRO-1. This then gives an enriched pool with greater numbers of cells than if a high accuracy sort was used as a first step. If for example FACS is used first, many of the MPCs are rejected because of their association with other cells. A second sorting step can then follow using an accurate separation method. This second sorting step might involve the use of two or more markers. Thus in the illustrated embodiment two colour FACS is used to recognise high level expression of the antigen recognised by STRO-1 as wells as the expression of VCAM-1. The windows used for sorting in the second step can be more advantageously adjusted because the starting population is already partially enriched.

It will be understood that the invention is not limited to the enrichment of cells by their expression of only two markers and it may be preferred to enrich based on the expression of three or more markers.

The method might also include the harvesting of a source of the stem cells before the first enrichment step, which in the most preferred source comprises the step of harvesting bone marrow cells, using known techniques.

The preferred source of such cells is human, however, it is expected that the invention is also applicable to animals, and these might include domestic animals or animals that might be used for sport.

In a broad form of a second aspect the invention could be said to reside in an enriched population of mesenchymal precursor cells as purified by a method according to the first aspect of the invention.

It has been found that it is possible to purify MPCs to a degree where the purified population contains 50% of these cells that are capable of forming colonies of 10 or more cells.

In a broad form of a third aspect the invention could also be said to reside in a cell population in which at least 1% of the cells are MPCs that are colony forming, preferably at least 5% of the cells are MPCs that are colony forming, more preferably at least 10% of the cells are MPCs that are colony forming, and most preferably at least 40% of the cells are MPCs that are colony forming.

The cells of the enriched population preferably carry at least two markers selected from a group of surface markers specific for mesenchymal precursor cells including LFA-3, THY-1, antigen identified by STRO-1, VCAM-1, ICAM-1, PECAM-1, P-selectin, L-selectin, CD49b/CD29, CD49c/CD29, CD49d/CD29, CD29, CD18, CD61, 6-19, thrombomodulin, CD10, CD13 and SCF. Most preferably the cells carry the antigen identified by STRO-1 and VCAM-1.

It will also be understood that in a fourth aspect the invention encompasses a composition including the purified MPCs or a composition made from the purified MPCs.

The purified population of the second or third aspects of the invention, or the composition of the fourth aspect of the invention might be used in the formation and repair of bones, and as such a combination of MPCs as well as a suitable support may be introduced into a site requiring bone formation. Thus, for example, skeletal defects caused by bone injury or the removal of sections of bone infected with tumour may be repaired by implanting cultured MSCs contained in calcium phosphate ceramic vehicles into the defect site. For appropriate methods and techniques see Caplan et al. in U.S. Pat. Nos. 5,226,914 and 5,837,539, both of which use cruder preparations of stem cells.

In addition, the enriched population or composition may be used to assist in anchoring prosthetic devices. Thus, the surface of a prosthetic device such as those used in hip, knee and shoulder replacement, may be coated with the enriched MPCs prior to implantation. The MPCs may then differentiate into osteogenic cells to thereby speed up the process of bony ingrowth and incorporation of the prosthetic device (see Caplan et al. in U.S. Pat. Nos. 5,226,914 and 5,837,539).

The enriched population or composition might also be used in gene therapy so that, for example, an enriched population may have exogenous nucleic acid transformed into it and then such a population may be introduced into the body of the patient to treat a disease or condition. Alternatively it might be used for the release of therapeutics. For appropriate techniques we refer to U.S. Pat. No. 5,591,625 by Gerson et al. which uses cruder preparations of stem cells.

Alternatively the enriched population or composition may be used to augment bone marrow transplantation, wherein the composition containing purified MSCs can be injected into a patient undergoing marrow transplantation prior to the introduction of the whole marrow. In this way the rate of haemopoiesis may be increased, particularly following radiation or chemotherapy. The composition might also encompass a mixture of MPCs and haemopoietic cells which may be useful in radiotherapy or chemotherapy.

In a first form of a fifth aspect the invention might be said to reside in a method of enriching for mesenchymal precursor cells (MPCs), the method including the step of preparing a single cell suspension from a vascularised source tissue and the step of enriching based on the presence of an early perivascular cell marker.

In a second form of the fifth aspect the invention might be said to reside in a method of enriching for mesenchymal precursor cells, the method including the step of preparing a single cell suspension from a, non-bone marrow, vascularised source tissue and separating the tissue into separate cells and the step of enriching based one of the presence or level of one or more early developmental markers and the absence of one or more surface markers indicative of commitment.

In a third form of the fifth aspect the invention might be said to reside in a method of enriching for mesenchymal precursor cells (MPCs), the method including the step of preparing a single cell suspension from a vascularised source tissue and the step of enriching based on the presence of markers expressed in the vascularized tissue by peri-vascular cells.

In a sixth aspect the invention might be said to reside in an enriched population of cells enriched for mesenchymal precursor cells (MPCs) said MPCs having a phenotype of 3G5, MUC18, VCAM-1, STRO-1$^{bri}$ and α smooth muscle actin.

In a first form of a seventh aspect the invention might be said to reside in an isolated mesenchymal precursor cells (MPCs) said MPCs having a phenotype of 3G5, MUC18, VCAM-1, STRO-1$^{bri}$ and α smooth muscle actin.

In a second form of the seventh aspect the invention might be said to reside in an isolated mammalian cell that is multipotent and that is positive for the surface marker 3G5.

In a third form of the seventh aspect the invention might be said to reside in a mesenchymal precursor cell (MPC), capable of forming a clonogenic colony and differentiating to three or more mesenchymal tissue types, isolated from a tissue of the group comprising, but not limited to, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle, and which is positive for the surface marker STRO-1.

In a fourth form of the seventh aspect the invention might be said to reside in an unexpanded population of cells enriched for mesenchymal precursor cells (MPCs), capable of forming a clonogenic colony and differentiating to three or more mesenchymal tissue types, said MPCs co-expressing the surface markers MUC18/CD146 and alpha-smooth muscle actin.

In an eighth aspect the invention might be said to reside in a differentiated progeny cell arising from the third aspect of the invention preferably wherein the progeny cell is at least an osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell.

Several aspects of present invention relates to mesenychmal precursor cells, in particular those that may be present in the perivascular compartment of vascularised tissue. Such mesenchymal cells may be identified by the presence of the 3G5 surface marker, and perhaps additionally or separately by other early developmental markers such as CD146 (MUC18), VCAM-1 and STRO-1.

Precursor cells are early cells that are substantially at a pre-expansion stage of development. These are cells that have yet to differentiate to fully committed cells, however they need not be stem cells in a strict sense, in that they are necessarily able to differentiate into all types of cells. Partially differentiated precursor cells have a benefit in that they have a greater proliferative potential than stem cells.

The present precursor cells are somewhat differentiated in that they are committed to mesenchymal tissue, as opposed, for example, to haemopoietic tissues. It is evident from the data produced that the MPCs that have been isolated lack markers associated with haemopoietic cells such as CD34, and additionally their differentiation potential does not extend to haemopoietic lines. Additionally they need not necessarily have the potential to differentiate into all mesenchymal cell type, rather, they may be able to differentiate into one, two three or more cell types.

It is anticipated that these precursor cell harvested from the tissues concerned may be useful for regenerating tissue for cells types from which they have been sourced. Thus precursor cells isolated from heart may be reintroduced to regenerate heart tissue, however their potential need not be so limited, precursor cells isolated from one tissue type might be useful for regenerating tissue in another tissue type. The microenvironment in which an undifferentiated cell finds itself is known to exert an influence on the route of differentiation and therefore the reintroduction need not necessarily be tissue specific.

The data presented show that MPCs have been harvested and then re-introduced to produce bone and bone marrow and dentin and pulp respectively, in addition arterioles, cord like structures, have been produced after ex vivo expansion of isolated MPCs.

It is anticipated that a wide range of cells might be produced based on gene expression of markers characteristic for certain cell types. It is thus anticipated that under appropriate culture conditions the range of cell types that can be generated from the perivascular MPCs of the present invention include but are not limited to the following, osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell.

One of the benefits of the finding that MPCs can be isolated from perivascular cells is that this greatly expands the range of source tissues from which MPCs can be isolated or enriched and there is no longer an effective restriction on the source of MPCs to bone marrow. The tissues from which these MPCs have been isolated in the exemplifications of this invention are human bone marrow, dental pulp cells, adipose tissue and skin. In addition in situ staining and histological studies have identified that MPC are present in the perivascular compartment of spleen, pancreas, brain, kidney, liver and heart. Given this wide and diverse range of tissue types where perivascular MPCs are present, it is proposed that MPC will also be present from an even wider range of tissue which may include, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle.

These precursor cells of the present invention are distinguished from other known MPCs in that they are positive for 3G5 or perhaps that they carry another perivascular markers. They can be isolated by enriching for an early developmental surface marker present on perivascular cells, in particular the presence of one or more of CD1 46(MUC 18), VCAM-1 and alternatively or additionally high level expression of the marker recognised by the monoclonal antibody STRO-1. Alternatively or additionally enrichment may be carried out using 3G5.

Markers associated with perivascular cells may also be present on the MPCs, for example alpha smooth muscle actin (αSMA).

Other early developmental markers associated with MPCs may also be present. These may include but are not necessarily limited to the group consisting of THY-1, VCAM-1, ICAM-1, PECAM-1, CD49a/CD49b/CD29, CD49c/CD29, CD49d/CD29, CD29, CD61, integrin beta 5, 6-19, thrombomodulin, CD10, CD13, SCF, STRO-1bri, PDGF-R, EGF-R, IGF1-R, NGF-R, FGF-R, Leptin-R (STRO-2). Positive expression of one or more of these markers may be used in methods of enriching for MPCs from source tissue.

The MPCs of the present invention may also be characterised by the absence of markers present in differentiated tissue, and enrichment may be based on the absence of such markers.

Similarly it is preferred that the enriched cell populations are not of haemopoietic origin and thus it is preferred that these cells are not present. Markers characteristically identified as not present include but are not limited to CD34, CD45 and glycophorin A. Additional other markers for this purpose might include CD20 and CD19 (B lymphocyte markers), CD117 (c-kit oncoprotein) present on hemopoietic stem cells and angioblasts, CD14 (macrophage), CD3 and CD4 (T cells).

It may be desirable to use the relatively quiescent, directly enriched or isolated perivascular MCPs. Alternatively it has been discovered that expansion of the enriched population can be carried out and have the beneficial effect of resulting in much greater numbers of cells. The effect of expansion of the directly enriched pool of cells is, however, that some differentiation of the initial MCPs will occur. Expansion over a 5 week period might result in an increase of $10^3$ fold. Other periods might be chosen to expand the population to between $10^2$ to $10^5$ fold. This potential might be directed by culturing them is media containing cytokines and other factors directing the differentiation to a particular tissue type for example PDGF and VEGF forming smooth muscle alpha cords. These could then be introduce into a tissue with, for example, an insult to assist with repair. Alternatively it may be desired after expansion to re select cells on the basis of an early developmental marker, that might be STRO-1$^{bri}$ to increase the proportion of MPCs in the population.

It is found that an essentially pure population of MCPs is not necessary to provide for formation of differentiated cells to form desired tissue structures. The enriched population may have levels of MCPs of greater than about 0.001, 0.01, 0.02, 0.05, 0.1, 0.2, 0.5 or 1% or higher as a proportion of total cell numbers in the enriched population. This order of enrichment can be achieved by the use of a single marker for selection of the enriched MCP population. This is particularly so where the source tissue has an inherently high level of perivascular MCPs. It is found that considerably more 3G5 pos MCPs are present in certain tissue, for example dental pulp, than in bone marrow. Thus in bone marrow 3G5 positive MPCs constitute about 15% of MPC based on STR1$^{bri}$ colony forming cells, whereas in dental pulp that are found to constitute 65% and greater than 90% in fat and skin tissues. Expansion of the population and then re-enrichment using a single marker counting result in higher levels of MPCs, perhaps levels greater than about 0.1, 0.5, 1, 2, 5 or 10%

Whilst it is considered desirable that a substantial proportion and preferably a majority of precursor cells are perivascular MPCs, it is not considered essential for certain forms of the invention for perivascular MPCs to be the sole precursor cell form.

Other forms of precursors may also be present without unduly interfering with the capacity of the perivascular MPCs to undergo the desired differentiation. Such other forms may include haemopoietic precursors or non-perivascular MPCs, perhaps being negative for 3G5.

Certain forms of the present invention provide perivascular MPCs substantially free of endothelial cells. In that context substantially free might be considered to be less than about 5, 2, 1, or 0.1% endothelial cells. Alternatively the context might be an assessment that the enriched population is von Willebrand Factor negative.

It will be understood that recognition of cells carrying the cell surface markers that form the basis of the separation can be effected by a number of different methods, however, all of these methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies may be attached to a solid support to allow for a crude separation. The separation techniques should maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

It is in the context of these methods that a cell be either negative or positive. The positive cells may either be low(lo) or a hi (bright) expresser depending on the degree to which the marker is present on the cell surface, the terms relate to intensity of fluoresence or other color used in the color sorting process of the cells. The distinction of lo and bri will be understood in the context of the marker used on a particular cell population being sorted.

The method of enriching for perivascular MPCs might include the step of making a first partially enriched pool of cells by enriching for the expression of a first of the markers, and then the step of enriching for expression of the second of the markers from the partially enriched pool of cells.

It is preferred that the method comprises a first step being a solid phase sorting step, based on recognition of one or more of the markers. The solid phase sorting step of the illustrated embodiment utilises MACS recognising high level expression of STRO-1. This then gives an enriched pool with greater numbers of cells than if a high accuracy sort was used as a first step. If for example FACS is used first, many of the precursor cells are rejected because of their association with other cells. A second sorting step can then follow using an accurate separation method. This second sorting step might involve the use of two or more markers. Thus in the illustrated embodiment two colour FACS is used to recognise high level expression of the antigen recognised by STRO-1 as wells as the expression of CD146. The windows used for sorting in the second step can be more advantageously adjusted because the starting population is already partially enriched.

The method of enriching for perivascular MPCs might also include the harvesting of a source of the stem cells before the first enrichment step using known techniques. Thus the tissue will be surgically removed. Cells comprising the source tissue will then be separated into a so called single cells suspension. This separation may be achieved by physical and or enzymic means.

The preferred source of such perivascular MPCs is human, however, it is expected that the invention is also applicable to animals, and these might include agricultural animals such as cows, sheep, pigs and the like, domestic animals such as dogs, laboratory animals such as mice, rats, hamsters, and rabbits or animals that might be used for sport such as horses.

In a further form the invention might be said to reside a method of generation tissue in a mammal comprising the step of enriching a population of precursor cells as in the first aspect of the invention, and introducing the enriched population into the mammal, and allowing the enriched population to generate the tissue in the mammal.

Another potential use for enriched cells of the present invention is as a means of gene therapy, by the introduction of exogenous nucleic acids for expression of therapeutic substances in the tissue types concerned.

In the context of the present invention the term isolated cell may mean that perivascular MPCs comprise at least 30, 40, 50, 60, 70, 80, or 95% of total cells of the population in which they are present.

FIGURE LEGENDS

FIG. 1 The frequency histogram represents the immunofluorescence analysis by FACS of BMMNC isolated by MACS on the basis of STRO-1 (FITC) expression: STRO-$1^{dull}$ cell fraction (A); STRO-$1^{intermediate}$ cell fraction (B); STRO-$1^{bright}$ cell fraction (C); The histogram is based on $10^4$ events collected as list mode data.

Figure 2:
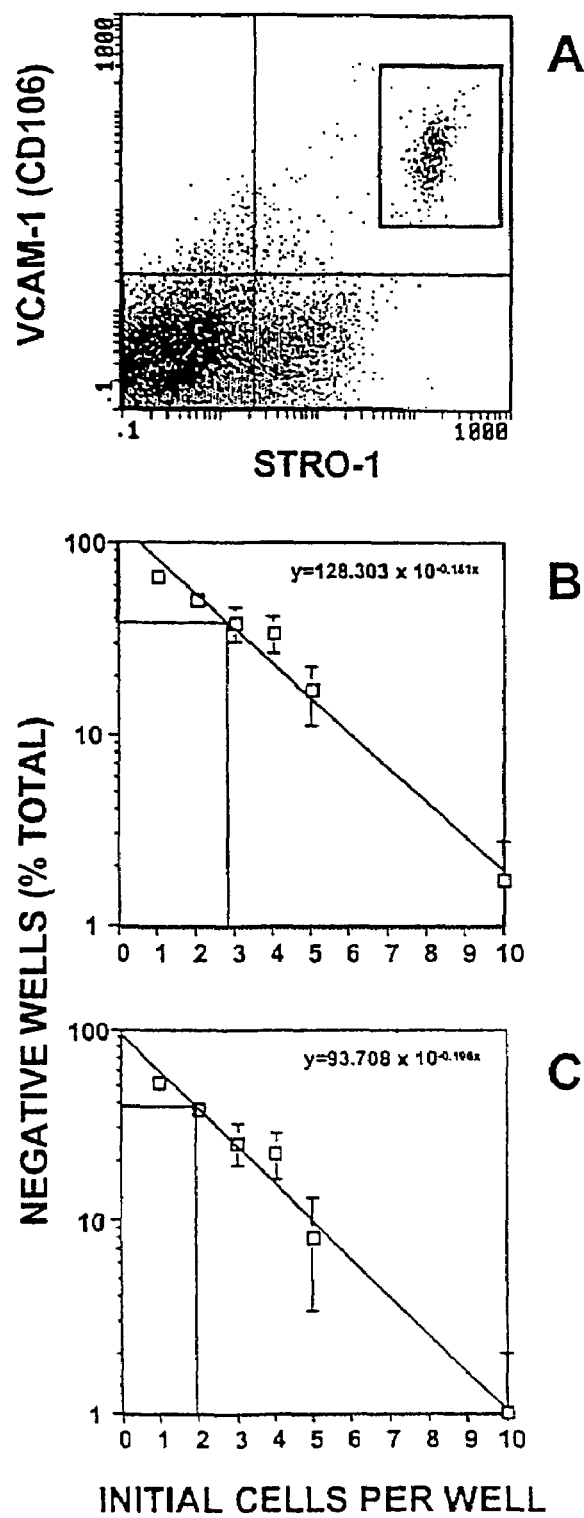

FIG. 2 Dual-colour flow cytometric analysis of VCAM-1 (PE) expression by STRO-$1^+$ (FITC) BMMNC isolated by MACS. The dot plot histogram represents $5 \times 10^4$ events collected as listmode data. STRO-$1^{bright}$/VCAM-$1^+$ cells were sorted by FACS (rectangle), which represented approximately 0.1% of the total BMMNC population (A). The incidence of clonogenic cells (B) colonies (>50 cells) and (C) colonies+clusters (>10<50 cells) based on STRO-$1^{bright}$/VCAM-$1^+$ expression. The frequency of clonogenic cells was determined by limiting dilution analysis (24 replicates per cell concentration) employing Poisson distribution analysis.

Figure 3:
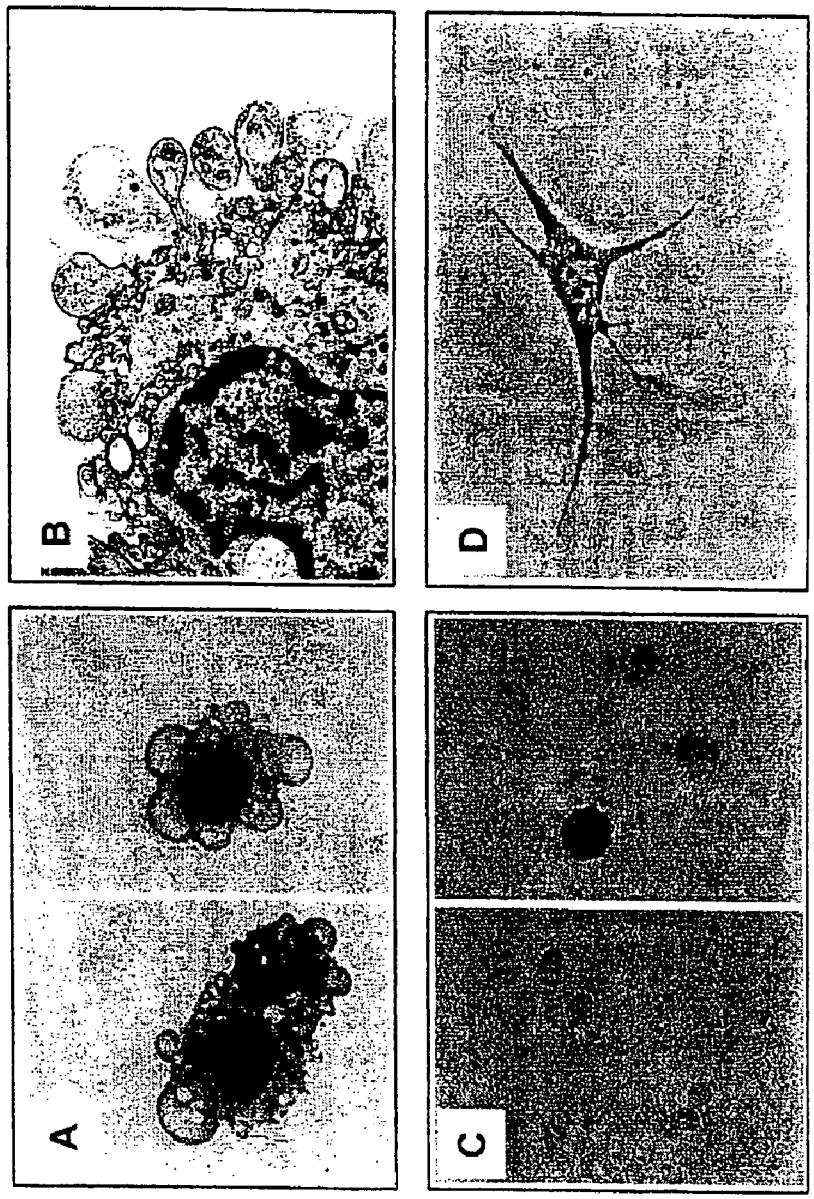

FIG. 3 Characterization of BM MPC. (A) Light microscopic examination of the freshly sorted cells revealed a homogenous population of large cells with heterochromatic nuclei and prominent mucleoli, a granular cytoplasm and numerous blel-like projections of the cell membrane (magnified 40×). (B) Transmission electron micrograph of STRO-$1^{bright}$/VCAM-$1^+$ sorted cells isolated directly from BM (magnified 1000×). (C) Immunohistological staining of cytospin preparations of the sorted STRO-$1^{bright}$/VCAM-$1^+$ BMMNC showing intense staining of most cells with anti-collagen type I antibody, (magnified 40×). (D) Light microscopic view of a purified STRO-$1^{bright}$/VCAM-$1^+$, allowed to adhere to fibronectin-coated culture adopts a stellate, fibroblastoid morphology.

Figure 4:
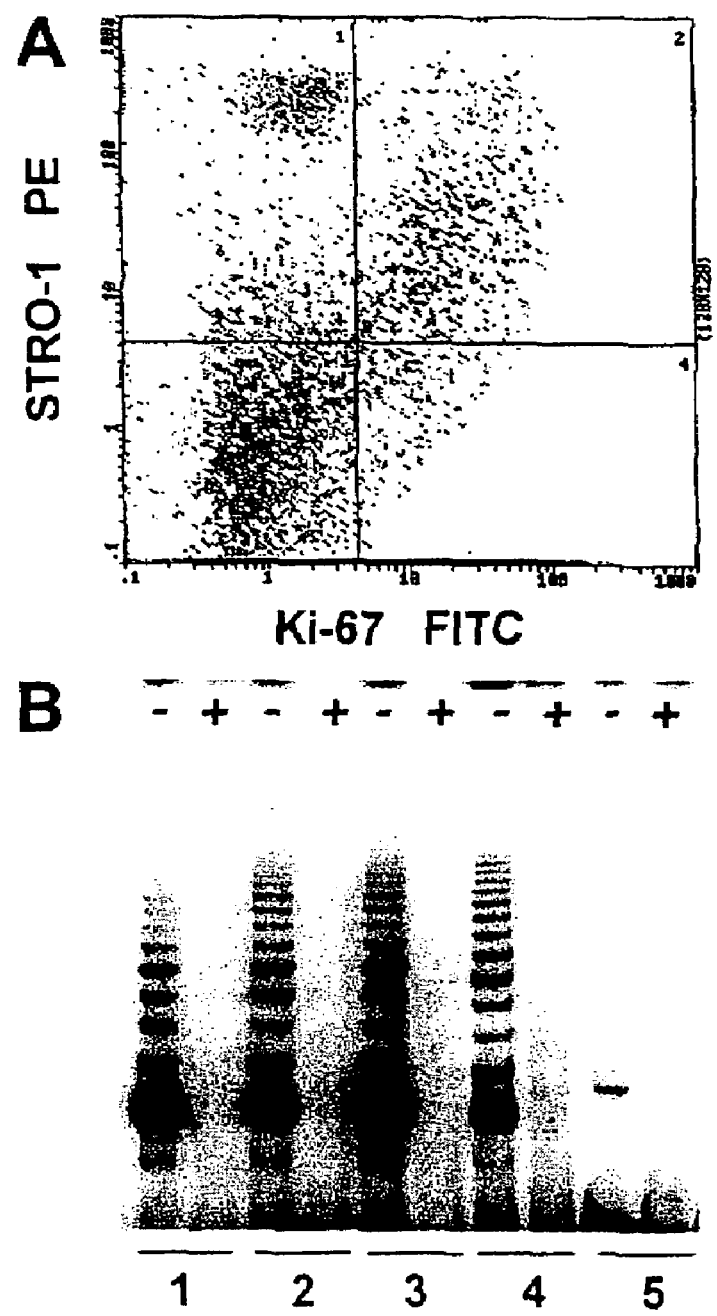

FIG. 4 Characterization of BM MPC. Dual-colour flow cytometric analysis of Ki67 (FITC) expression by STRO-$1^+$ (PE) BMMNC isolated by MACS. The dot plot histogram represents $5 \times 10^4$ events collected as listmode data (B). Telomerase activity in sorted cells populations was examined using a modified TRAP assay (C). TRAP products derived from CHAPS extracts of non-denatured (−) and denatured (+) total bone marrow (lanes 1 and 2), Total STRO-1 [MACS-selected] (lanes 2 and 3). STRO-$1^{bright}$/VCAM-$1^+$ cells sorted fraction (lanes 4 and 5), cultured. STRO-$1^{bright}$/VCAM-$1^+$ cells (lanes 6 and 7) and CD34$^+$-sorted cells TRAP products were resolved on a 12% polyacrylamide gel, stained with SYBR green fluorescent dye, and visualised using a fluorescence scanning system.

Figure 5:
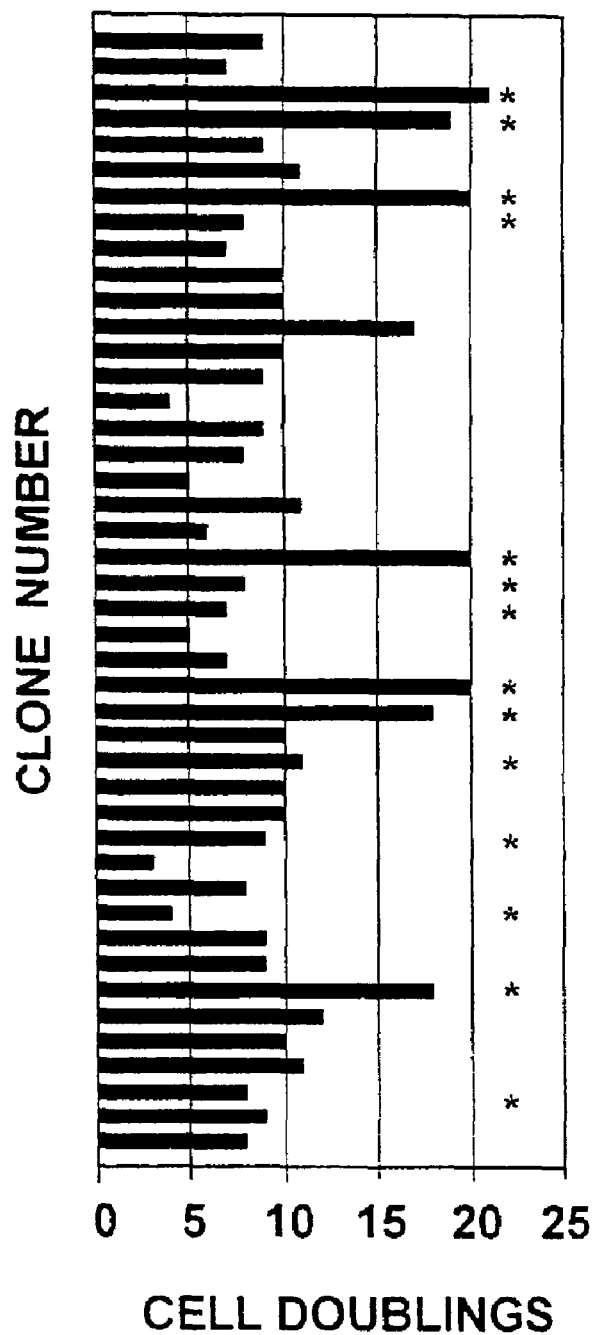

FIG. 5 A total of 44 CFU-F colonies derived from two BM samples were analysed for their cumulative production of cells. A marked variation in proliferative capacity between individual MPC is evident. The majority of clones (36/44; 82%) exhibited only moderate growth potential which did not persist beyond 12 population doublings. 8/44 clones (18%) demonstrated continued growth extending beyond 17 doublings. All clones were switched to adipogenic growth conditions, and under these conditions, 14/44 clones (32%) exhibited adipogenesis.

Figure 6:
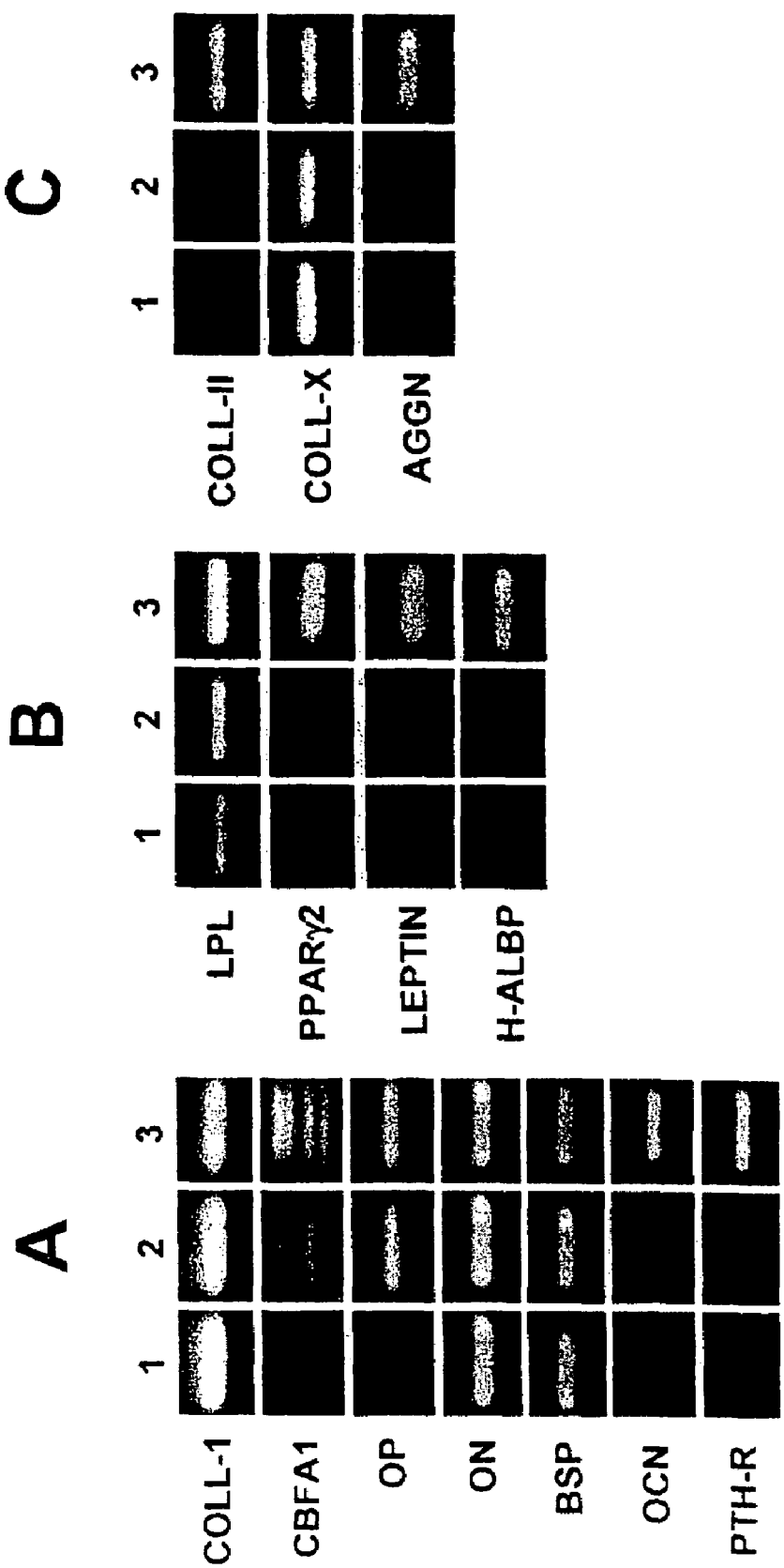

FIG. 6 RT-PCR analysis of gene expression in STRO-$1^{bright}$/VCAM-$1^+$ purified stromal precursor cells (MPC) isolated directly from marrow aspirates, non-induced primary stromal cultures derived from MPC (CFU-F), and CFU-F cultured under osteogenic- (BONE), chondrogenic- (CART) and adipogenic- (FAT) inductive growth conditions. Various markers of: BONE [transcription factor CBFA1; collagen type I (COLL-I); bonesialoprotein (BSP); osteopontin (OP); osteonectin (ON); osteocalcin (OCN), parathyroid hormone receptor (PTHR)]; FAT [lipoprotein lipase (LPL), transcription factor PPARγ2, leptin, human adipocyte lipid binding protein (H-ALBP)]; CARTILAGE [collagen type II (COIL-II), collagen type X (COLL-X), Aggrecam (AGGN)]. Reaction mixes were subjected to electrophoresis on a 1.5% agarose gel and visualised by ethidium bromide staining.

Figure 7:

FIG. 7 In vitro developmental potential of MPC. Primary cultures of derived from STRO-$1^{bright}$/VCAM-1+ BMMNC were cultured for 2 weeks then induced under either osteogenic, adipocytic or chondrocytic conditions for 3-5 weeks. A von Kossa positive mineralised matrix formed throughout the cultures within 4 weeks of bone induction (200×) (A). The presence of clusters of lipid containing adipocytes were also detected by oil red-O staining (200×) (B). Cultures were counter stained with haematoxylin.

FIG. 8 New bone formation in vivo. Immunoselected STRO-$1^{bright}$/VCAM-$1^+$ BMMNC clones, expanded in vitro, were implanted subcutaneously into SCID mice using porous ceramic cubes. Implants were harvested 8 weeks post transplant. New bone formation (solid arrow) was observed for a proportion of clones within the cavities of the ceramic cubes (open arrow) together with surrounding fibrous and hematopoietic tissue (40×) (A). The sections were counter stained with haematoxylin and eosin. A magnified view of new bone formation is shown depicting an osteocyte (arrow) (200×) (B).

Figure 9:
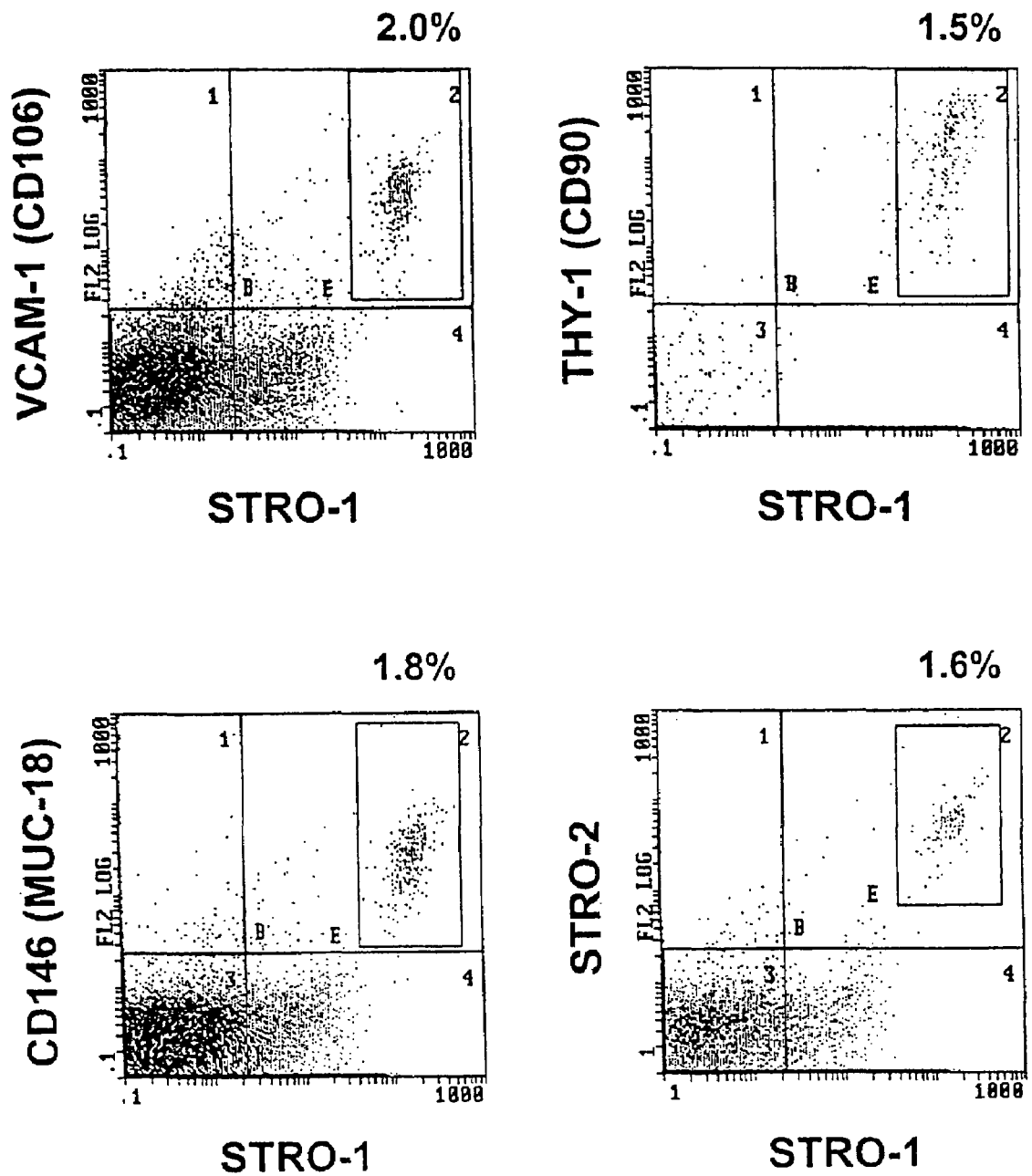

FIG. 9 Dual parameter flow cytometric analysis of STRO-1+ human bone marrow mononuclear cells isolated by MACS. A distinct subpopulation of STRO-1$^{bri}$ cells are identified by VCAM-1, THY-1 (CD90), MUC-18 (CD-146) and STRO-2.

Figure 10:
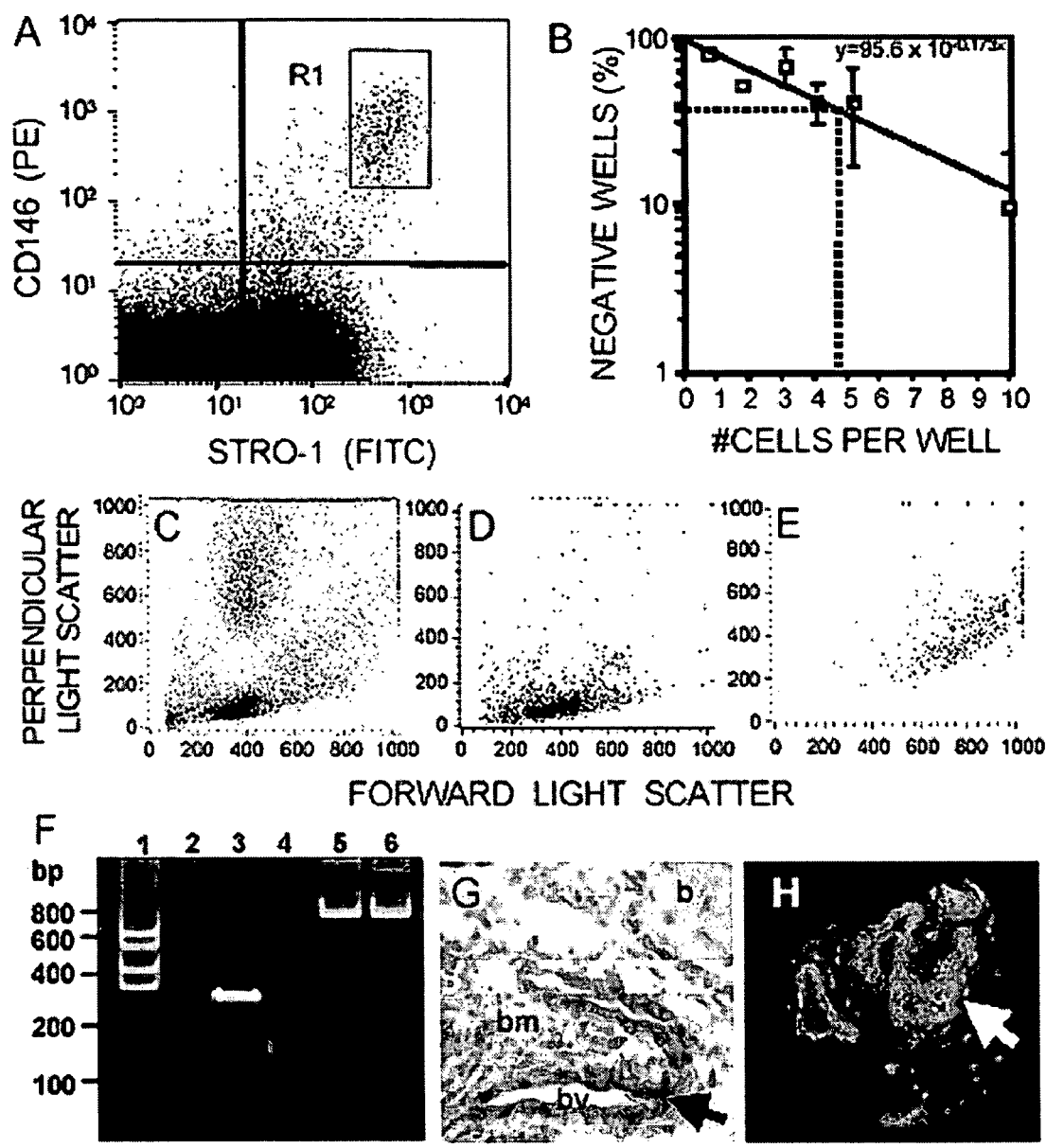

FIG. 10. Properties of STRO-1+ MACS-isolated cells co-labeled with anti-CD146 (CC9). (A) Sort region, R1, represents the double positive STRO-1$^{BRT}$/CD146+ population. (B) The incidence of clonogenic cell colonies (>50 cells) based on STRO-1$^{BRT}$/CD146+ expression was determined by limiting dilution analysis of 24 replicates per cell concentration using Poisson distribution analysis from 5 independent experiments. Forward (size) and perpendicular (granularity) light scatter characteristics of BMMNCs (C), STRO-1$^{int}$/CD146− cells (D) and STRO-1$^{BRT}$/CD146+ cells (E). (F) RT-PCR analysis of STRO-1$^{BRT}$/CD$_{146}$+ sorted marrow cells for CBFA1 (lane 2), osteocalcin (lane 4) and GAPDH (lane 6) transcripts. Control cells (BMSSC cultures grown in the presence of dexamethasone) expressing CBFA1 (lane 1), osteocalcin (lane 3), and GAPDH (lane 5) is also shown. Reaction mixes were subjected to electrophoresis on a 1.5% agarose gel and visualised by ethidium bromide staining. (G) In situ expression of CD146 on blood vessel (bv) walls (arrow) in human bone marrow (bm) sections near the bone (b) surface 20×. Sections were counter stained with Hematoxylin. (H) Dual Immunofluorescence staining demonstrating reactivity of the STRO-1 antibody labeled with Texas red and the CC9 antibody labeled with fluorescein isothiocyanate, reacting to blood vessel walls in frozen sections of human bone marrow.

Figure 11:
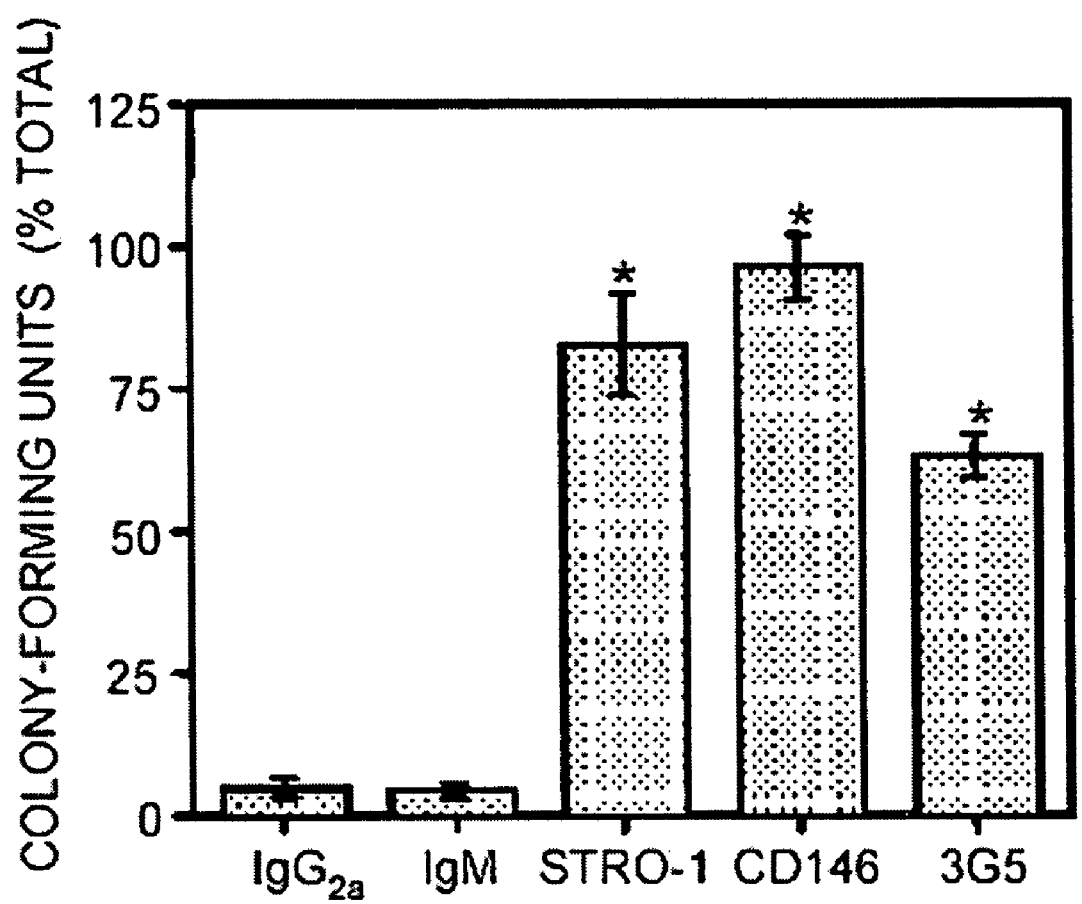

FIG. 11. Immunophenotypic analysis of DPSCs in vivo. The bar graph depicts the number of clonogenic colonies retrieved from single cell suspensions of dental pulp following immunomagnetic bead selection based on reactivity to antibodies that recognize STRO-1, CD146, and 3G5 and isotype-matched negative control antibodies. The data are expressed as the number of colony-forming units obtained in the bead positive cell fractions as a percentage of the total number of colonies in unfractionated pulp cells averaged from three separate experiments. Statistical significance (*) was determined using the student t-test (p 0.01) comparing the percent total number of colonies for each antibody with the corresponding isotype-matched control.

Figure 12:
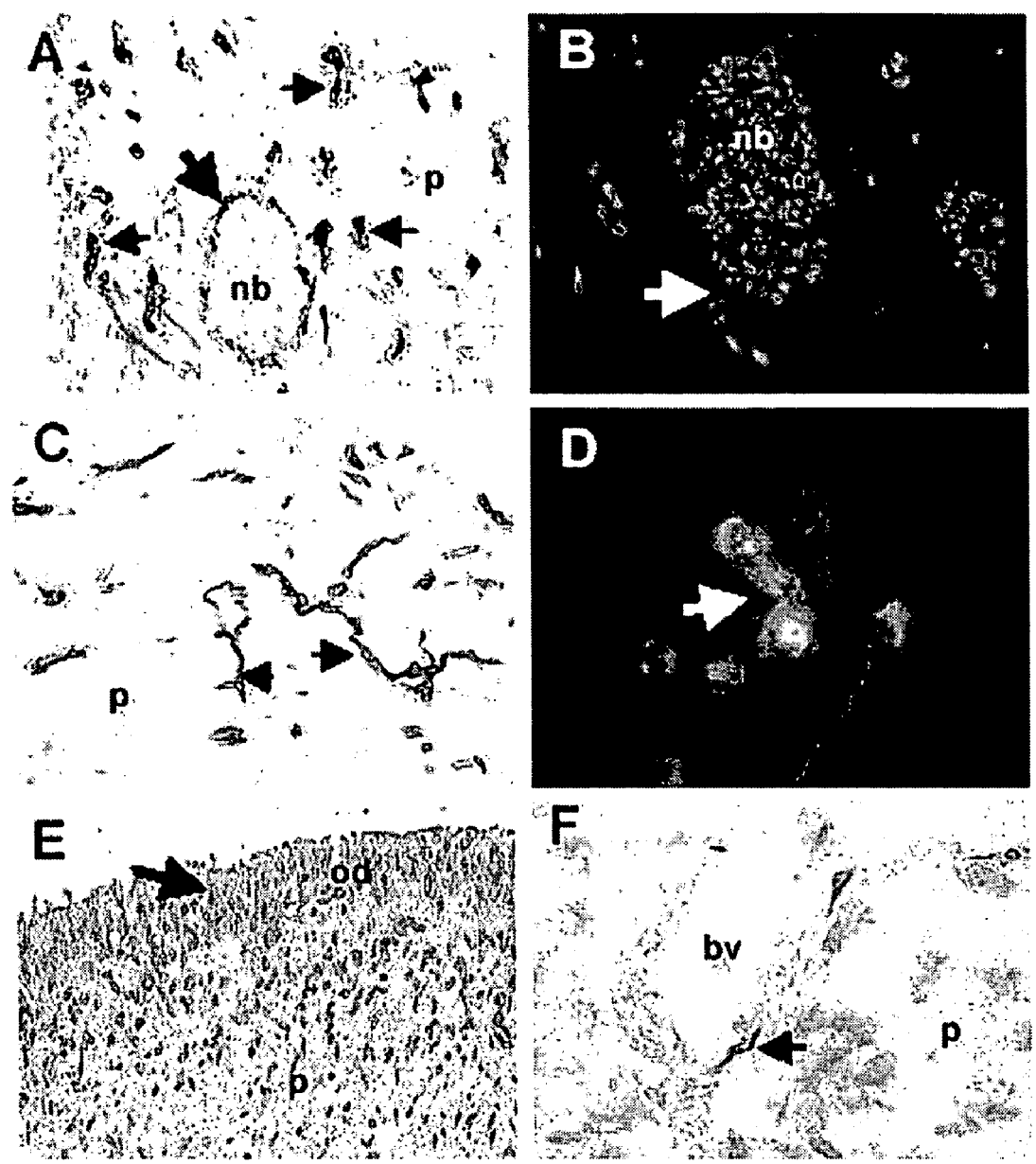

FIG. 12. Reactivity of perivascular makers in dental pulp. (A) Immunolocalization of the STRO-1 antigen on blood vessels (small arrows) in human dental pulp (p) and around perineurium (large arrow) surrounding a nerve bundle (nb) 20×. (B) Dual Immunofluorescence staining demonstrating reactivity of the STRO-1 antibody labeled with Texas Red to dental pulp perineurium (arrow) in combination with an anti-neurofilament antibody labeled with fluorescein isothiosyanate staining the inner nerve bundle (nb), 40×. (C) Immunolocalization of the CD146 antigen to blood vessel walls in human dental pulp tissue 20×. (D) Dual Immunofluorescence staining demonstrating reactivity of the STRO-1 antibody labeled with Texas red to a blood vessel and the CC9 antibody labeled with fluorescein isothiosyanate. (E) Immunohistochemical staining of pulp tissue with a rabbit polyclonal anti-DSP antibody (arrow) to the odontoblast outer layer (od). 20×. (F) 3G5 reactivity to a single pericyte (arrow) in a blood vessel (bv) wall 40×. Tissue sections were counter stained with Hematoxylin.

Figure 13:
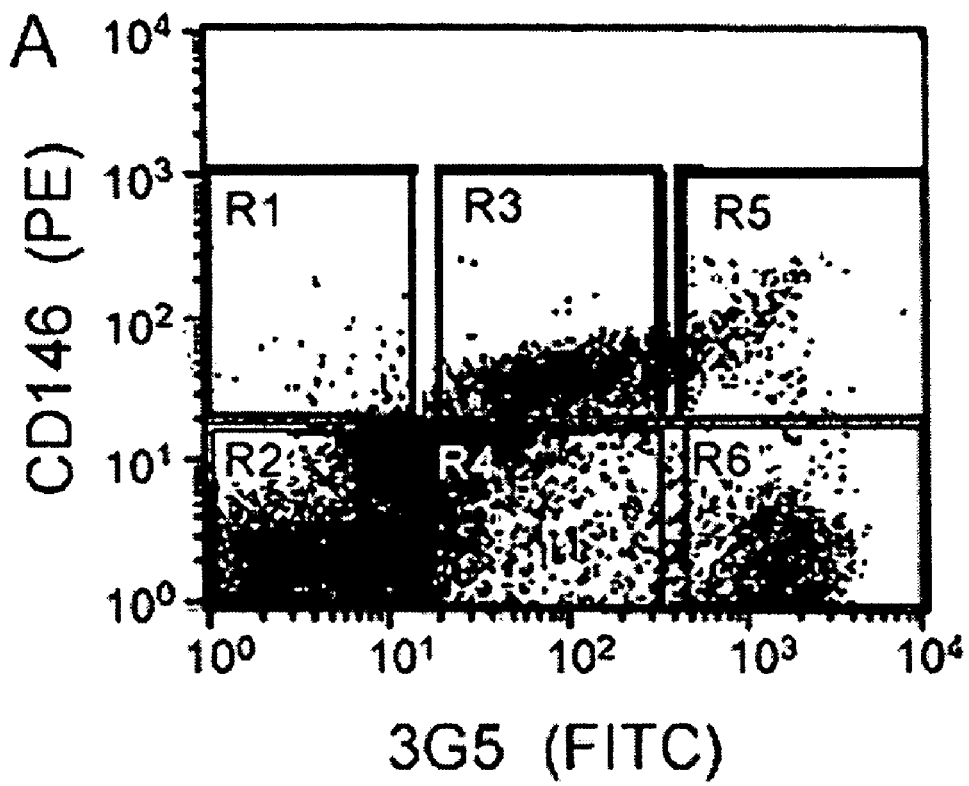

FIG. 13. 3G5 reactivity to BMSSCs. (A) The representative histogram depicts a typical dual-color FACS analysis profile of whole bone marrow mononuclear cells (BMMNCs) expressing CD146 (PE) and 3G5 (FITC). (B) Colony efficiency assays were performed for all the different expression patterns observed (regions "R" 1-6). The data are expressed as the mean incidence of colony-forming units for each cell fraction averaged from three separate experiments.

Figure 14:
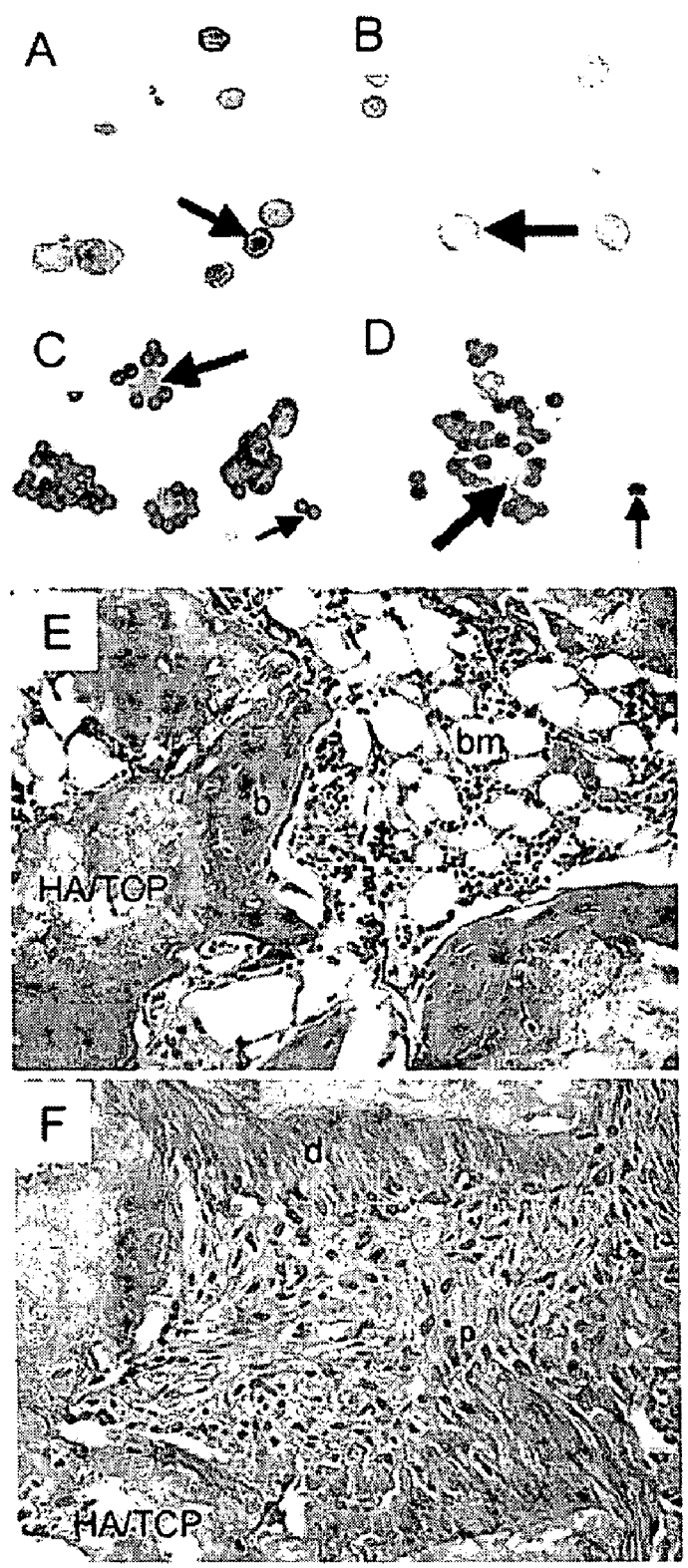

FIG. 14. Developmental potential of purified BMSSCs and DPSCs in vivo. Cytospin preparations of MACS/FACS isolated STRO-1$^{BRT}$/CD$_{146}$+ marrow cells (arrow) stained with an antibody specific to α-smooth muscle actin (A) and von Willebrand Factor (B). CD146+ pulp cells (large arrow) isolated by immunomagnetic bead selection (magnetic beads depicted by small arrows), stained with an antibody specific to α-smooth muscle actin (C) and von Willebrand Factor. (D). (E) Ectopic bone formation (b) and haematopoietic/adipogenic marrow (bm) by ex vivo expanded cells derived from STRO-1$^{BRT}$/CD146+ BMSSCs transplanted with HA/TCP into immunocompromised mice for three months (E). (F) Ectopic formation of dentin (d) and fibrous pulp tissue (p) by ex vivo expanded cells derived from CD146+ DPSCs transplanted with HA/TCP into immunocompromised mice for three months. Sections were stained with Hematoxylin & Eosin.

Figure 15:
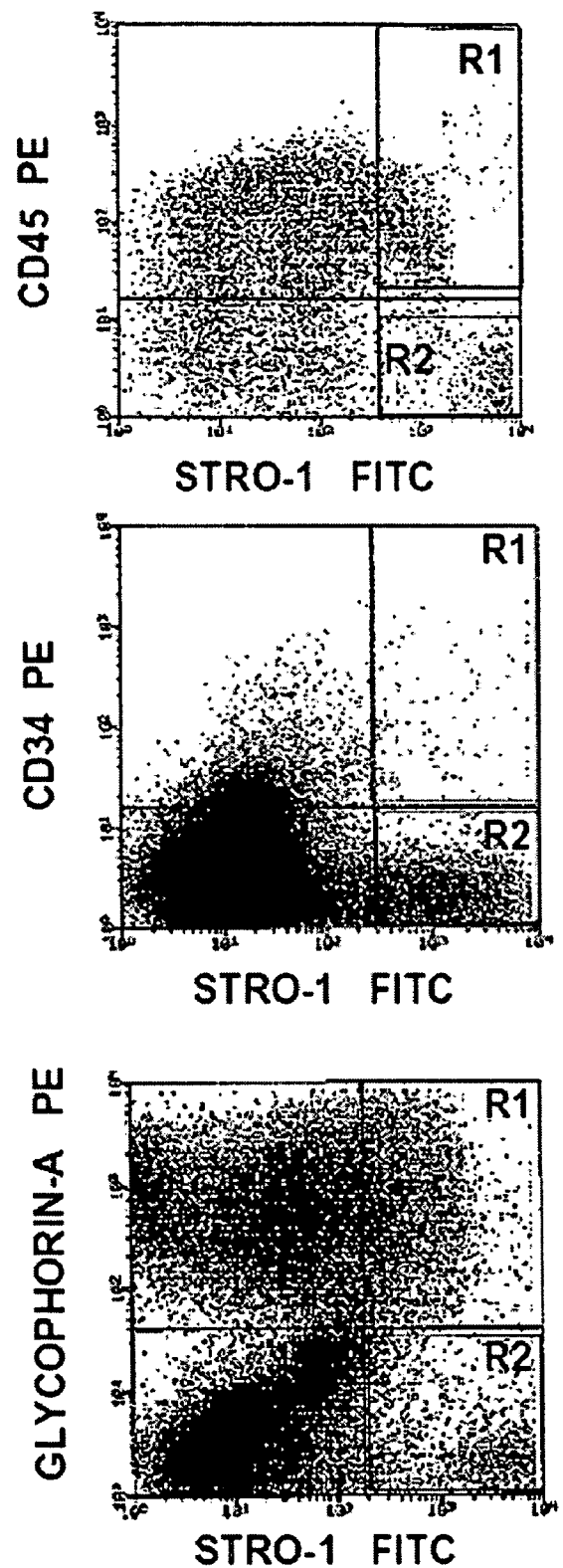

FIG. 15 Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

Figure 16:
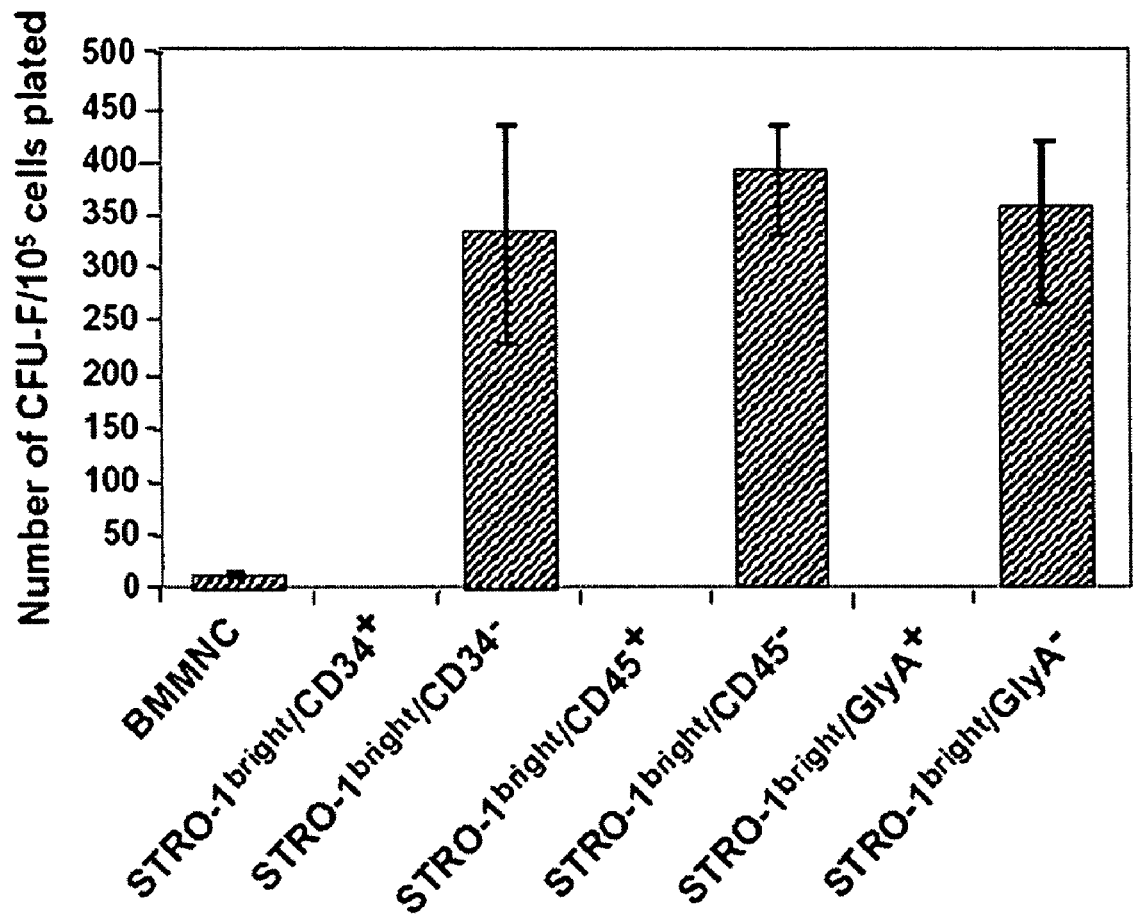

FIG. 16 Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Gycophorin-A antigens, based on regions R1 and R2 as indicated in FIG. 15. These data are expressed as the mean incidence of colony-forming units for each cell fraction averaged from two separate experiments.

FIG. 17 Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (Panel 1), brain, kidney (Panel 2), liver, heart (Panel 3) and skin (Panel 4) 20×. The STRO-1 and 3G5 antibodies were identified using a goat anti-murine IgM-Texas Red while CD146 and alpha-smooth muscle actin were identified using a goat anti-murine or IgG-fluorescein isothiocyanate. Co-localization is indicated by overlapping areas of yellow and orange fluorescence (white arrows).

Figure 18:
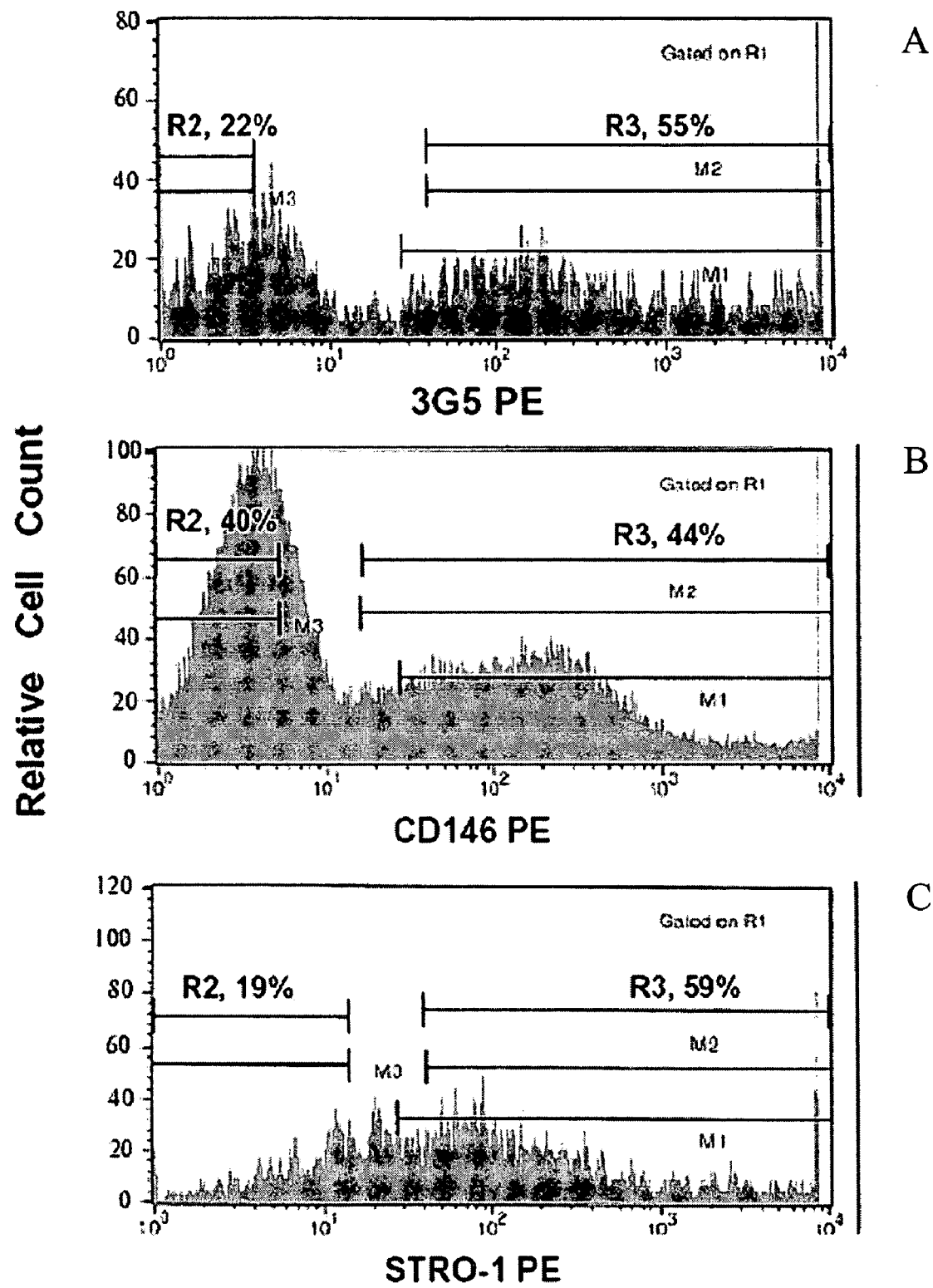

FIG. 18 Isolation of adipose-derived MPC by FACS. Representative flow cytometirc histograms depicting the expression of STRO-1, CD146 and 3G5 in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Figure 19:
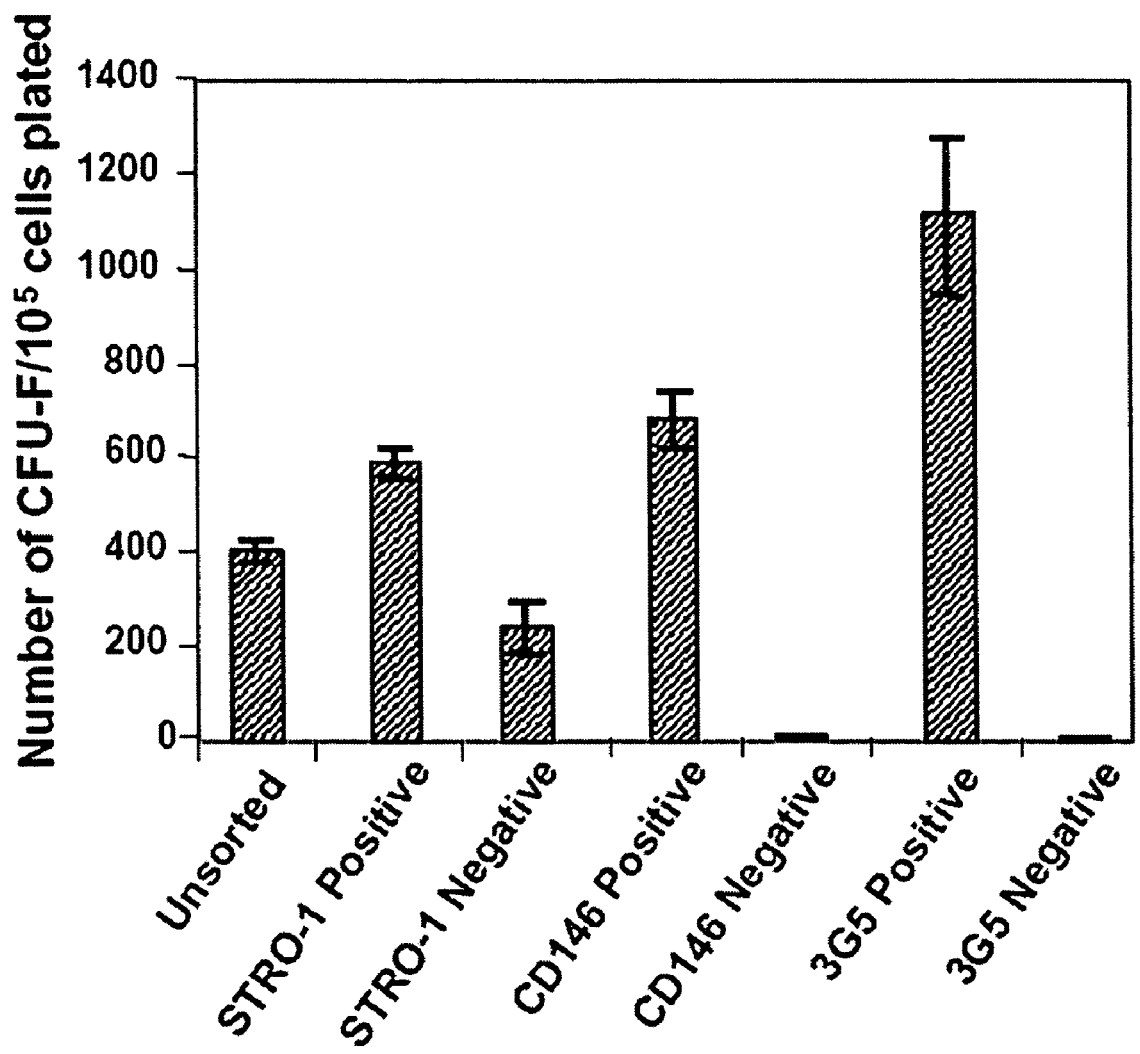

FIG. 19 Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 18), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

Figure 20:
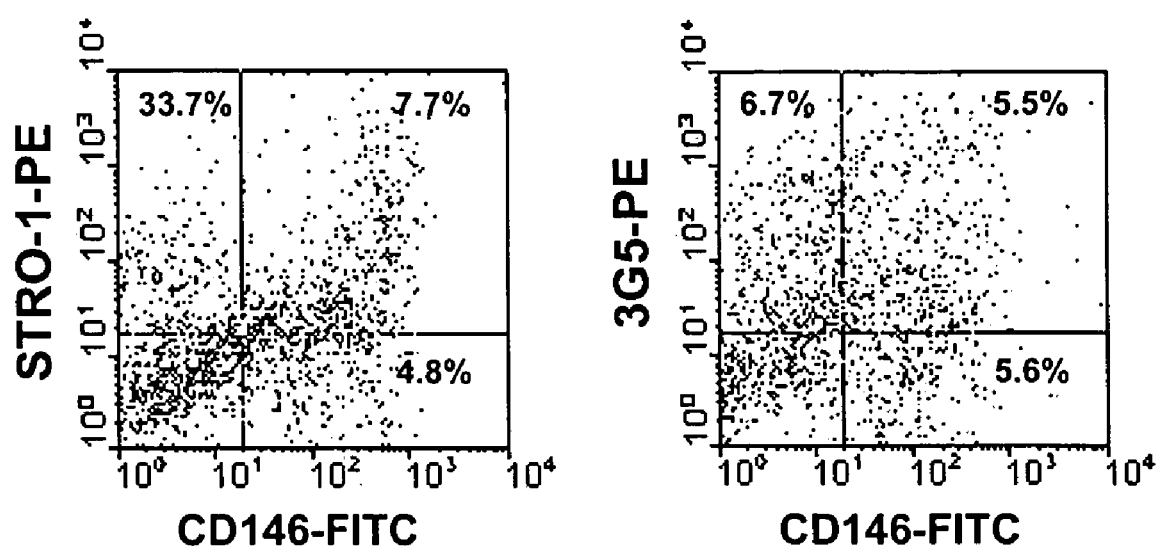

FIG. 20 Immunophenotypic analysis of adipose-derived MPC. Representative flow cytometric histograms depicting the co-expression of STRO-1 and CD146 (A) and 3G5 and CD146 in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate. Approximately 60% and 50% of the CD146 positive cells co-express STRO-1 and 3G5, respectively. These data suggest that 10% or more of the CD164 positive cells co-express STRO-1 and 3G5.

Figure 21:
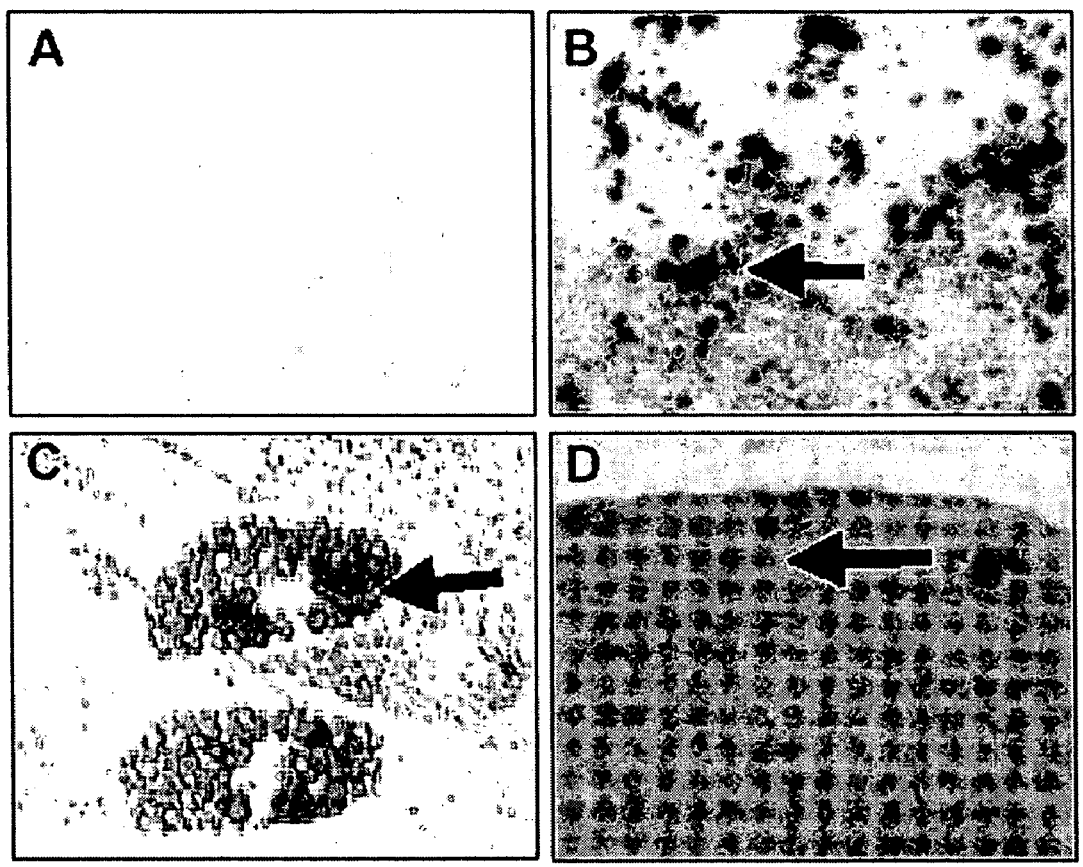

FIG. 21 Developmental potential of purified Adipocyte-derived MPC in vitro. Preparations of primary MPC cultures derived from STRO-1$^+$/CD146$^+$ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

Figure 22:
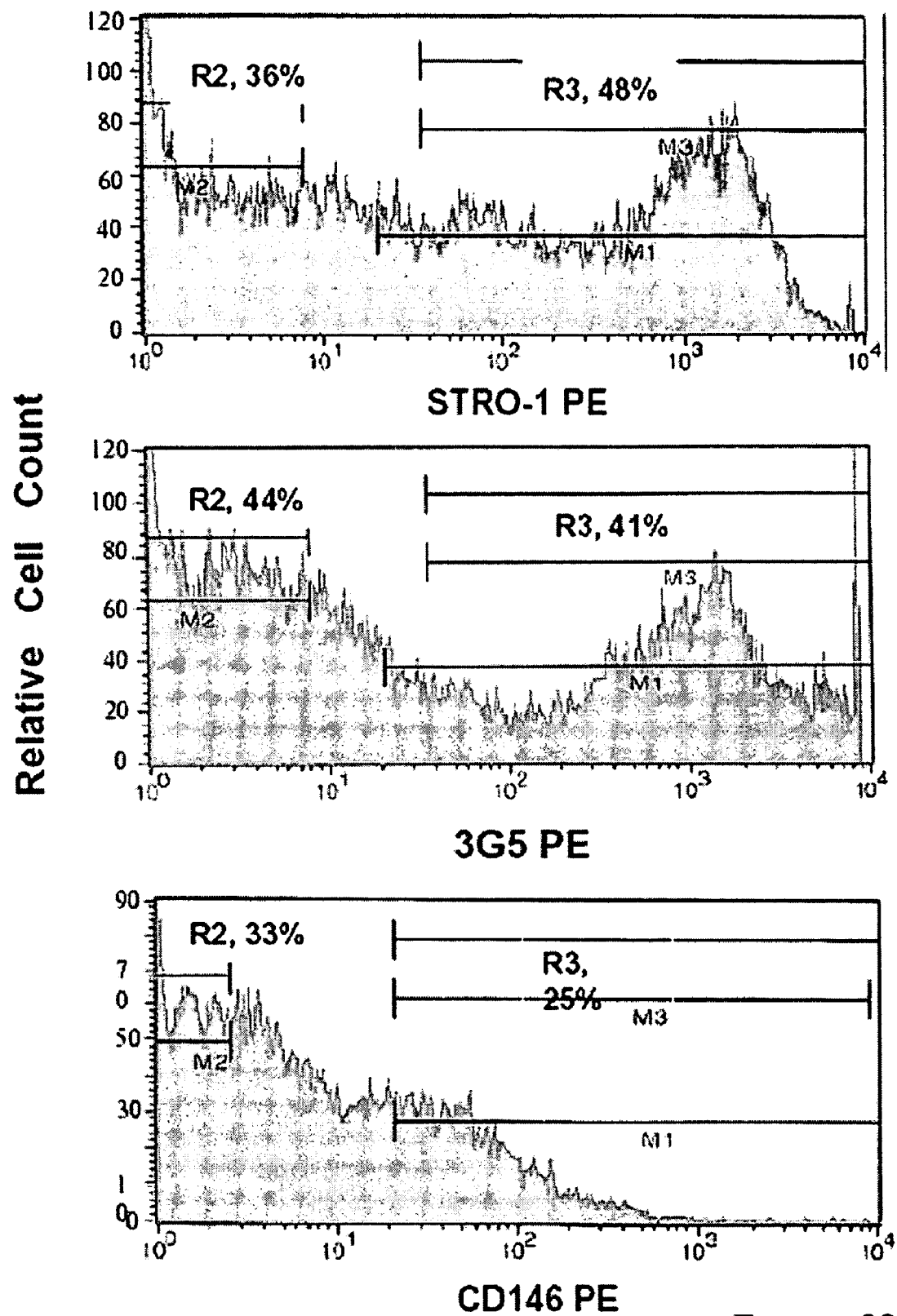

FIG. 22 Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Figure 23:
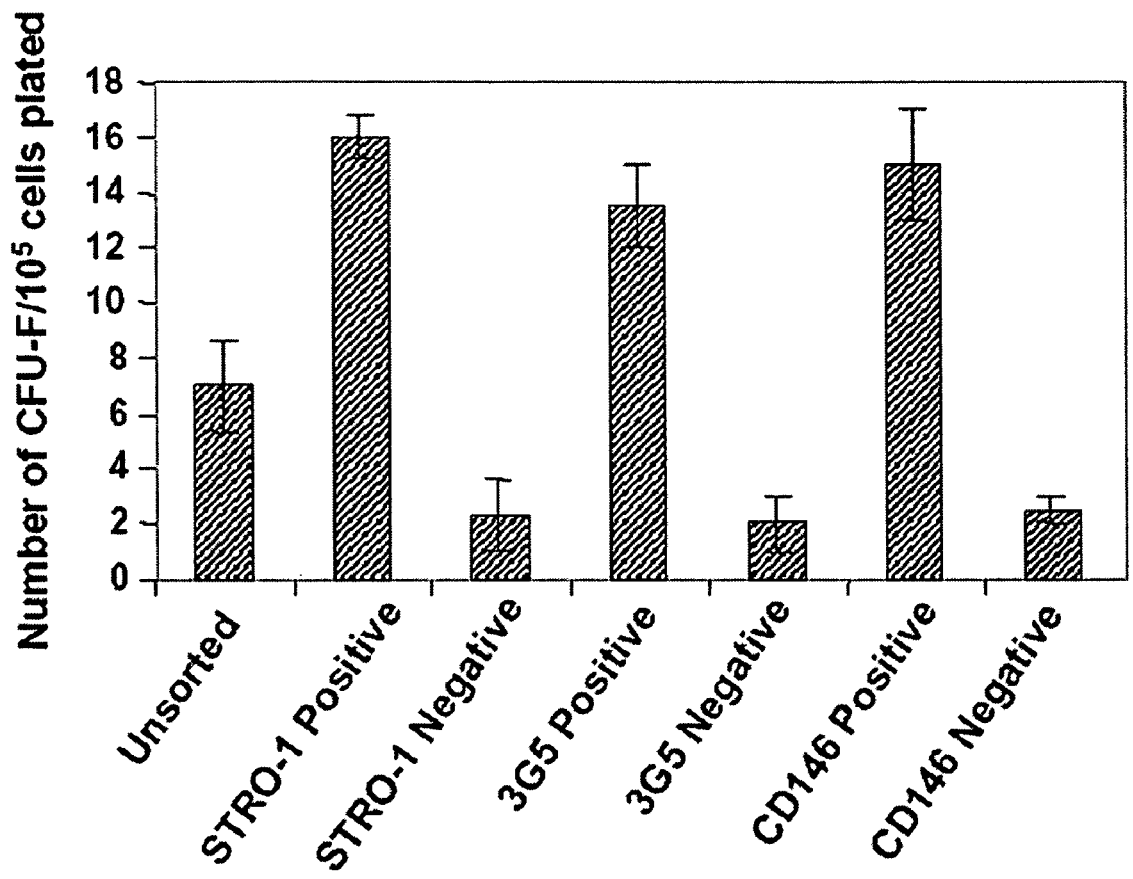

FIG. 23 Clonogenic skin-derived MPC are positive for STRO-1/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5 (FIG. 15), then cultured in standard growth medium as previously described for bone marrow and dental pulp tissue (Shi and Gronthos 2003). The data are expressed as the number of colony-forming units obtained per 105 cells plated in the positive and negative cell fractions averaged from two separate experiments.

FIG. 24A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeanbilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker (bold line) with reference to the isotype matched negative control antibodies (thin line). B. Gene expression profile of cultured MPC. Single cell suspensions of ex vivo expanded bone marrow MPC were prepared by trypsin/EDTA treatment and total cellular RNA was prepared. Using RNAzo1B extraction method total RNA was isolated and used as a template for cDNA synthesis, prepared using standard procedure. The expression of various transcripts was assessed by PCR amplification, using a standard protocol as described previously (Gronthos et al. 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the housekeeping gene, GAPDH, using ImageQuant software.

Figure 25:
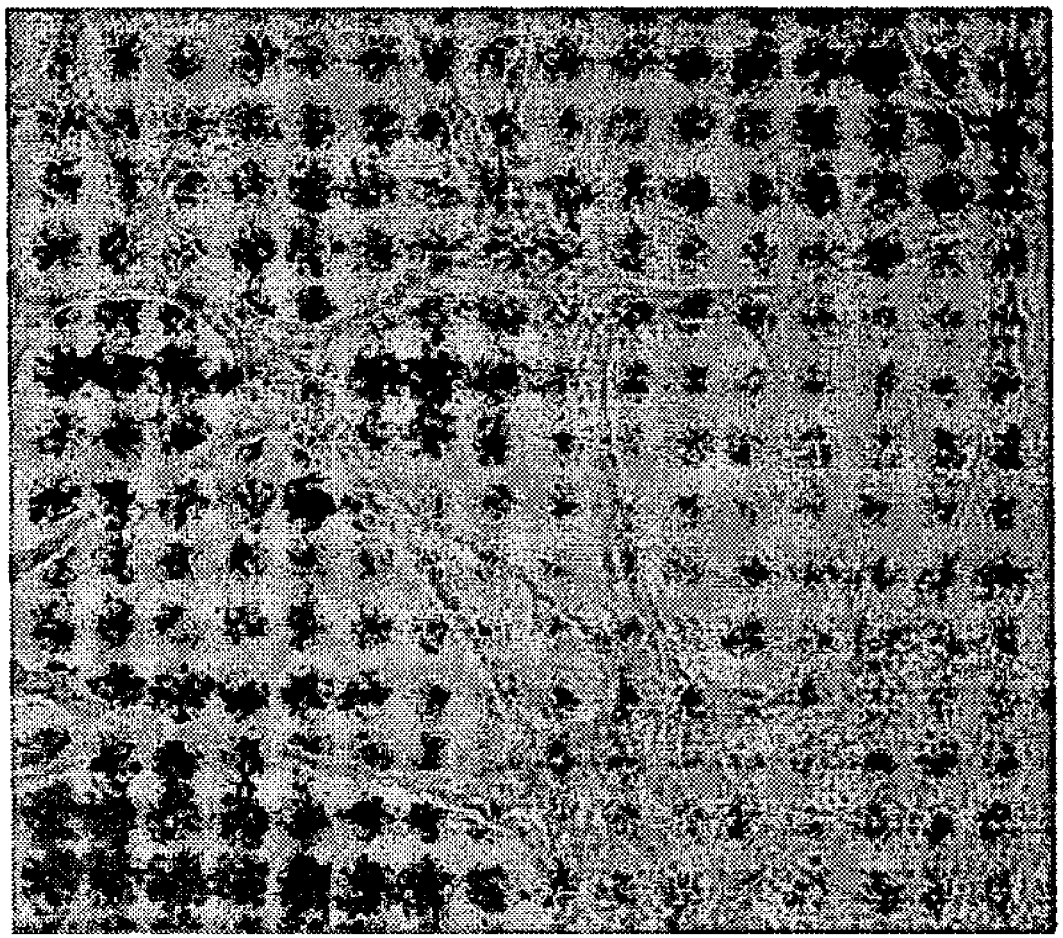

FIG. 25. Ex vivo expanded STRO-1$^{bri}$ MPC can develop into arterioles in vitro. Single cell suspensions of ex vivo expanded bone marrow STRO-1$^{bri}$ MPC were prepared by trypsin/EDTA treatment then plated into 48-well plates containing 200 µl of matrigel. The STRO-1$^{bri}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

EXAMPLE 1

Isolation of Mesenchymal Precursor cells

To properly investigate the biology of BM MPC, studies were designed to isolate MPC from a heterogeneous population of unfractionated BM cells. This was achieved by using a combination of positive immunoselection procedures based on the unique specificity of the STRO-1 mab, in order to maximise the recovery and purity of the MPC population. Following the isolation of homogeneous populations of MPC we then explored their pattern of gene expression for various bone-, fat- and cartilage-related markers to determine the degree of commitment towards different stromal cell lineages in vivo. Finally we have investigated the developmental potential of purified populations of BM MPC in vitro under defined conditions [Gronthos et al, 1994] and in vivo by ectopic implantation into immunodeficient mice [Haynesworth et al, 1992].

We and others have had success in isolating MPC based on their expression of the STRO-1 antigen either by FACS or by using immunomagnetic particles, such as Dynabeads [Tamayo et al, 1994] or by magnetic-activated cell sorting (MACS) [Gronthos et al, 1995 and 1998]. The latter was used initially to provide a reproducible technique for isolating BM derived MPC with the capacity to process high cell numbers. The mab STRO-1 proved to be an ideal reagent for isolating MPC from adult BM because of its lack of reactivity to haemopoietic progenitors [Simmons and Torok-Storb, 1991a] yielding a clean separation between MPC and haemopoietic progenitors in adult BM. Moreover, the antigen identified by STRO-1 was found in the present study to be expressed at particularly high copy number by MPC, which may in part account for the high efficiency and recovery of BM CFU-F observed. These studies identified the minor STRO-1$^{bright}$ subset of the total STRO-1$^+$ BMMNC fraction to contain the CFU-F population. However the resulting post MACS STRO-1$^{bright}$ cell population was only partially enriched for MPC.

We have previously demonstrated that the cell surface antigen, VCAM-1 is universally expressed on BM MPC and their progeny [Simmons et al, 1992, 1994]. This is in contrast to other markers expressed by BM MPC such as THY-1, CD10, CD13, and thrombomodulin, [Simmons et al, 1994] which are also known to react with either haemopoietic cells and or platelets [Baum et al, 1992; Conway and Nowakowski, 1993; Ship and Look, 1993]. The VCAM-1 molecule is a transmembrane glycoprotein with a molecular weight of between 95 and 110 kDa present on the membranes of stromal cells and endothelial cells [Osborn et al, 1989; Simmons et al, 1992]. The immunoglobulin super family member is one ligand for the integrin receptor α4β1 (VLA-4) present on haemopoietic stem cells, and is involved in the recruitment of lymphocytes and monocytes expressing α4β1 to sites of infection and inflammation [Elices et al, 1990; Simmons et al, 1992].

Significantly, VCAM-1 only reacted with a minor proportion of BMMNC effectively subletting the total STRO-1$^+$ population, reacting preferentially with the STRO-1$^{bright}$ cell fraction. The BM MPC population was subsequently shown to reside exclusively in the STRO-1$^{bright}$/VCAM-1$^+$ fraction of human adult BM.

The absolute frequency of MPC in bone marrow was determined by limiting dilution experiments using Poisson distribution statistics. Other studies using this statistical analysis have shown that murine BM osteoprogenitor cells with the potential to form mineralized bone nodules in vitro, occurred at a frequency of 1 per 1000 BM cells plated, based on the phenotype 5-fluoracil resistant, haemopoietic lineage marker negative [Van Vlasselaer, 1994]. These osteoprogenitors represented approximately 20% of the total MPC population in normal murine BM [Falla et al, 1993; Van Vlasselaer, 1994]. Similar analyses of fetal human BMMNC demonstrated the frequency of MPC at 1 per 1,000 to 1 per 100,000 cells plated, at 14 weeks and 24 weeks gestation, respectively, based on the immunophenotype CD34$^+$/CD38$^-$/HLA-DR$^-$ [Waller et al, 1995a]. Furthermore, additional subletting of fetal BM using the haemopoietic marker CD50, distinguished HSC from the MPC population, but found no significant difference in the incidence of clonogenic stromal cells sorted on the basis of the phenotype CD34$^+$/CD38$^-$/HLA-DR$^-$/CD50$^-$ [Waller et al, 1995b]. However, no stromal progenitors were observed when single cells of human adult BM samples were sorted based on the CD34$^+$/CD38$^-$/HLA-DR$^-$ phenotype [Waller et al, 1995a]. This may be due to the inefficiency of a predominantly negative selection criteria used to isolate fetal BM MPC and may also reflect the use of the CD34 antigen which demonstrates low level expression on adult BM MPC [Simmons and Torok-Storb, 1991b].

In the illustrated embodiment, the incidence of clonogenic cells (clusters 10<50 cells+colonies 50) from adult human BM was determined to be 1 per 2 STRO-1$^{bright}$/VCAM-1$^+$ cells plated in SDM containing PDGF and EGF. Using serum-deprived medium significantly enhances the incidence of clonogenic growth over that of serum replete cultures, particularly at low plating densities [Gronthos and Simmons, 1995]. It must also be stated that a proportion of the wells which were scored as 'negative' contained cell clusters of less than 10 cells. Therefore, by further refining the CFU-F culture assay, it may be possible to stimulate the growth of MPC in order to increase the overall purity of the MPC population based on the composite STRO-1$^{bright}$/VCAM-1$^+$ phenotype. Nevertheless, the combined purification technique of the illustrated embodiment effectively achieved a several thousand fold increase in the incidence of BM MPC when compared to unfractionated BMMNC.

The cells contained within the STRO-1$^{bright}$/VCAM-1$^+$ BM fraction were found to be a homogeneous population of large cells with extensive cytoplasmic processes existing in vivo in a non-cycling state. Other studies have found that MPC residing in the BM are almost entirely non-cycling as shown by $^3$H thymidine labelling in rodents and by means of the in vitro thymidine suicide technique in humans [Castro-Malaspina et al, 1980; Castro-Malaspina et al, 1981]. This data coincides with the observations that primitive multi-potential stem cells, identified in the other cell systems such as HSC are by definition quiescent cells [Andrews et al, 1986; Szilvassy et al, 1989; Li and Johnson, 1992]. Given the reported developmental potential of cultured BM MPC in vitro and in vivo the question arises as to whether these cells are truly representative of an early uncommitted phenotype with multi-potential or whether all or a proportion of the CFU-F are already committed towards a particular stromal cell lineage.

Analysis of the gene expression pattern of purified adult BM MPC in the illustrated embodiment has revealed that many of the genes expressed by CFU-F in vivo demonstrate a broad stromal tissue distribution related to osteoblasts, adipocytes and chondrocytes. It is very common to find in the literature that many markers for example osteonectin, osteopontin, and alkaline phosphatase in the bone cell lineage are described as being specific to bone cells, when in fact these markers have a wider tissue distribution. Therefore, it is not surprising to find that MPC identified by STRO-1 share common markers with differentiated stromal cell types. Importantly, specific markers of commitment such as CBFA-1, collagen type II, PPARγ2, [reviewed in Rodan and Harada, 1997] to bone, cartilage and fat respectively were not expressed by the STRO-1$^{bright}$/VCAM-1$^+$ population in fresh BM aspirates. In addition, immunohistochemical examination of STRO-1$^{bright}$/VCAM-1$^+$ sorted BMMNC failed to show any reactivity to the smooth muscle marker α-smooth muscle actin or with the endothelial marker, FVIII. Therefore the MPC residing in the BM seem to exist in an uncommitted state, and may have the potential under different conditions to develop into a few or all of the stromal elements recognised in the bone marrow microenvironment.

In the present study, cultures of purified STRO-1$^{bright}$/VCAM-1$^+$ human BM CFU-F typically developed a von Kossa positive mineral by twenty one days under osteogenic conditions (ASC-2P, PO$_{4i}$, DEX). The presence of mineral deposits was demonstrated in all CFU-F clones examined, where 40% of the clones also displayed the capacity to differentiate into adipocytic cell clusters. Moreover, individual CFU-F clones were also found to contain a small proportion of fibroblastic-like cells not associated with either mineralization or lipid accumulation. These fibroblast-like cells may represent as yet undefined stromal populations such as reticular cells, smooth muscle cells, bone lining cells, osteocytes and committed stromal progenitors.

The developmental potential of selected CFU-F clones was further examined in vivo. The porous hydroxyapatite coated ceramic cubes reproducibly supported the development of human osteogenic tissue in SCID mouse. This is in agreement with the findings in previous in vivo studies using unfractionated rodent and human BM mesenchymal cell cultures

[Haynesworth et al, 1992a; Krebsbach et al, 1997; Kusnetsov et al, 1997]. In the present study, pretreating the HA ceramic cubes with purified fibronectin was critical to maximise the number of cells retained in the cubes after loading prior to transplantation (data not shown). Pre-treatment of HA cubes with fibronectin and laminin has been reported to increase cell retention and spreading on the ceramic surface of the cubes [Dennis et al, 1992; Dennis and Caplan; 1993]. Fibronectin and laminin coated cubes were found to augment bone formation from cultured rat BM mesenchymal cells at earlier time points in comparison to untreated cubes [Dennis et al, 1992; Dennis and Caplan, 1993].

The present study failed to detect cartilage formation in any of the transplantation models used, in contrast to other studies which demonstrated cartilage formation in diffusion chambers transplanted with rodent bone marrow or mesenchymal cells derived from the marrow of young children. To date, there have been no reports describing the reproducible induction of cartilage formation using adult human bone marrow stromal cells in vivo or in vitro. In the present study, the expression of the hypertrophic chondrocyte marker collagen type X, by purified adult human BM MPC, is somewhat puzzling, given the presumed specificity of this molecule. Since the physiological role of collagen type X is unknown, its significance in bone marrow remains to be determined.

The present work is in accord with previous studies showing that the formation of new bone in implants of HA cubes is attributed to differentiation of human mesenchymal cells into functional osteoblasts [Kusnetsov et al, 1997] and did not result from the recruitment of osteoprogenitors from the surrounding host (mouse) tissue. Furthermore, other cell types present such as muscle, adipocytes and vascular endothelial cells showed no hybridization with the alu probe and are therefore presumed to be host in origin. These findings demonstrate that a proportion of BM MPC within the STRO-$1^{bright}$/VCAM-$1^+$ BM subfraction, demonstrate the capacity to develop into multiple stromal cell types including osteoblasts, adipocytes and fibroblast-like cells.

Further subletting of the STRO-$1^{bright}$/VCAM-$1^+$ BM fraction using three- and four-colour FACS analysis may eventually provide a means to discriminate between subpopulations contained within the MPC pool which exhibit different developmental potentials. The purification of MPC clones with different potential may then be used to generate multi-potent, bi-potent and uni-potent cell lines which could greatly facilitate the design of experimental approaches to study the molecular mechanisms regulating the commitment of early precursors into different stromal cell lineages.

One area of potential benefit that will occur from a greater understanding of the proliferation and differentiation of MPC, is the ability to manipulate and expand mesenchymal cell populations in vitro for subsequent reimplantation in vivo. The use of animal models has demonstrated the efficacy of utilising ex vivo expanded BM mesenchymal cells to facilitate bone regeneration and tendon repair in vivo [Bruder et al, 1998b; 1998c; Young et al, 1998]. Several studies have also described how cultured marrow stromal cells from a variety of species are readily infected using either amphotropic retroviruses or adenoviruses [Harigaya and Handa, 1985; Rothstein et al, 1985; Singer et al. 1987; Cicutinni et al, 1992; Roecklein and Torok-Storb, 1995]. In addition, some studies have demonstrated the persistence of transplanted transduced cells over several months in animal models [Li et al, 1995; Anklesaria et al, 1996; Onyia et al, 1998 Reiw et al, 1998]. Therefore the ability to harvest purified human MPC from aspirates of BM and to expand these cells ex vivo makes them ideal candidates as possible vehicles for gene transfer, in order to treat a variety of diseases and genetic disorders.

Materials and Methods

Subjects

Aspirates of human BM samples were obtained from the iliac crest and the sternum of normal adult volunteers with their informed consent, according to procedures approved by the ethics committee at the Royal Adelaide Hospital, South Australia. Bone marrow mononuclear cells (BMMNC) were obtained by centrifugation over Ficoll 1.077 g/ml (Lymphoprep, Nycomed, Oslo, Norway) at 400 g for 30 minutes (min) and then washed and resuspended with Hank's buffered saline solution containing 1% bovine serum albumin and 10 mM HEPES, pH 7.35 (HBSS).

Isolation of STRO-1+ Cells by Magnetic-Activated Cell Sorting (MACS)

This procedure is a modification of that described elsewhere [Gronthos et al, 1998]. Approximately $1 \times 10^8$ BMMNC were incubated with STRO-1 supernatant for 60 min on ice. The cells were then washed in HBSS and resuspended in 1 ml of HBSS containing a 1/50 dilution of biotinylated goat anti-mouse IgM (μ-chain specific; Southern Biotechnology Associates, Birmingham, Ala.) for 45 min on ice. Following this, the cells were washed twice in MACS buffer (single strength $Ca^{2+}$ and $Mn^{2+}$ free PBS supplemented with 1% BSA, 5 mM EDTA and 0.01% sodium azide) and resuspended in 900 μl of MACS buffer to which 100 μl of streptavidin microbeads (Miltenyi Biotec, Bergisch Gladbach, F.R.G.) was added. The cells were further incubated for 15 min on ice after which streptavidin-fluorescein isothiosyanate (FITC) conjugate (1/50; Caltag Laboratories, San Francisco, Calif.) was added directly to the suspension for an additional 5 min. The cells were separated on a Mini MACS magnetic column (column capacity $10^7$ cells, Miltenyi Biotec) according to the manufacturers specifications.

Purification of the CFU-F Population by Fluorescence Activated Cell Sorting (FACS)

Dual colour-FACS analysis of the STRO-$1^{bright}$ population was achieved by incubating the MACS isolated STRO-1 population with saturating levels of the Mab 6G10 (mouse IgG1 anti-human CD106: vascular endothelial adhesion molecule-1, VCAM-1; kindly donated by Dr. B. Masinovski FCOS Corp., Seattle Wash.) for 30 min on ice. After washing with HBSS the cells were incubated with a second label goat anti-mouse IgG (γ-chain specific) phycoerythrin (PE) conjugate antibody (1/50; Southern Biotechnology Associates, Birmingham, Ala.) and a streptavidin-FITC conjugate (1/50; CALTAG Laboratories, San Francisco, Calif.) for 20 min on ice. The cells were then washed in HBSS prior to being sorted using the automated cell deposition unit (ACDU) of a FACStar$^{PLUS}$ (Becton Dickinson, Sunnyvale, Calif.) flow cytometer. STRO-$1^{bright}$/VCAM-1+ cells were seeded at plating densities of 1, 2, 3, 4, 5, and 10 cells per well (96-well plates) in replicates of 24 wells per plating density (FIG. 2). The cells were cultured in serum deprived medium on fibronectin coated wells as previously described [Gronthos and Simmons 1995; Gronthos et al, 1998]. On day 10 of culture the cells were then fixed and stained for 60 min with 0.1% toluidine blue in 1% paraformaldehyde. Aggregates of 50 cells were scored as CFU-F colonies and aggregates of 10<50 cells were scored as clusters using an Olympus SZ-PT dissecting light microscope (Olympus Optical Co. Ltd, Tokyo, Japan).

Analysis of Cell Cycling Status of STRO-1+ BMMNC

The STRO-$1^+$ BMMNC were isolated by MACS as described above and then incubated with streptavidin PE for 15 min on ice. After washing twice with PBS the cells were fixed for 10 min with cold methanol (70%) on ice. Following this, the cells were washed three times with PBS and then incubated in blocking buffer for 15 minutes. The monoclonal antibody Ki-67 conjugated to FITC (DAKOPATTS A/S, Glostrup, Denmark) was added directly to the cells (1/10 dilution) in blocking buffer for 45 min on ice served as the negative control.

RNA Isolation and First-Strand cDNA Synthesis

Total cellular RNA was routinely prepared from $2\times10^4$ STRO-$1^{bright}$/VCAM-$1^+$ cells collected as a bulk population and lysed using RNAzo1B extraction method (Biotecx Lab. Inc., Houston, Tex.), as per manufacturers recommendations. RNA isolated from each subpopulation was then used as a template for cDNA synthesis. cDNA was prepared using a First-strand cDNA synthesis kit from Pharmacia Biotech (Uppsala, Sweden) according to manufacturers instructions. Briefly, total RNA was resuspended in 8 µl of DEPC-treated water and subsequently heated to 65° C. for 10 min. Following snap cooling on ice, the RNA was added to 7 µl of premix containing reaction buffer, oligo-dT as primer and Superscript MMLV Reverse transcriptase. Following incubation at 42° C. for 60 min, the volume of the reaction was adjusted to 50 µl with the addition of 35 µl of sterile water. The samples were stored at −20° C.

Polymerase Chain Reaction (PCR)

Due to limiting cell numbers, the expression of various bone-related transcripts (Table I) was assessed by polymerase chain reaction (PCR) amplification, using a standard protocol [Sambrook et al, 1989]. Two microliters of first strand cDNA mixture from each subpopulation was diluted in a 50 µl PCR reaction (67 mM Tris HCl pH 8.8, 16.6 mM $(NH_4)_2SO_4$, 0.45% Triton X100, 200 µg/ml gelatin, 2mM $MgCl_2$, 200 µM each dNTP) containing 10 ng of each primer (Table 1), to which 2.5 units of Amplitaq DNA Polymerase (Perkin-Elmer, Norwalk, Conn., USA) was added. Reaction mixes were overlaid with mineral oil and amplification achieved by incubation in a Perkin-Elmer/Cetus thermal cycler. Primer design enabled typical cycling conditions of 94° C./(2 min), 60° C./(30 sec), 72° C./(1 min) for 40 cycles, with a final 10 min incubation at 72° C. To control for the integrity of the various RNA preparations, the expression of GAPDH and/or beta-2-microglobulin was also assessed. Following amplification, 10 µl of each reaction mixture was analysed by 1.5% agarose gel electrophoresis, and visualised by ethidium bromide staining.

The Developmental Potential of BM CFU-F in vitro

We have previously reported the conditions for the induction of human bone marrow stromal cells to develop a mineralised bone matrix in vitro [Gronthos et al, 1994]. Briefly, the osteogenic and adipocytic potential of thirty day 4 CFU-F clones derived from single STRO-$1^{bright}$/VCAM-$1^+$ sorted cells was assessed by culturing in alpha modification of Eagle's medium (α-MEM: Flow Laboratories) supplemented with 20% FCS, L-glutamine (2 mM), p-mercaptoethanol ($5\times10^{-5}$ M), L-ascorbic acid 2-phosphate (100 pM) (ASC-2P: Novachem, Melbourne, Australia), dexamethasone sodium phosphate ($10^{-8}$M) (DEX: David Bull Laboratories, Sydney, Australia), $KH_2PO_4$ (1.8 mM) (BDH Chemicals) and Hepes (10 mM), at 37° C., 5% $CO_2$. The media was changed twice a week for a period of six weeks. Cultures were rinsed twice with PBS then fixed in situ with 10% neutral formalin for 30 mon. Staining for vonKossa was performed according to the method of Pearse and Gardner (1972). Sections or culture wells were washed twice in distilled water and then stained in 5% aqueous $AgNO_3$ for 60 min under ultraviolet light. After staining with $AgNO_3$, the sections were washed twice with distilled water and then placed in 5% sodium thiosulphate for 1 min. Cultures were washed in distilled water, counter stained with Mayer's haematoxylin and mounted. Oil Red O (ORO) staining was performed as described by Grimble (1998). Briefly, cultures were fixed as described above, washed twice with PBS and air dried. Cultures were immersed in a solution 0.5% (w/w) ORO in isopropanol for 15 min at room temp., washed three times with distilled water and subsequently counterstained with haematoxylin.

Similarly, the chondrogenic potential of the same clones was assessed by culturing $2\times10^5$ cells per clone in 0.5 mls SDM supplemented with TGFβ1 and gently centrifuged at 200 g for 2 min in a 10 ml polypropolene tube then incubated at 37° C., 5% $CO_2$. The media was changed twice a week for a period of three weeks The Developmental Potential of BM CFU-F in vivo Bulk cultures of CFU-F derived from STRO-$1^{bright}$/VCAM-$1^+$ sorted BMMNC were cultured for 5 weeks in the presence of ASC-2P and DEX and 10% FCS. The adherent cell layers were trypsinised and seeded onto 27mm$^3$ porous hydroxyapatite ceramic cubes (Zimmer Corporation, Warsaw, Ind., USA) pre-coated with fibronectin (5 µg/ml) (Boehringer Mannheim, Germany). The ceramic cubes were then implanted into subcutaneous pockets into the backs of SCID mice for a period of up to 8 weeks as described previously [Haynesworth et al, 1994; Kuznetsov et al, 1997]. Recovered implants were fixed in 10% buffered formalin for 2 days then decalcified for a further seven days in 0.5M EDTA before being embedded in paraffin wax. Cross-sections of the cubes were prepared as 5 µm sections onto glass slides pre-coated with Cell-Tak and counter stained with haematoxylin and eosin.

In situ Hybridization for the Human Specific alu Sequence

The HA ceramic implants were recovered 8 weeks post transplant and prepared for paraffin embedding on Cell-Tak coated slides as described above. To determine the origin of the cells within the implants in situ hybridization analysis was performed using a DNA probe specific to the unique human repetitive alu sequence [Kuznetsov et al, 1997]. The human specific alu sequence (pBLUR8; ATCC) was subcloned into the BamH1 restriction site of a pGEM-4Z plasmid (Promega). The digoxigennin-labeled alu specific probe was prepared by PCR containing 1×PCR buffer (67 mM Tris HCl pH 8.8, 16.6 mM $(NH_4)_2SO_4$, 0.5% Triton-X100, 0.2 µg/ml gelatin, 2.5 mM $MgCl_2$, 0.2 mM dATP, 0.2 mM dCTP, 0.2 mM dGTP, 1.9 mM dTTP, 0.1 mM digoxygenin-11-dUTP (Boehringer Mannheim), and 0.25 units of Amplitaq DNA Polymerase) and 100 ng of SP6 and T7 primers (Table 1) and 1 ng of plasmid DNA (pGEM-4Z; Promega Corp., Madison, Wis.) containing the alu sequence subcloned into the BamHI restriction site from (pBLUR8; ATCC, Rockville, Md.). Sections were deparaffinized with xylene and ethanol then rehydrated through graded (100%, 90%, 70%, 50%) ethanol solutions. The sections were then treated with 0.2N for 7 min at room temperature and then incubated in 1 mg/ml pepsin (Sigma, St. Louis, Mo.) in 0.1N HCl for 10 minutes at 37° C. After washing in PBS, the sections were treated with 0.25% acetic acid containing 0.1M triethanolamine (pH 8.0) for 10 min and prehybridized with 50% deionized formamide containing 4×SSC for 15 min at 37° C. The hybridization solution (1 ng/µl digoxigenin-labeled probe in 1×Denhardt's solution, 5% dextrane sulfate, 0.2 mg/ml, salmon sperm DNA, 4×SSC, 50-% deionized formamide) was then added to the sections for denaturation at 95° C. for 3 minutes followed by hybridization at 45° C. for 3 hr. After washing with 2×SSC and 0.1×SSC, digoxigenin-labeled DNA was detected by immunohistochemistry using antidigoxigenin alkaline phosphatase-conjugated Fab fragments (⅕₀₀₀; Boehringer Mannheim Corp., GMBH, Germany) followed by incubation with the corresponding alkaline phosphatase nitroblue tetrazolium/5-bromo-4-chloro-3-indolyl-phosphate substrate solution as recommended by Boehringer Mannheim. Micrographs were taken with Ektachrome 64 T colour film using an Olympus IMT-2 inverted light microscope.

Telomerase Repeat Amplification Protocol (TRAP) Assay

Telomerase activity was measured by a modified non-radioactive TRAP protocol essentially as described by Fong et al (1997). Telomerase cell extracts were prepared by the method of Kim et al, (1994), with minor modifications. Populations of sorted or cultured cells were lysed in ice-cold CHAPS extraction buffer (0.5% 3[(3-cholamidopropyl)-dimethyl-ammonio]-1-propanesulfonate], 50 mM Tris-HCI, pH 7.4, 5 mM $MgCl_2$, 5 mM EGTA, 25 mM 2-mercaptoethanol, 1 ng/ml leupeptin, and 50% glycerol in DEPC-treated water), at a concentration of 1000 cells/µl, incubated on ice for 30 minutes and centrifuged at 16000×g for 20 minutes at 4° C., the supernatant recovered and stored at −80° C. until required. Detection of telomerase activity was performed in a two-step process as previously described (Fong et al, 1997). Briefly, to 2 µl of cell extract, 16.5 µl of TRAP reaction buffer (20 mM Tris-HCI, pH8.2, 1.5 mM $MgCl_2$, 63 mM KCl, 0.05% Tween-20, 1 mM EGTA), 100 ng of each of TS primer (5'-AATC-CGTCGAGCAGAGTT-3'), and CX-ext primer (5'-GTGC-CCTTCCCTTACCCTTACCC TAA-3'), 0.5 µL dNTPs (10 mM stock) were added, and the reaction mix incubated at 25° C. for 30 minutes. Telomerase was subsequently inactivated by heating the reaction to 90° C. for 2 minutes, prior to the addition of 5 µl of PCR mixture, containing 3.5 µl of TRAP reaction buffer, 1 µl of CX-ext primer and 2.5 U Taq polymerase. Reaction mixes were covered with mineral oil and placed in a Hybaid thermocycler, and subjected for 34 cycles of 94° C. for 30 seconds, 50° C. for 30 seconds and 72° C. for 45 seconds, with a final extension at 72° C. for 2 minutes. To confirm the specificity of the telomerase products, in all cases, a 2 µl aliquot of each CHAPS lysate was subjected to denaturation by heating samples at 100° C. for 10 minutes. 25 µl of each reaction was resolved on a non-denaturing 12% polyacryalmide gel, and visualised by staining width SYBR Green fluorescent dye (FMC Bioproducts, OR, USA) as recommended by the manufacturer. The TRAP products were analysed using a fluorescence scanning system (Molecular Dynamics, Sunnyvale, Calif., USA).

Transmission Electron Microscopy (TEM)

STRO-$1^{bright}$/VCAM-$1^+$ cells (approximately 2×$10^4$ cells) were collected as a bulk population into eppendorf microtubes, washed once in 0.05M sodium cacodylate buffer and then fixed in 2.5% glutaraldehyde (EM Grade) in cacodylate buffer for 2 hr. The cultures were postfixed with 2% osmium tetroxide (VIII) (BDH Chemicals) in cacodylate buffer for I hr. After this, the cultures were dehydrated with graded ethanol solutions (70%, 90%, 100%). Epoxy resin (TAAB Laboratories; Berkshire, England) was then used to infiltrate the cultures overnight at 37° C. Polymerization of the resin was carried out at 60° C. for 24 hr under vacuum. Ultrathin sections were cut on a LKB 8800 Ultrotome II (Broma, UK) and mounted onto copper grids. Sections were then examined using a JEOL 1200 EX II (Tokyo, Japan) transmission electron microscope. Photographs were taken using ILFORD EM Technical film.

Results

Isolation and Purification of STRO-$1^+$ BM MPC

We have previously demonstrated the effectiveness of MACS to isolate and enrich for MPC from aspirates of human BM based on the cell surface expression of the STRO-1 antibody [Gronthos and Simmons, 1995; Gronthos et al, 1998]. In the present study, flow cytometric analysis of MACS isolated STRO-$1^+$ BMMNC cells demonstrated a heterogeneous pattern of expression spanning over four logs in fluorescence intensity (FIG. 1). Single-color FACS was subsequently employed to sort the STRO-$1^+$ BMMNC fraction into three subsets; STRO-$1^{dull}$ STRO-$1^{intermediate}$ and STRO-$1^{bright}$. Clonogenic assay for CFU-F in the different sorted STRO-$1^+$ subpopulations demonstrated that the majority of the MPC were contained within the STRO-$1^{bright}$ cell fraction. There was a 900 fold increase in the incidence of CFU-F in the STRO-$1^{bright}$ population when compared to unfractionated BMMNC (Table 1) demonstrating that BM MPC contained a high copy number of the STRO-1 antigen on their cell surface. The recovery of the MPC population in the STRO-$1^{bright}$ fraction was >75% in respect to the estimated total number of CFU-F in the BM sample pre-MACS.

We attempted to obtain a more accurate discrimination of the STRO-$1^{bright}$ subset by incubating the total STRO-$1^+$ MACS isolated cells with the stromal cell surface antigen VCAM-1 (FIG. 2A) previously found to react exclusively with BM MPC [Simmons et al, 1994]. Dual color-FACS was used to identify and isolate the STRO-$1^{bright}$/VCAM-$1^+$ BMMNC fraction. Limiting dilution analysis was subsequently performed, using the $FACStar^{PLUS}$ automated cell deposition unit, to seed STRO-$1^{bright}$/VCAM-$1^+$ cells at various plating densities as described in the methods. Cells were cultured under serum deprived conditions in the presence of PDGF and EGF (10 ng/ml) previously found to support the clonogenic growth of CFU-F above that of serum replete conditions particularly at low plating densities [Gronthos and Simmons, 1995]. The mean incidence (n=6 different BM donors) of day 10 CFU-F colonies (>50 cells) was determined to be 1 CFU-F per 3 STRO$1^{bright}$/VCAM-$1^+$ cells plated using Poisson distribution statistics (FIG. 2B). Furthermore, the incidence of clonogenic cells (clusters >10<50 cells+ colonies) was found to be 1 per 2 STRO-$1^{bright}$/VCAM-$1^+$ cells plated (FIG. 2C). The MACS/FACS purification technique effectively achieved a 5×$10^3$ fold enrichment of the CFU-F population when compared to unfractionated BMMNC with an average incidence of 1 CFU-F colony per $10^4$ BMMNC. It must also be stated that a proportion of the wells which were scored as 'negative' contained cell clusters of less than 10 cells.

Characterization of Purified BM MPC

Morphological examination of freshly sorted STRO-$1^{bright}$/VCAM-$1^+$ cells was carried out by transmission electron microscopy. Purified BM CFU-F appeared to be a homogeneous population of large cells containing many cytoplasmic processes and a large nucleous with an open chromatin structure (FIG. 3). To determine the cell cycling status of the CFU-F population in aspirates of BM the MACS isolated STRO-$1^+$ BMMNC fraction was further incubated with the cell cycling specific antigen Ki-67 [Gerdes et al, 1984; Wersto et al, 1988]. Two color flow cytometric analysis revealed that the STRO-$1^{bright}$ subset which contained the CFU-F population lacked co-expression of the Ki-67 antigen demonstrating that these cells are non-dividing in vivo (FIG. 4A). Telomerase activity was examined in cell extracts from sorted and cultured candidate stromal progenitor cell populations by a modified TRAP assay. Telomerase activity was present in all fractions including the candidate stromal stem cell compartment isolated from adult bone marrow, defined by their expression of both the STRO-1 and VCAM-1 (CD106) cell surface molecules (FIG. 4B).

To assess the proliferative capacity of BM MPC, individual CFU-F colonies (n=44) derived from two BM samples were expanded in the presence of serum under normal clonogenic growth conditions. A minor proportion of clones (8/44, 18%) demonstrated continued growth extending beyond 20 population doublings while the remainder showed little or no proliferation beyond 12 population doublings (FIG. 5). These cells also appeared to be capable of differentiating into adipose cells, whereas other isolated cells were less likely to do so.

A detailed phenotypic analysis of freshly isolated BM MPC pre-culture was compiled. Total RNA obtained from STRO-1$^{bright}$/VCAM-1$^+$ cells was used to generate full-length first-strand cDNA as described in the methods. RT-PCR analysis revealed the presence of various bone cell markers including bonesialoprotein, osteonectin, and collagen type I. However, there was an absence in the expression of osteopontin, the parathyroid hormone receptor, and the more specific bone cell markers osteocalcin and the transcription factor CBFAI (FIG. 6A). Similarly, the fat-related markers lipoprotein lipase and the adipocyte human lipid binding protein were found to be expressed by the STRO-1$^{bright}$/VCAM-1$^+$ population but there was no detectable expression of the adipocyte specific markers, the obese gene product (leptin) and the early transcription factor PPARγ2 in these cells (FIG. 6B). Furthermore the cartilage specific markers collagen type II and aggrecan were also not expressed by our purified MPC population. However the STRO-1$^{bright}$/VCAM-1$^+$ cell fraction was found to express collagen type X, a marker associated with hypertrophic chondrocytes (FIG. 6C). In addition, cytospin preparations of STRO-1$^{bright}$/VCAM-1$^+$ sorted BMMNC failed to show any reactivity to the smooth muscle marker α-smooth muscle actin or with the endothelial marker, FVIII (data not shown). Overall the MPC population appeared to represent an early precursor population not yet fully committed to anyone particular stromal cell lineage.

Culture expanded bulk CFU-F derived from STRO-1$^{bright}$/VCAM-1$^+$ sorted cells were assessed for their ability to develop into functional osteoblasts, chondrocytes and adipocytes in vitro as previously described [Gronthos et al, 1994]. A von Kossa positive mineralised matrix developed throughout the cultures by the end of the sixth week of induction (FIG. 7A). In addition, clusters of Oil Red O positive adipocytes were observed within the adherent layers in the same cultures (FIG. 7B). Following three weeks of chondrocytic induction in the presence of TGFβ1, the cells were also found to express the cartilage specific marker collagen type II by immunohistochemistry. Furthermore RT-PCR analysis of total RNA isolated from the different culture conditions demonstrated the expression of markers specific to bone (CBFA-1, OCN, PTH-R), fat (PPARγ2, leptin) and cartilage (collagen type II, aggrecan) (FIG. 6B).

The Developmental Potential of BM MPC Clones In Vitro and In Vivo

Bone marrow CFU-F clones were established from STRO-1$^{bright}$/VCAM-1$^+$ sorted cells from three individual BM donors. At day 4 of culture, single clonogenic clusters were identified and expanded by subculture. Half of the cells from the first passage were taken from each clone and cultured under osteogenic growth conditions as described above. The osteogenic potential of ninety CFU-F clones was assessed where a von Kossa positive mineralised matrix formed in all of the ninety clones. However, only a proportion (38%±15SEM, n=3) of the same clones gave rise to clusters of lipid containing oil red-O positive adipocytes demonstrating the bi-potential of the CFU-F population in vitro.

Half the cells from a representative 46 clones were subcultured and expanded for several weeks, then seeded into porous HA ceramic cubes and implanted subcutaneously into SCID mice for a period of 8 weeks as previously described [Haynesworth et al, 1992, Kusnetsov et al, 1997]. Cross-sections of the cubes prepared for histological examination showed that all of the implants contained an extensive network of blood vessels and fibrous tissue (FIGS. 8A and 8B). Bone formation was found in 42% (n=26) and 55% (n=20) of the clones isolated from two different BM aspirates. The ability of individual MPC clones to form a von Kossa positive mineralised matrix in vitro did not always correlate to the development of new bone in vivo. Similarly, the capacity of MPC clones to form adipocytic clusters in vitro had no bearing on the development of new bone formation in vivo.

The origin of the cellular material within the recovered implants was assessed by in situ hybridization using a DNA probe specific to the unique human repetitive alu sequence. The fibrous tissue, bone lining cells and osteocytes within the newly formed bone were all found to be positive for the alu sequence confirming their human origin and the bi-potential of a proportion of BM MPC (FIGS. 9C and 9D). Conversely, the fat and smooth muscle surrounding the ceramic cubes did not express the alu sequence and was therefore presumed to have originated from the host. Similarly, the endothelium lining the small blood vessels were also negative for the alu sequence implying they were derived from the mouse vasculature. In addition, there was no cartilage formation observed in sections of different implants and at different time points, as assessed by immunohistochemical analysis using a polyclonal antibody specific for collagen type II (data not shown).

Uses of MPCs

EXAMPLE 2

Repair of Articular Cartilage

Damaged articular cartilage generated by trauma or by diseases such as osteoarthritis and rheumatoid arthritis usually does not heal. However it is expected that this type of defect could be treated by implanting cultured MPCs of the present invention into the defect. The carrier may be pliable to mould to the shape of the defect and to promote round cell shape which is important for induction of chondrocyte differentiation. A suitable carrier may be constructed of collagen or fibrin. See Caplan et al. in U.S. Pat. No. 5,226,914.

EXAMPLE 3

Repair of Bone

A combination of MPCs as well as a suitable support can be introduced into a site requiring bone formation. Cultured MPCs contained in calcium phosphate ceramic vehicles may be implanted into the defect site. For appropriate methods and techniques see Caplan et al. in U.S. Pat. Nos. 5,226,914 and 5,837,539.

EXAMPLE 4

Anchoring of Prosthetic Devices

The surface of a prosthetic device can be coated with MPCs prior to implantation. The MSCs can then differentiate into osteogenic cells to thereby speed up the process of bony ingrowth and incorporation of the prosthetic device. See Caplan et al. in U.S. Pat. No. 5,226,914 and U.S. Pat. No. 5,837,539.

EXAMPLE 5

Gene Therapy

An exogenous nucleic acid that encodes a protein or peptide with therapeutic may be transformed into the enriched population using standard techniques (see U.S. Pat. No. 5,591,625 by Gerson et al.). The transformed cell population can then be introduced into the body of the patient to treat a disease or condition. For example, can be used to provide a continuous delivery of insulin, or genes encoding Factor VIII which is involved in clotting and therefore may be used in haemophiliacs.

EXAMPLE 6

Marrow Transplantation

A composition containing purified MPCs can be injected into a patient undergoing marrow transplantation prior to the introduction of the whole marrow. In this way the rate of haemopoiesis may be increased, particularly following radiation or chemotherapy. The composition might also include haemopoietic cells for use in radiotherapy or chemotherapy.

EXAMPLE 7

Isolation and Expansion of Precursor Cells

Stem cell niches identified in a number of different adult tissues including skin, hair follicles, bone marrow, intestine, brain, pancreas and more recently dental pulp, are often highly vascularized sites.[1] The maintenance and regulation of normally quiescent stem cell populations is tightly controlled by the local microenvironment according to the requirements of the host tissue.[2,3] Both the supportive connective tissues of bone marrow and dental pulp contain stromal stem cell populations with high proliferative potentials capable of regenerating their respective microenvironments with remarkable fidelity, including the surrounding mineralized structures of bone and dentin.[4,5] In the postnatal organism, bone marrow stroma exists as a loosely woven, highly vascularized tissue that supports and regulates hematopoiesis.[6-8] At a time when many tissues have lost or decreased their ability to regenerate, adult bone marrow retains a capacity for continuous renewal of haematopoietic parenchymal tissue and is responsible for remodeling the adjoining bone surfaces.[9,10] In contrast, the inner pulp chamber of teeth is comprised of a non-hematopoietic, compact fibrous tissue, infiltrated by a microvascular network, that is entombed by mineralized dentin.[11-13] Following tooth maturation, dental pulp becomes relatively static, acting only in a reparative capacity in response to a compromised dentin matrix caused by insults such as caries or mechanical trauma.

Precursors of functional osteoblasts (BMSSCs: bone marrow stromal stem cells) and odontoblasts (DPSCs: dental pulp stem cells), both forms of MPCs identified by their source tissue, were initially identified by their capacity to form clonogenic cell clusters in vitro, a common feature amongst different stem cell populations.[4, 14-18] The progeny of ex vivo expanded BMSSCs and DPSCs share a similar gene expression profile for a variety of transcriptional regulators, extracellular matrix proteins, growth factors/receptors, cell adhesion molecules, and some, but not all lineage markers characteristic of fibroblasts, endothelial cells, smooth muscle cells and osteoblasts.[4, 19] However, previous studies have documented that individual BMSSC colonies demonstrate marked differences in their proliferation rates in vitro and developmental potentials in vivo.[5,14,20] Similar to these findings, we have recently observed comparable levels of heterogeneity in the growth and developmental capacity of different DPSC colonies.[21] Together, these studies infer a hierarchical arrangement of stromal precursor cells residing in bone marrow and dental pulp, headed by a minor population of highly proliferative pluri-potential stem cells that give rise to committed bi- and uni-potential progenitor cell populations.[22]

Despite our extensive knowledge about the properties of cultured BMSSCs and DPSCs, we still do not know if their in vitro characteristics are an accurate portrait of their true gene expression patterns and developmental potentials in situ. In addition, it is not formally known if all of the colony-forming cells within each tissue are derived from one pluri-potent stem cell pool or whether they arise from committed progenitors belonging to distinct lineages. There is also a lack of information regarding the precise anatomical location of BMSSCs and DPSCs in their respective tissues. This is mainly attributed to the rarity of stem cells and the absence of specific markers that identify different developmental stages during osteogenesis and odontogenesis, particularly for primitive subpopulations. It has previously been hypothesized that one possible niche for precursors of osteoblasts and odontoblasts may be the microvasculature networks of bone marrow and dental pulp, respectively.[23,24]

Materials and Methods

Tissue Samples

Iliac crest-derived bone marrow mononuclear cells (BM-MNCs), from normal human adult volunteers were obtained under guidelines set by the Royal Adealaide Hospital Human Ethics Committee. Normal human impacted third molars were collected from young adults the University of Adelaide Dental Clinic Research under approved guidelines set by the University of Adelaide Human Ethics Committee, respectively. Discarded full thickness skin and peripheral adipose tissue were obtained from routine plastic surgery procedures from the Skin Cell Engineering Laboratory, under the guidelines set by the Royal Adelaide Hospital Human Ethics Committee. The pulp tissue was separated from the crown and root as previously described.[4] Single cell suspensions of dental pulp, skin and adipose tissue were prepared by enzymatic digestion in a solution of 3 mg/ml collagenase type I (Worthington Biochem, Freehold, N.J.) and 4 mg/ml dispase (Boehringer Mannheim, GMBH, Germany) for one to three hours at 37° C. Single cell suspensions were obtained by passing the cells through a 70 µm strainer (Falcon, B D Labware, Franklin Lakes, N.J.). Cell (0.01 to $1 \times 10^5$/well) preparations of bone marrow, dental pulp, skin and adipose were then used for either, immunolselection, RNA extraction, or direct culture in 6-well plates (Costar, Cambridge, Mass.) as described below.

Other human tissue specimens (Brain, liver, heart, kidney, lung, spleen, thymus, lymph node, pancreas, skin) were obtained from autopsies carried out at the Royal Adelaide Hospital during routine pathological examinations under approved guidelines set by the Royal Adelaide Hospital Human Ethics Committee. Small specimens approximately 0.5 cm$^2$ of each tissue type were placed into Tissue-Tek II cryomoulds 25 mm×20 mm×5 mm (Miles Laboratories; Naperville, Ill.) and embedded with O.C.T. compound medium (Miles Laboratories) by immersion into a 150 ml to 200 ml pyrex glass beaker of iso-pentane (BDH Chemicals, Poole, England) pre-cooled by suspending a glass beaker into a bath of liquid nitrogen. The isopentane has cooled when the bottom of the glass is white. The frozen sections were immediately stored at −80° C. Frozen sections of nerve and muscle tissue were obtained from the Histopathology Department of the I.M.V.S., South Australia and sections of foreskin were obtained from the Immunology Department of the I.M.V.S., South Australia. Sections of formalin fixed, paraffin embedded human foetal limb (52 days) were kindly provided by Dr. T. J. Khong from the Department of Histopathology, Women's and Children's Hospital, Adelaide, South Australia.

Colony Efficiency Assay and Culture

Single cell suspensions were plated at low plating densities (between 1,000 and 10,000 cells per well, as triplicates in six well plates) to assess colony-forming efficiency of different immunoselected cell fractions. The cells were cultured in alpha-Modification of Eagle's Medium supplemented with 20% foetal calf serum, 2 mM L-Glutamine, 100 µM L-ascorbate-2-phosphate, 100 U/ml penicillin and 100 µg/ml streptomycin at 37° C. in 5% $CO_2$. Day 14 cultures were fixed with 4% formalin, and then stained with 0.1% toluidine blue. Aggregates of equal to or greater than fifty cells were scored as clonogenic colonies equivalent to colony forming units-fibroblastic (CFU-F).

Magnetic-Activated Cell Sorting (MACS)

This procedure is a modification of that described elsewhere.[25] Briefly, approximately 1×10$^8$ BMMNCs were incubated with STRO-1bri supernatant (murine anti-human BMSSCs, IgM)[29] (½) for 1 hour on ice. The cells were then washed with PBS/5% FBS and resuspended in a 1/50 dilution of biotinylated goat anti-mouse IgM (µ-chain specific; Caltag Laboratories, Burlingame, Calif.) for 45 minutes on ice. After washing, the cells were incubated with streptavidin microbeads (Miltenyi Biotec, Bergisch Gladbach, F.R.G.) for 15 minutes on ice, then separated on a Mini MACS magnetic column (Miltenyi Biotec) according to the manufacturers recommendations.

Fluorescence Activated Cell Sorting (FACS)

STRO-1bri MACS isolated cells were incubated with a streptavidin-FITC conjugate (1/50; CALTAG Laboratories) for 20 minutes on ice then washed with PBS/5% FBS. Single-color fluorescence activated cell sorting (FACS) was performed using a FACStar$^{PLUS}$ flow cytometer (Becton Dickinson, Sunnyvale, Calif.). Dual color-FACS analysis was achieved by incubating MACS-isolated STRO-1$^{bri}$ BMMNCs with saturating (1:1) levels of CC9 antibody supernatant (mouse anti-human CD146/MUC-18/Mel-CAM, $IgG_{2a}$, Dr. Stan Gronthos) for one hour on ice. After washing with PBS/5% FBS, the cells were incubated with a second label goat anti-mouse $IgG_2$a (γ-chain specific) phycoerythrin (PE) conjugate antibody (1/50, CALTAG Laboratories) for 20 minutes on ice. The cells were then sorted using the automated cell deposition unit (ACDU) of a FACStar$^{PLUS}$ flow cytometer. Limiting dilution assay: seeded 1, 2, 3 4, 5, & 10 cells per well, 24 replicates, cultured in serum-deprived medium for 10 days as previously described[26]. Similarly, freshly prepared unfractionated BMMNCs were incubated with CC9 ($IgG_{2a}$) and 3G5 (IgM) antibodies or isotype-matched negative control antibodies for one hour on ice. After washing with PBS/5% FBS, the cells were incubated with a second label goat anti-mouse $IgG_{2a}$ (γ-chain specific) phycoerythrin (PE) and IgM (1/50; CALTAG Laboratories) conjugated antibodies for 30 minutes on ice. Cells were washed in PBS/%5 FBS prior to being analysed using a FACStar$^{PLUS}$ flow cytometer. Positive reactivity for each antibody was defined as the level of fluorescence greater than 99% of the isotype matched control antibodies.

Flow Cytometric Analysis

Single cell suspensions of ex vivo expanded bone marrow MPC were prepared by trypsin/EDTA treatment then incubated with neat STRO-1 supernatant or antibodies identifying different cell lineage-associated markers (10 µg/ml) for one hour on ice. The cells were then washed in PBS/5% FBS then incubated either with a goat anti-murine IgM-phycoerythrin (1/50, SouthernBiotechnologies), goat anti-murine or anti-rabbit IgG- phycoerythrin (Caltag Laboratories). For those antibodies identifying intracellular antigens, cell preparations were permeanbilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker with reference to the isotype matched negative control antibodies.

Immunhistochemistry

Human tissue sections (µm) were de-waxed in xylene and rehydrated through graded ethanol into PBS. Frozen tissue sections (µm) and cytospin preparations were fixed with cold acetone at −20° C. for 15 minutes then washed in PBS. The samples were subsequently treated with PBS containing 1.5% of hydrogen peroxide for 30 minutes, washed then blocked with 5% non-immune goat serum for 1 hour at room temperature. Samples were incubated with primary antibodies for 1 hour at room temperature. Antibodies used: Mouse ($IgG_1$ & $IgG_{2a}$) controls (Caltag, Burlingame, Calif.); Rabbit (Ig) control, 1A4 (anti-α smooth muscle actin, $IgG_1$), $2F_{11}$ (anti-neurofilament, $IgG_1$), F8/86 (murine anti-von Willebrand Factor, $IgG_1$) (Dako, Carpinteria, Calif.); STRO-1; CC9 (anti-CD146); LF-151 (rabbit anti-human dentinsialoprotein; Dr. L. Fisher, NIDCR/NIH, MD). Working dilutions: rabbit serum (1/500), monoclonal supernatants (½) and purified antibodies (10 µg/ml). Single staining was performed by incubating the samples with the appropriate secondary antibody, biotinylated goat anti-mouse IgM, $IgG_1$, $IgG_{2a}$ or biotinylated goat anti-rabbit for one hour at room temperature (Caltag Laboratories). Avidin-Peroxidase-complex and substrate were then added according to the manufacturer instructions (Vectastain ABC Kit standard, Vector Laboratories). Samples were counterstained with hematoxylin and mounted in aqueous media. Dual-fluorescence labeling was achieved by adding the secondary antibodies, goat anti-mouse IgM-Texas Red and IgG-FITC (CALTAG Laboratories), for 45 minutes at room temperature. After washing the samples were mounted in VECTASHIELD fluorescence mountant.

Imnmunomagnetic Bead Selection

Single cell suspensions of dental pulp tissue were incubated with antibodies reactive to STRO-1 (½), CD146 (½), or 3G5 (½) for 1 hour on ice. The cells were washed twice with PBS/1% BSA then incubated with either sheep anti-mouse IgG-conjugated or rat anti-mouse IgM-conjugated magnetic Dynabeads (4 beads per cell: Dynal, Oslo, Norway) for 40 minutes on a rotary mixer at 4° C. Cells binding to beads were removed using the MPC-1 magnetic particle concentrator (Dynal) following the manufactures recommended protocol.

Matrigel-Arteriole Assay

Single cell suspensions of ex vivo expanded bone marrow STRO-1$^{bright}$ MPC were prepared by trypsin/EDTA treatment then plated into 48-well plates containing 200 µl of matrigel. The STRO-1$^{bright}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed for alpha-smooth muscle actin identified with a goat-anti-murine IgG horse radish peroxidase antibody/Vectastaining Kit as described above.

Osteogenic, Adipogenic and Chondrogenic Differentiation of MPC in vitro

Single cell suspensions of ex vivo expanded adipose-derived MPC were cultured in αMEM supplemented with 10% FCS, 100 µM L-ascorbate-2-phosphate, dexamethasone $10^{-7}$ M and 3 mM inorganic phosphate previously shown to induce bone marrow MPC to form a mineralized bone matrix in vitro (Gronthos et al., 2003). Mineral deposits were identified by positive von Kossa staining. Adipogenesis was induced in the presence of 0.5 mM methylisobutylmethylxanthine, 0.5 µM hydrocortisone, and 60 µM indomethacin as previously described (Gronthos et al. 2003). Oil Red O staining was used to identify lipid-laden fat cells. Chondrogenic differentiation was assessed in aggregate cultures treated with 10 ng/ml TGF-β3 as described (Pittenger et al., 1999)

In vivo Transplantation Studies

Approximately $5.0 \times 10^6$ of ex vivo expanded cells derived from either STRO-1$^{bri}$/CD146$^+$ BMSSCs or CD146$^+$ DPSCs were mixed with 40 mg of hydroxyapatite/tricalcium phosphate (HA/TCP) ceramic powder (Zimmer Inc, Warsaw, Ind.) and then transplanted subcutaneously into the dorsal surface of 10-week-old immunocompromised beige mice (NIH-bg-nu-xid, Harlan Sprague Dawley, Indianapolis, Ind.) as previously described.[4] These procedures were performed in accordance to specifications of an approved animal protocol (NIDCR #00-113).

Reverse Transcription-Polymerase Chain Reaction.

Total RNA was prepared from STRO-1$^{BRT}$/CD146$^+$ sorted BMMNCs, and control cells (primary BMSSC cultures grown in the presence of $10^{-7}$ M dexamethasone for three weeks) using RNA STAT-60 (TEL-TEST Inc. Friendswood TX). First-strand cDNA synthesis was performed with a first-strand cDNA synthesis kit (GIBCO BRL, Life Technologies) using an oligo-dT primer. First strand cDNA (2 µl) was added to 46 µl of a 1X PCR master reaction mix (Roche Diagnostics, Gmbh Mannheim Germany) and 10 pMol of each human specific primer sets: CBFA1 (632bp, and three smaller alternative splice variants)[27] sense 5'-CTATGGAGAGGACGC-CACGCCTGG-3'[SEQ ID NO. 1], antisense, 5'-CATAGC-CATCGTAGCCTTGTCCT-3'[SEQ ID NO. 2]; osteocalcin (310bp)[4] sense, 5'-CATGAGAGCCCTCACA-3'[SEQ ID NO. 3], antisence, 5'-AGAGCGACACCCTAGAC-3'[SEQ ID NO. 4]; GAPDH (800bp)[4] sense, 5'-AGCCGCATCT-TCTTTTGCGTC-3'[SEQ ID NO. 5]; antisense 5'-TCATATTTGGCAGGTTTTTCT-3'[SEQ ID NO. 6]. The reactions were incubated in a PCR Express Hybaid thermal cycler (Hybaid, Franklin, MA) at 95° C. for 2 minutes for 1 cycle then 94° C./(30 sec), 60° C./(30 sec), 72° C./(45 sec) for 35 cycles, with a final 7 minute extension at 72° C. Following amplification, each reaction was analyzed by 1.5% agarose gel electrophoresis, and visualized by ethidium bromide staining.

Results

BMSSCs and DPSCs Express Vascular Associated Antigens STRO-1 and CD146 in vivo.

We have previously demonstrated the efficacy of magnetic activated cell sorting (MACS), to isolate and enrich for all detectable clonogenic colonies from aspirates of human marrow, based on their high expression of STRO-1 antigen.[25,26] To further characterize BMSSCs we incubated the STRO-1$^{bri}$ MACS isolated cells with another monoclonal antibody, CC9,[28] that recognizes the cell surface antigen CD146, also known as MUC-18, Mel-CAM and Sendo-1, that is present on endothelial and smooth muscle cells. These studies determined that CC9, selectively bound the STRO-1 bright expressing fraction (STRO-1$^{BRT}$) from the total STRO-1$^+$ population by dual-color FACS analysis (FIG. 10A). Cloning efficiency assays using Poisson distribution statistics, yielded a marked increase in the incidence of BMSSCs (1 colony per 5 STRO-1$^{BRT}$/CD146$^+$ cells plated), and achieved a $2 \times 10^3$ fold enrichment of the clonogenic colony population when compared to unfractionated marrow (FIG. 10B). No colony formation could be detected in STRO-1$^{BRT}$/CD146$^-$ cell fraction (data not shown).

The light scatter properties of STRO-1$^{BRT}$/CD146$^+$ marrow cells were typically larger and more granular than the nucleated erythroid cells and B-lymphocytes comprising the bulk of the STRO-1$^+$ population[29] (FIG. 10C-E). Cytospin preparations of STRO-1$^{BRT}$/CD146$^+$ sorted cells were found to be negative for the erythroid (glycophorin-A) and leukocyte (CD45) associated markers (data not shown). Confirmation that BMSSCs represented an early osteogenic precursor population was obtained by RT-PCR analysis of highly purified MACS/FACS-isolated STRO-1$^{BRT}$/CD146$^+$ cells, which failed to detect the early and late osteogenic, markers CBFA1 and osteocalcin, respectively (FIG. 10F). However, the progeny of STRO-1$^{BRT}$/CD146$^+$ sorted BMSSCs were found to express both CBFA1 and osteocalcin, following ex vivo expansion. Immunolocalization studies demonstrated that the CD146 antigen was predominantly expressed on blood vessel walls in sections of human bone marrow (FIG. 10G). Localization of both STRO-1 and CD146 was confined to large blood vessels in frozen sections of human bone marrow trephine (FIG. 10H).

Immunoselection protocols were subsequently used to determine if human DPSCs also expressed STRO-1 and CD146 in situ. The use of either MACS or FACS analysis to isolate DPSCs was restrictive due to the rarity of these cells (1 colony-forming cell per $2 \times 10^3$ cells plated) compounded by the limited number of pulp cells (approximately $10^5$ cells per pulp sample) obtained following processing. To circumvent this, we pooled several pulp tissues obtained from 3 to 4 different third molars per experiment and employed immunomagnetic bead selection on single cell suspensions of pulp tissue, based on their expression of either the STRO-1 or CD146 antigens. The STRO-1$^+$ fraction represented approximately 6% of the total pulp cell population. Comparative studies demonstrated that growth rates of individual colonies were unperturbed in the presence of magnetic beads (data not shown). Colony efficiency assays indicated that the majority of dental pulp derived colony-forming cells (82%) were represented in the minor, STRO-1$^+$ cell fraction analogous to BMSSCs (FIG. 11). The mean incidence of DPSCs in the STRO-1 positive fraction (329 colony-forming cells per $10^5$ cells plated ±56 SE, n=3) was six-fold greater than unfractionated pulp cells (55 colony-forming cells per $10^5$ cells plated±14 SE, n=3). Using a similar strategy, different fractions of human dental pulp cells were selected based on their reactivity with the antibody, CC9. Colony efficiency assays showed that a high proportion (96%) of dental pulp-derived clonogenic colonies were also present in the CD146$^+$ population, using immunomagnetic Dynal bead selection (FIG. 11). The mean incidence of clonogenic colonies in the CD146$^+$ fraction (296 colony-forming cells per $10^5$ cells plated ±37 SE, n=3) was seven-fold greater than unfractionated pulp cells (42 colony-forming cells per $10^5$ cells plated ±9 SE, n=3).

Immunolocalization studies showed that STRO-1 expression was restricted to blood vessel walls and perineurium surrounding the nerve bundles, but was not present in the mature odontoblast layer or fibrous tissue, in frozen sections of human dental pulp tissue (FIG. 12A-B). Furthermore, co-localization of CD146 with STRO-1 was detected on the outer blood vessel cell walls, with no reactivity to the surrounding fibrous tissue, odontoblast layer, and the perineurium of the nerve (FIG. 12C-D). Importantly, expression of human odontoblast-specific differentiation marker, dentin-sialoprotein (DSP), was restricted to the outer pulpal layer containing mature odontoblasts (FIG. 12E) and was absent in fibrous tissue, nerve bundles and blood vessels.

Differential Expression of the Perivascular Marker 3G5 by BMSSCs and DPSCs.

In the present study, flow cytometric analysis revealed that the cell surface antigen, 3G5, was highly expressed by a large proportion (54%) of hematopoietic marrow cells (FIG. 13A). This observation eliminated 3G5 as a candidate marker for isolating purified populations of BMSSCs directly from aspirates of human marrow. In addition, dual-FACS analysis based on 3G5 and STRO-1 expression was not possible since both antibodies shared the same isotype. Nevertheless, in vitro colony efficiency assays for different 3G5/CD146 FACS sorted subfractions demonstrated that only a minor proportion (14%) of bone marrow clonogenic colonies expressed the 3G5 antigen at low levels (FIG. 13B). Conversely, a larger proportion (63%) of clonogenic DPSCs (192 colony-forming cells per $10^5$ cells plated±18.4 SE n=3) were present in the 3G5$^+$ cell fraction following immunomagnetic bead selection (FIG. 11). 3G5 demonstrated specific reactivity to pericytes in frozen sections of human dental pulp tissue (FIG. 12F).

We next analyzed the expression of more specific markers of endothelial cells (von Willebrand Factor) and smooth muscle cells/pericytes (α-smooth muscle actin) on cytospin preparations using freshly isolated STRO-1$^{BRT}$/CD146$^+$ BMSSCs and CD146$^+$ expressing DPSCs. A large proportion of purified BMSSCs (67%), were found to be positive for α-smooth muscle actin (FIG. 14A), but lacked expression of von Willebrand Factor (FIG. 14B). Similarly, the majority of isolated DPSCs (85%) were also found to express α-smooth muscle actin, but not von Willebrand Factor (FIGS. 14C, 5D). Purified populations of STRO-1$^{BRT}$/CD146$^+$ BMSSCs and CD146$^+$ DPSCs were subsequently expanded in vitro then transplanted into immunocompromised mice to assess their developmental potentials in vivo. The progeny of cultured BMSSCs and DPSCs displayed distinct capacities, capable of regenerating the bone marrow and dental/pulp microenvironments, respectively (FIGS. 14E, F), and appeared identical to the developmental potential of non-selected multi-colony derived BMSSCs and DPSCs (4).

Discussion

The present study provides direct evidence that two mesenchymal stem cell populations, distinct in their ontogeny and developmental potentials, are both associated with the microvasculature of their respective tissues.

We employed different immunoselection protocols to demonstrate that BMSSCs and DPSCs could be efficiently retrieved from bone marrow aspirates and enzyme digested pulp tissue respectively, based primarily on their high expression of the STRO-1 antigen. This cell surface antigen is present on precursors of various stromal cell types including, marrow fibroblasts, osteoblasts, chondrocytes, adipocytes, and smooth muscle cells isolated from human adult and fetal bone marrow.[29,32-34] Previous studies have implicated STRO-1 as a marker of pre-osteogenic populations, where its expression is progressively lost following cell proliferation and differentiation into mature osteoblasts in vitro.[27,35,36] The STRO-1 antigen was also found to be present on the outer cell walls of human bone marrow and dental pulp blood vessels, in accord with previous studies that localized STRO-1 on large blood vessels, but not capillaries, in different adult tissues such as brain, gut, heart, kidney, liver, lung, lymph node, muscle, thymus.[6] Therefore, STRO-1 appears to be an early marker of different mesenchymal stem cell populations and infers a possible perivascular niche for these stem cell populations in situ.

To determine if BMSSCs and DPSCs were associated directly with blood vessels we utilized another antibody (CC9),[28] which recognizes the immunoglobulin super family member, CD146 (MUC-18/Mel-CAM), known to be present on smooth muscle, endothelium, myofibroblasts and Schwann cells in situ, as well as being a marker for some human neoplasms.[37] Notably, CD146 is not expressed by bone marrow hematopoietic stem cells, nor their progenitors. While the precise function of CD146 is not known, it has been linked to various cellular processes including cell adhesion, cytoskeletal reorganization, cell shape, migration and proliferation through transmembrane signaling.

In order to dissect the BMSSC population, STRO-1$^{BRT}$ expressing marrow cells were further distinguished from STRO-1$^+$ hematopoietic cells (predominantly glycophorin-A$^+$ nucleated erythrocytes) based on their expression of CD146, using dual-FACS analysis. Purified STRO-1$^{BRT}$/CD146$^+$ human BMSSCs displayed light scatter properties characteristic of large granular cells. Our study supports the findings of Van Vlasselaer and colleagues (1994)[38] who isolated partially purified BMSSCs from murine bone marrow following 5-fluoracil (5-FU) treatment, and identified this population as having high perpendicular and forward light scatter characteristics. Interestingly, freshly isolated 5-FU resistant murine BMSSCs were also found to be positive for two perivascular markers Sab-1 and Sab-2.[38] Conversely, more recent studies have shown that when BMSSCs are cultivated in vitro, the most primitive populations display low perpendicular and forward light scatter properties[39] and therefore may not reflect the true morphology of BMSSC in situ. In the present study, STRO-1$^{BRT}$/CD146$^+$ sorted human BMSSCs lacked the expression of CBFA1 and osteocalcin that identify committed early and late osteogenic populations, respectively,[40,41] indicating that BMSSCs exhibit a pre-osteogenic phenotype in human bone marrow aspirates. We found that a high proportion of freshly isolated STRO-1$^{BRT}$/CD146$^+$ BMSSCs expressed α-smooth muscle actin, but not the endothelial specific marker von Willebrand Factor, providing direct evidence that this primitive precursor population displays a characteristic perivascular phenotype. The present study also demonstrated the efficacy of using magnetic bead selection to isolate and enrich for DPSCs directly from human dental pulp tissue based on their expression of either STRO-1 or CD146. Immunolocalization of CD146 appeared to be specific to the microvasculature within dental pup. Co-localization of both STRO-1 and CD146 on the outer walls of large blood vessel in dental pulp tissue, implied that the majority of DPSCs arise from the microvasculature. However, since the STRO-1 antibody also reacted with the perineurium in dental pulp and peripheral nerve bundles (unpublished observations), further investigation is required to determine the role of this antigen in neural cell development.

Analogous to BMSSCs, freshly isolated CD146$^+$ DPSCs were found to express α-smooth muscle actin but not von Willebrand Factor. DPSCs were also shown to be an immature pre-odontogenic population both by their location distal from the dentin forming surface and by their lack of expression of the human odontoblast-specific dentin sialoprotein (DSP), which is restricted to the outer pulpal layer containing differentiated odontoblasts. We have previously described that ex vivo expanded human DPSCs do not express the precursor molecule, dentinsialophosphoprotein (DSPP), in vitro when cultured under non-inductive conditions.[4] Similar studies have shown that DSPP mRNA was highly expressed in freshly isolated odontoblast/pulp tissue, but was not detect in cultured dental papilla cells derived from rat incisors.[43,44] It is only when DPSCs are induced, either in vitro,[45] or by in vivo transplantation to form an ordered dentin matrix that DSPP is expressed.[4]

In vitro studies of ex vivo expanded BMSSCs and DPSCs supported the notion that their progeny were morphologically similar to cultured perivascular cells having a bipolar fibroblastic, stellar or flat morphology, rather than a polygonal endothelial-like appearance. In addition, we have previously shown that the progeny of BMSSC- and DPSC-derived colonies exhibit heterogeneous staining for both CD146 and α-smooth muscle actin, but lack expression of the endothelial markers, CD34 and von Willebrand Factor, in vitro.[4]

The observations that two different mesenchymal stem cell populations such as BMSSCs and DPSCs harbour in perivascular niches may have further implications for identifying stem cell populations in other adult tissues. Recent findings have identified human "reserve" multi-potent mesenchymal stem cells in connective tissues of skeletal muscle, and dermis derived from human fetal and adult samples.[56] However the exact location, developmental potential and ontogeny of these stem cells is still largely unknown. In the present study, identification of mesenchymal stem cell niches in bone marrow and dentin pulp may help elucidate the fundamental conditions necessary to selectively maintain and expand primitive multi-potential populations in vitro, in order to direct their developmental potentials in vivo.

EXAMPLE 8

Adult Human Bone Marrow MPC are Distinct from Stromal Precursor Cells, Haematopoietic Stem Cells and Angioblasts by their High Expression of the STRO-1 Antigen and Lack of CD34 Expression Postnatal bone marrow appears to be a hub of residential stem and precursor cell types responsible for blood cell formation (haematopoietic stem cells), endothelial development (angioblast), and connective tissue/stromal differentiation (stromal precursor cells/bone marrow stromal stem cells/mesenchymal stem cells). Recent work by our group (Gronthos et al. 2003; Shi and Gronthos 2003) has, for the first time, purified and characterised human multipotential bone marrow mesenchymal precursor cells (MPC) based on their high expression of the STRO-1 antigen and by their co-expression of the immunoglobulin superfamily members, VCAM-1 (CD106) and MUC-18 (CD146). Early studies by Simmons and Torok-Storb (1991a and b), have shown that bone marrow-derived STRO-1$^+$ stromal precursor cells, with the capacity to form adherent colonies in vitro, also expressed the haematopoietic stem cell marker, CD34, albeit at low levels. These studies used CD34 antibody-complement mediated cell lysis to eliminate a high proportion of adherent colony-forming cells in marrow aspirates (Simmons and Torok-Storb 1991b). It is important to note that while the STRO-1 antibody was generated following immunisation of mice with human CD34$^+$ bone marrow cells, this may have arisen due to the fact that the STRO-1 antigen is also expressed at moderate to low levels on CD34$^+$/Glycophorin-A$^+$ nucleated red cells and CD34$^+$/CD20$^+$ B-lymphocytes. We now offer direct evidence, using sophisticated fluorescence activated cell sorting technology that multipotential adult human bone marrow MPC express high levels of STRO-1, but lack expression to the stromal precursor cell, haematopoietic stem cell and angioblast maker (CD34), the leukocyte antigen (CD45), and the nucleated red cell marker (Glycophorin-A) (FIG. 15A-C). These data demonstrate that adult human bone marrow-derived MPC are a novel stem cell population, distinct from more mature stromal precursor cells, haematopoietic stem cells and angioblast (FIG. 16).

Unless otherwise indicated the materials and methods of this example are the same as those for Example 1.

FIG. 15. Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

FIG. 16. Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Gycophorin-A antigens, based on regions R1 and R2 as indicated in FIG. 15. These data are expressed as the mean incidence of colony-forming units for each cell fraction averaged from two separate experiments.

EXAMPLE 9

Identification of Mulipotential MPC in Different Human Tissues

While the existence and precise location of MPC in different tissues is largely unknown, we have recently demonstrated that MPC appear to reside in a perivascular niche in human bone marrow and dental pulp tissues (Shi and Gronthos 2003). These observations were based on a combination of immunohistochemical and immunoselection methods to identify and isolate different MPC populations based on their expression of the mesenchymal stem cell marker, STRO-1, the smooth muscle and pericyte markers, CD146, alpha-smooth muscle actin and the pericyte specific marker, 3G5. We have now extended these studies demonstrating the co-localization of STRO-1/CD146, STRO-1/alpha-smooth muscle actin, and 3G5/CD146 antigens in a wider variety of tissues including heart, liver, kidney, skin, spleen, pancreas, lymph node (FIG. 17).

To confirm our earlier findings that MPC can be derived from non-bone marrow tissue such as dental pulp, we used fluorescence activated cell sorting to isolate different MPC populations from adult human peripheral adipose. Single cell suspensions were obtained following digestion of the adipose tissue with collagenase and dispase as previously described (Shi and Gronthos 2003). The adipose-derived cells were then incubated with antibodies reactive against STRO-1, CD146 and 3G5. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 18). Following 12 days of culture, colonies (aggregates of 50 cells or more) were scored and displayed as the number of colonies per $10^5$ cells plated for each cell fraction. Our data demonstrated that MPC can be derived from adipose tissues based on their expression of STRO-1/3G5/CD146 antigens (FIG. 19). Dual colour flow cytometric analysis confirmed that only a minor proportion of adipose-derived cells co-expressed STRO-1/CD146 and 3G5/CD146 (FIG. 20). These findings are consistent with our previous observations that MPC can be isolated from both bone marrow and dental pulp tissue based on the same set of perivascular markers (Shi and Gronthos 2003). Furthermore, we provide evidence demonstrating that adipose derived MPC isolated by CD146 selection have the capacity to differentiate into different tissues such as bone, fat and cartilage (FIG. 21), as previous described (Gronthos et al. 2003).

Recent findings examining the existence of MPC in unrelated tissues such as skin has also been examined to further strengthen our hypothesis. Single cell suspensions were obtained following digestion of full thickness human skin with collagenase and dispase as described above for human adipose tissue. The skin-derived cells were then incubated with antibodies reactive against STRO-1, CD146 and 3G5 identified using either a goat anti-murine IgM or IgG- phycoerythrin. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 22). Following 12 days of culture, colonies (aggregates of 50 cells or more) were scored and displayed as the number of colonies per $10^5$ cells plated for each cell fraction. The data demonstrated that MPC can also be derived from skin based on their expression of STRO-1/3G5/CD146 antigens (FIG. 19). Collectively these data suggest that multipotential MPC can be identified and isolated in virtually all vascularised tissues derived from postnatal human tissue based on a common phenotype.

Unless otherwise indicated the materials and methods of this example are the same as those for Example 1.

FIG. 17. Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (Panel I), brain, kidney (Panel II), liver, heart (Panel III) and skin (Panel IV) 20×. The STRO-1 and 3G5 antibodies were identified using a goat anti-murine IgM- Texas Red while CD146 and alpha-smooth muscle actin were identified using a goat anti-murine or IgG-fluorescein isothiocyanate. Co-localization is indicated by overlapping areas of yellow and orange fluorescence (white arrows).

FIG. 18. Isolation of adipose-derived MPC by FACS. Representative flow cytometric histograms depicting the expression of STRO-1, CD146 and 3G5 in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

FIG. 19. Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 18), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

FIG. 20. Immunophenotypic analysis of adipose-derived MPC. Representative flow cytometric histograms depicting the co-expression of STRO-1 and CD146 (A) and 3G5 and CD146 in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate.

Approximately 60% and 50% of the CD146 positive cells co-express STRO-1 and 3G5, respectively. These data suggest that 10% or more of the CD164 positive cells co-express STRO-1 and 3G5.

FIG. 21. Developmental potential of purified Adipocyte-derived MPC in vitro. Preparations of primary MPC cultures derived from STRO-1$^+$/CD146$^+$ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

FIG. 22. Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

FIG. 23. Clonogenic skin-derived MPC are positive for STRO-1bri/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5, then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

EXAMPLE 10

Immunophenotypic Analysis of ex vivo Expanded Human Bone Marrow Mesenchymal Precursor Cells We have previously reported that multipotential mesenchymal precursor cells (MPC) can be purified from adult human bone marrow mononuclear cells based on the phenotype STRO-1$^{bright}$/VCAM-1 (CD106)$^+$ or STRO-1$^{bright}$/MUC-18 (CD146)$^+$ (Gronthos et al. 2003; Shi and Gronthos 2003). The MPC population can be readily propagated in vitro under defined culture conditions (Gronthos et al. 2003). We now present data characterising the ex vivo expanded MPC progeny based on markers associated with different cell lineages, at both the mRNA and protein level, using reverse transcriptase-polymerase chain reaction (RT-PCR) and flow cytometric analysis, respectively.

In the first series of experiments, semi-quantitative RT-PCR analysis was employed to examine the gene expression profile of various lineage-associated genes present in the cultured MPC populations (FIG. 24). Relative gene expression for each cell marker was assessed with reference to the expression of the house-keeping gene, GAPDH, using ImageQuant software (FIG. 24B). In addition, single-colour flow cytometric analysis was used to examine the protein expression profile of ex vivo expanded MPC based on their expression of cell lineage-associated markers (FIG. 24A). A summary of the general phenotype based on the gene and protein expression of the cultured MPC is presented in Table 1. Direct comparison of the gene expression profile of MPC described in the present patent demonstrated clear differences between this cell population and mesenchymal stem cells (MSC) previously described by Pittenger et al. 1999, (Table 1).

Unless otherwise indicated the materials and methods of this example are the same as those for Example 1.

FIG. 24A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeanbilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker (bold line) with reference to the isotype matched negative control antibodies (thin line).

FIG. 24B. Gene expression profile of cultured MPC. Single cell suspensions of ex vivo expanded bone marrow MPC were prepared by trypsin/EDTA treatment and total cellular RNA was prepared. Using RNAzo1B extraction method total RNA was isolated and used as a template for cDNA synthesis, prepared using standard procedure. The expression of various transcripts was assessed by PCR amplification, using a standard protocol as described previously (Gronthos et al. 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the house-keeping gene, GAPDH, using ImageQuant software.

FIG. 25. Ex vivo expanded STRO-1$^{bri}$ MPC can develop into arterioles in vitro. Single cell suspensions of ex vivo expanded bone marrow STRO-1$^{bri}$ and STRO-1$^{dull}$ MPC were prepared by trypsin/EDTA treatment then plated into 48-well plates containing 200 μl of matrigel. The STRO-1$^{dull}$ (A) and STRO-1$^{bri}$ (B) MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

TABLE 1

Comparison between cultured human Mesenchymal Precursor Cells (MCP's) and cultured human Mesenchymal Stem Cells (MSC's) following ex vivo expansion. Antigens found to be present on cell surface, intracellular or in the extra cellular matrix. MPCs express markers of tissues with different developmental origin, i.e. ECT-ectoderm, MES-mesoderm and END-endoderm.

| ANTIGEN | MSC | MPC | Differentiated Cell Type. |
|---|---|---|---|
| STRO-1 | −ve | +ve | |
| Collagen II | −ve | +ve | Chondrocyte (MES) |
| Collagen IV | −ve | +ve | Fibroblast (MES) |
| Laminin | −ve | +ve | Fibroblast (MES) |
| Bone Sialoprotein (BSP) | −ve | +ve | Osteoblast (MES) |
| Osteocalcin (OCN) | −ve | +ve | Osteoblast (MES) |
| Nestin | ND | +ve | Neural (ECT) |
| Glial Fibrillary Acidic Protein (GFAP) | ND | +ve | Neural (ECT) |
| CBFA1 | −ve | +ve | Osteoblast (MES) |
| Osterix (OSX) | ND | +ve | Osteoblast (MES) |
| Osteocalcin (OCN) | −ve | +ve | Osteoblast (MES) |
| Sox9 | ND | +ve | Chondrocyte (MES) |
| Collagen X (COL X) | +ve | +ve | Chondrocyte (MES) |
| Leptin | ND | +ve | Adipose (MES) |
| GATA-4 | ND | +ve | Cardiomyocyte (MES) |
| Transferrin (TFN) | ND | +ve | Hepatocyte (END) |
| Flavin Containing Monooxygenase (FCM) | ND | +ve | Hepatocyte (END) |

TABLE 2

RT-PCR primers and conditions for the specific amplification of human mRNA

| Target Gene | Sense/Antisense (5'-3') Primer Sequences | Product Size |
|---|---|---|
| GAPDH | CACTGACACGTTGGCAGTGG/ [SEQ ID NO. 7] CATGGAGAAGGCTGGGGCTC [SEQ ID NO. 8] | 417 |
| Leptin | ATGCATTGGGAACCCTGTGC/ [SEQ ID NO. 9] GCACCCAGGGCTGAGGTCCA [SEQ ID NO. 10] | 492 |

TABLE 2-continued

RT-PCR primers and conditions for the specific amplification of human mRNA

| Target Gene | Sense/Antisense (5'-3') Primer Sequences | Product Size |
|---|---|---|
| CBFA-1 | GTGGACGAGGCAAGAGTTTCA/ [SEQ ID NO. 11] TGGCAGGTAGGTGTGGTAGTG [SEQ ID NO. 12] | 632 |
| OCN | ATGAGAGCCCTCACACTCCTC/ [SEQ ID NO. 13] CGTAGAAGCGCCGATAGGC [SEQ ID NO. 14] | 289 |
| GFAP | CTGTTGCCAGAGATGGAGGTT/ [SEQ ID NO. 15] TCATCGCTCAGGAGGTCCTT [SEQ ID NO. 16] | 370 |
| Nestin | GGCAGCGTTGGAACAGAGGTTGGA/ [SEQ ID NO. 17] CTCTAAACTGGAGTGGTCAGGGCT [SEQ ID NO. 18] | 460 |
| GATA-4 | GACTTCTCAGAAGGCAGAG/ [SEQ ID NO. 19] CTATCCTCCAAGTCCCAGAG [SEQ ID NO. 20] | 800 |
| PDGFβ-R | AATGTCTCCAGCACCTTCGT/ [SEQ ID NO. 21] AGCGGATGTGGTAAGGCATA [SEQ ID NO. 22] | 650 |
| Osterix | GGCACAAAGAAGCCGTACTC/ [SEQ ID NO. 23] CACTGGGCAGACAGTCAGAA [SEQ ID NO. 24] | 247 |
| COL X | AGCCAGGGTTGCCAGGACCA/ [SEQ ID NO. 25] TTTTCCCACTCCAGGAGGGC [SEQ ID NO. 26] | 387 |
| SOX9 | CTC TGC CTG TTT GGA CTT TGT/ [SEQ ID NO. 27] CCT TTG CTT GCC TTT TAC CTC [SEQ ID NO. 28] | 598 |
| Ang-1 | CCAGTCAGAGGCAGTACATGCTA AGAATTGAGTTA/ [SEQ ID NO. 29] GTTTTCCATGGTTTTGTCCCGCAGTA [SEQ ID NO. 30] | 300 |

REFERENCES

Alberico et al (1987) *Blood;* 69: 1120.
Allen, T. D.: Haemopoietic microenvironment in vitro: Ultrastructural aspects. In Porter R, Whelan J (eds); "Microenvironments in haemopoietic and lymphoid differentiation." *CIBA Foundation Symposium* 84. London: Pitman Medical, 1981, pp 38.
Allen et al (1990a) *Immunol. Ser.* 49: 1.
Allen et al (1990b) Marrow Biology and Stem Cells. In *Colony Stimulating Factors: Molecular and Cellular Biology,* edited by T. M. Dexter, J. M. Garland and N. G. Testa; New York: Marcel Decker, 1990b, pp 1-38.
Anklesaria et al (1989) *Blood.* 74: 1144.
Anklesaria et al (1987) *Proc. Natl. Acad. Sci. USA.* 84: 7681.
Bennett et al (1991) *Journal of Cell Science.* 99: 131.
Bentley (1982) *Br J Haematol.* 50: 1.
Castro-Malaspina et al (1980) *Blood.* 56: 289.
Castro-Malaspina et al (1981) *Blood.* 57: 781.
Dexter et al (1977) *J Cell Physiol.* 91: 335.
Dexter et al Kroc Foundation Series Vol 18; Alan R. Liss, Inc., New York; p. 57-96, 1984
Fong et al (1997) *BioTechniques,* 23: 1029.
Friedenstein (1976) *International Review of Cytology.* 47: 327.
Friedenstein et al (1970) *Cell Tissue Kinetics.* 3: 393.
Friedenstein et al (1992) *Bone and Mineral.* 18: 199.
Friedenstein (1980) 'Stromal mechanisms of bone marrow: cloning in vitro and retransplantation in vivo'. Immunology of Bone Marrow Transplantation; Ed: S. Thienfelder; Springer-Verlag Berlin; p 19-29, 1980
Gronthos et al (1994) *Blood.* 84: 4164.
Gronthos and Simmons (1995) *Blood.* 85: 929.
Huang and Terstappen (1992) *Nature.* 360: 745.
Keating et al (1982) *Nature.* 298: 280.
Kim et al. (1994) *Science,* 266: 2011.
Knopse et al. (1966) *Blood.* 28: 398.
Knopse et al (1972) *Blood.* 39: 331.
Lichtman (1981) *Experimental Hematology.* 9: 391.
Long (1992) *Exp Hematol.* 20: 288.
MacManus and Weiss (1984) *Blood.* 64: 1036.
McIntyre and Bjornson (1986) *Exp Hematol.* 14: 833.
Miltenyi et al (1990) *Cytometry.* 11: 231.
Owen (1985) *Bone and Mineral Research.* 3: 1.
Owen and Friedenstein (1988) *CIBA Foundation Symposium.* 136: 42.
Perkins and Fleischman (1990) *Blood.* 75: 620.
Piersma et al. (1983) *Br. J Haematol.* 54: 285.
Rothstein et al (1985) *Blood.* 65: 744
Simmons and Gronthos. (1991) *International Journal of Cell Cloning.* 9: 408 [abstract].
Simmons et al (1994) Advances in Bone Marrow Purging and Processing: Fourth International Symposium. Progress in Clinical Biological Research. 389: 271.
Simmons et al (1987) *Nature.* 328: 429.
Simmons and Torok-Storb (1991a) *Blood.* 78: 55.
Simmons and Torok-Storb (1991b) *Blood.* 78: 2848.
Tavassoli and Friedenstein (1983) *Ann J Hematol.* 15: 195.
Tavassoli and Crosby (1968) *Science.* 161: 54.
Testa et al (1988) Long-term Bone Marrow Damage after Cytotoxic Treatment: Stem Cells and Microenvironment In Hematopoiesis: Long-term Effects of Chemotherapy and Radiation (Hematology/vol 8), eds. Testa, N. G., Gale, R. P., Marcel Dekker, Inc. New York and Basel, 1988, pp 75-92
Van Vlasselaer et al (1994) *Blood.* 84: 753.
Waller et al (1995) *Blood.* 85: 2422.
Weiss (1976) *Anatomical Record.* 186: 161.
1. Spradling et al., (2001). *Nature* 414(6859):98-104.
2. Bianco and Robey (2001) *Nature* 414(6859):118-121.
3. Fuchs and Segre (2000) *Cell* 100(1):143-55.
4. Gronthos et al., (2000) *Proc Natl Acad Sci USA* 97(25): 13625-30.
5. Kuznetsov et al., (1997). *J Bone Miner Res* 12(9): 1335-47.
6. Bianco et al., (2001) *Stem Cells* 19(3):180-92.
7. Lichtman (1981) *Exp Hematol* 9(4):391-410.
8. Weiss (1976) *Anatomical Record* 186:161-84.
9. Weiss and Sakai H (1984) *Am J Anat* 170(3):447-63.
10. Dexter and Shadduck (1980) *J Cell Physiol* 102(3):279-86.
11. Orchardson and Cadden (2001) *Dent Update* 28(4):200-6, 208-9.
12. Peters and Balling (1999) *Trends Genet* 15(2):59-65.
13. Thesleff and Aberg (1999) *Bone* 25(1):123-5.

14. Friedenstein et al., (1974) *Transplantation* 17(4):331-40.
15. Castro-Malaspina et al., (1980) *Blood* 56(2):289-301.
16. Weissman (2000) *Cell* 100(1):157-68.
17. Uchida et al., (2000) *Proc Natl Acad Sci USA* 97(26): 14720-5.
18. Kuznetsov et al., (2001) *J Cell Biol* 153(5):1133-40.
19. Shi et al. (2001) *Bone* 29(6):532-39.
20. Pittenger et al., (1999) *Science* 284(5411):143-7.
21. Gronthos et al., (2002) *J Dent Res* 81(8):531-5.
22. Owen and Friedenstein (1988) *Ciba Found Symp* 136(29): 42-60.
23. Doherty et al., (1998) *J Bone Miner Res* 13(5):828-38.
24. Bianco and Cossu (1999). *Exp Cell Res* 251(2):257-63.
25. Gronthos et al., (1998) Isolation, purification and in vitro manipulation of human bone marrow stromal precursor cells. In: Beresford J N and Owen M E (ed) Marrow stromal cell culture. Cambridge University Press, Cambridge, UK, pp 26-42.
26. Gronthos and Simmons (1995) *Blood* 85(4):929-40.
27. Gronthos et al., (1999) *J Bone Miner Res* 14(1):47-56.
28. Filshie et al., (1998) *Leukemia* 12(3):414-21.
29. Simmons and Torok-Storb (1991). *Blood* 78(1):55-62.
30. Canfield and Schor (1998) Osteogenic potential of vascular pericytes. In: Beresford J N and Owen M E (ed) Marrow stromal cell culture. Cambridge University Press, Cambridge, UK, pp 128-148.
31. Riminucci and Bianco (1998) The bone marrow stroma in vivo: ontogeny, structure, cellular composition and changes in disease. In: Beresford J N and Owen M E (ed) Marrow stromal cell culture. Cambridge University Press, UK, Cambridge, UK, pp 10-25.
32. Gronthos et al., (1994) *Blood* 84(12):4164-73.
33. Oyajobi et al., (1999) *J Bone Miner Res* 14(3):351-61.
34. Dennis et al., (2002). *Cells Tissues Organs* 170(2-3):73-82.
35. Stewart et al., (1999) *J Bone Miner Res* 14(8): 1345-56.
36. Ahdjoudj et al., (2001) *J Cell Biochem* 81(1):23-38.
37. Shih (1999) *J Pathol* 189(1):4-11.
38. Van Vlasselaer et al., (1994) *Blood* 84(3):753-63.
39. Prockop et al.,(2001). *Cytotherapy* 3(5):393-6.
40. Ducy et al., (1997) *Cell* 89(5):747-54.
41. Komori et al., (1997) *Cell* 89(5):755-64.
42. Woodbury et al., (2000) *J Neurosci Res* 61(4):364-70.
43. Dey et al., (2001) *Arch Oral Biol* 46(3):249-60.
44. Ueno et al., (2001) *Matrix Biol* 20(5-6):347-55.
45. Couble et al., (2000) *Calcif Tissue Int* 66(2): 129-38.
46. Nehls and Drenckhahn (1993) *Histochiemistry* 99(1):1-12.
47. Schor et al., (1995) *Clin Orthop* 313:81-91.
48. Pugach et al., (1999) *Arkh Patol* 61(4):18-21.
49. Nehls et al., (1992) *Cell Tissue Res* 270(3):469-74.
50. Brighton et al., (1992) *Clin Orthop* 275:287-99.
51. Nayak et al., (1988) *J Exp Med* 167(3):1003-15.
52. Andreeva et al., (1998) *Tissue Cell* 30(1):127-35.
53. Cattoretti et al., (1993) *Blood* 81(7): 1726-38.
54. Charbord et al., (2000) *J Hematother Stem Cell Res* 9(6): 935-43.
55. Dennis and Charbord (2002) *Stem Cells* 20(3):205-14.
56. Young et al., (2001) *Anat Rec* 263(4):350-60.
Gronthos et al., (2003). *Journal of Cell Science* 116: 1827-1835.
Pittenger et al., (1999). *Science* 284, 143-7.
Simmons and Torok-Storb (1991a). *Blood* 78(1):55-62.
Simmons and Torok-Storb (1991b). *Blood* 78:2848.
Shi and Gronthos. (2003). *Journal of Bone and Mineral Research*, 18(4): 696-704.

The invention claimed is:

1. A method of generating bone tissue in a subject comprising administering to the subject a population of cells enriched for STRO-1$^{bright}$ cells, or culture expanded colony-forming-unit-fibroblasts (CFU-Fs) derived therefrom, wherein such STRO-1$^{bright}$ cells are mesenchymal precursor cells capable of giving rise to CFU-Fs, so as to generate bone tissue in the subject.

2. The method of claim 1, wherein the mesenchymal precursor cells carry at least one additional marker selected from the group of surface markers consisting of THY-1, VCAM-1, STRO-2, and CD146.

3. The method of claim 2, wherein the mesenchymal precursor cells carry the markers STRO-1 and VCAM-1.

4. The method of claim 1, wherein the STRO-1$^{bright}$ cells are negative for at least one marker selected from the group consisting of CBFA-1, collagen type II, PPARγ2, and glycophorin A.

* * * * *

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
ctatggagag gacgccacgc ctgg                                              24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
catagccatc gtagccttgt cct                                               23

<210> SEQ ID NO 3
<211> LENGTH: 16
<212> TYPE: DNA
<213> ORGANISM: Artificial Sequence
<220> FEATURE:
<223> OTHER INFORMATION: Primer

<400> SEQUENCE: 3
```

```
catgagagcc ctcaca                                                         16

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
agagcgacac cctagac                                                        17

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agccgcatct tcttttgcgt c                                                   21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcatatttgg caggtttttc t                                                   21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cactgacacg ttggcagtgg                                                     20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
catggagaag gctggggctc                                                     20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atgcattggg aaccctgtgc                                                     20

<210> SEQ ID NO 10
<211> LENGTH: 20
<212> TYPE: DNA
```

```
<213> ORGANISM: Artificial Sequence
<220> FEATURE:
<223> OTHER INFORMATION: Primer

<400> SEQUENCE: 10
gcacccaggg ctgaggtcca                                              20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gtggacgagg caagagtttc a                                            21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tggcaggtag gtgtggtagt g                                            21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
atgagagccc tcacactcct c                                            21

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cgtagaagcg ccgataggc                                               19

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
ctgttgccag agatggaggt t                                            21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcatcgctca ggaggtcctt                                              20
```

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggcagcgttg gaacagaggt tgga                                            24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctctaaactg gagtggtcag ggct                                            24

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gacttctcag aaggcagag                                                  19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctatcctcca agtcccagag                                                 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aatgtctcca gcaccttcgt                                                 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agcggatgtg gtaaggcata                                                 20

<210> SEQ ID NO 23
<211> LENGTH: 20
<212> TYPE: DNA
<213> ORGANISM: Artificial Sequence
<220> FEATURE:

<223> OTHER INFORMATION: Primer

<400> SEQUENCE: 23
ggcacaaaga agccgtactc    20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cactgggcag acagtcagaa    20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agccagggtt gccaggacca    20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ttttcccact ccaggagggc    20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ctctgcctgt ttggactttg t    21

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
cctttgcttg cctttacct c    21

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
ccagtcagag gcagtacatg ctaagaattg agtta    35

```
<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
gttttccatg gttttgtccc gcagta                                              26
```